US008962553B2

(12) United States Patent
Wahren et al.

(10) Patent No.: US 8,962,553 B2
(45) Date of Patent: Feb. 24, 2015

(54) METHOD OF TREATING A DIABETIC SUBJECT HAVING A MICROVASCULAR IMPAIRMENT DISORDER BY A PEGYLATED C-PEPTIDE

(71) Applicant: Cebix Ab, San Diego, CA (US)

(72) Inventors: John Wahren, Stockholm (SE); Sheri Barrack, Corte Madera, CA (US); James Callaway, San Diego, CA (US); Michelle Mazzoni, San Diego, CA (US); Howard Foyt, Escondido, CA (US); Mark Daniels, San Diego, CA (US)

(73) Assignee: Cebix AB, San Diego, CA (US)

( * ) Notice: Subject to any disclaimer, the term of this patent is extended or adjusted under 35 U.S.C. 154(b) by 0 days.

(21) Appl. No.: 13/680,753

(22) Filed: Nov. 19, 2012

(65) Prior Publication Data

US 2013/0130973 A1    May 23, 2013

Related U.S. Application Data

(60) Provisional application No. 61/561,254, filed on Nov. 17, 2011.

(51) Int. Cl.
*A61K 38/28* (2006.01)
*A61P 3/10* (2006.01)
*C07K 17/02* (2006.01)

(52) U.S. Cl.
CPC ........................................ *C07K 17/02* (2013.01)
USPC .............. 514/5.9; 514/6.1; 514/8.3; 530/303; 530/324

(58) Field of Classification Search
None
See application file for complete search history.

(56) References Cited

U.S. PATENT DOCUMENTS

| | | | |
|---|---|---|---|
| 4,904,584 A | 2/1990 | Shaw | |
| 5,252,714 A | 10/1993 | Harris et al. | |
| 5,629,384 A | 5/1997 | Caliceti et al. | |
| 5,650,234 A | 7/1997 | Dolence et al. | |
| 5,672,662 A | 9/1997 | Harris et al. | |
| 5,739,208 A | 4/1998 | Harris | |
| 5,824,784 A | 10/1998 | DePrince et al. | |
| 5,900,461 A | 5/1999 | Harris | |
| 5,932,462 A | 8/1999 | Caliceti et al. | |
| 5,990,237 A | 11/1999 | Bentley et al. | |
| 6,436,386 B1 | 8/2002 | Roberts et al. | |
| 6,448,369 B1 | 9/2002 | Bentley et al. | |
| 6,495,659 B2 | 12/2002 | Bentley et al. | |
| 6,500,645 B1 | 12/2002 | Kjeldsen et al. | |
| 6,558,924 B1 | 5/2003 | Stahl et al. | |
| 6,602,498 B2 | 8/2003 | Shen | |
| 6,828,401 B2 | 12/2004 | Nho et al. | |
| 6,858,736 B2 | 2/2005 | Nho et al. | |
| 7,026,440 B2 | 4/2006 | Bentley et al. | |
| 7,855,177 B1 * | 12/2010 | Wahren et al. ............ | 514/5.9 |
| 2001/0043934 A1 | 11/2001 | L'Italien et al. | |
| 2003/0143596 A1 | 7/2003 | Bentley et al. | |
| 2007/0105809 A1 | 5/2007 | Rusconi | |
| 2009/0281029 A1 | 11/2009 | Nojima et al. | |
| 2012/0178676 A1 | 7/2012 | Barrack et al. | |
| 2012/0220542 A1 | 8/2012 | Barrack et al. | |

FOREIGN PATENT DOCUMENTS

| | | | |
|---|---|---|---|
| EP | 1932855 A1 | | 6/2008 |
| EP | 2206721 | * | 7/2010 |
| GB | 2104382 A | | 3/1983 |
| WO | WO-95/00162 | | 1/1995 |
| WO | WO-98/13384 | | 4/1998 |
| WO | WO-9907735 | | 2/1999 |
| WO | WO 00/41546 A2 | | 7/2000 |
| WO | WO 2008/012528 A1 | | 1/2008 |
| WO | WO 2008/118387 | * | 10/2008 |
| WO | WO 2010033204 | * | 3/2010 |
| WO | WO2011/146518 A2 | | 11/2011 |

OTHER PUBLICATIONS

Polonsky et al., J. Clin. Invest. 77: 98-105, 1986.*
Ekberg et al., Diabetes Care 30: 71-76, 2007.*
Akerblom et al., "From pathomechanisms to prediction, prevention and improved care of insulin-dependent diabetes mellitus in children," Ann. Med. (1997) 29(5):383-385.
Alber et al., "Nucleotide sequence of the triose phosphate isomerase gene of *Saccharomyces cerevisiae*," J. Mol. Appl. Genet. (1982) 1(5):419-434.
Altschul et al., "Basic local alignment search tool," J. Mol. Biol. (1990) 215(3):403-410.
Altschul et al., "Gapped Blast and Psi-Blast: a new generation of protein database search programs," Nucleic Acids Res. (1997) 25(17):3389-3402.
Beaucage et al., "Deoxynucleoside Phosphoramidites—A new class of key intermediates for deoxypolynucleotide synthesis," Tetrahedron Lett. (1981) 22:1859-1869.
Carrillo et al., "The multiple sequence alignment problem in biology," SIAM J. Applied Math. (1988) 48:1073.
Cotter et al., "Effects of proinsulin C-peptide in experimental diabetic neuropathy: vascular actions and modulation by nitric oxide synthase inhibition," Diabetes (2003) 52:1812-1817.
Croker et al., "An expert virtual instrument approach to the automated, data dependent MS/MS and LC/MS/MS analysis of proteins," J. Biomol. Tech. (2000) 11(3):135-141.
Cryer et al., "The barrier of hypoglycemia in diabetes," Diabetes (2008) 57(12):3169-3176.
Desai et al., "Autoimmune diabetes in adults: lessons from the UKPDS," Diabetic Med. (2008) 25(suppl 2):30-34.
Devereux et al., "A comprehensive set of sequence analysis programs for the VAX," Nucleic Acids Res. (1984) 12(1):387-395.
Donnelly et al., "Frequency and predictors of hypoglycaemia in Type 1 and insulin-treated Type 2 diabetes: a population-based study," Diabetic Med. (2005) 22(6):749-755.

(Continued)

*Primary Examiner* — Gyan Chandra
(74) *Attorney, Agent, or Firm* — Morrison & Foerster LLP

(57) ABSTRACT

The present invention relates to PEGylated C-peptide derivatives comprising at least one PEG group attached to the N-terminus, which exhibit improved pharmacokinetic and biological activity in vivo.

49 Claims, 28 Drawing Sheets

(56) References Cited

OTHER PUBLICATIONS

England et al., "Distal symmetric polyneuropathy: A definition for clinical research: Report of the American Academy of Neurology, the American Association of Electrodiagnostic Medicine, and the American Academy of Physical Medicine and Rehabilitation," Neurology (2005) 64(2):199-207.

Faber et al., "Kinetics of human connecting peptide in normal and diabetic subjects," J. Clin. Invest. (1978) 62(1):197-203.

Fourlanos et al., "Latent autoimmune diabetes in adults (LADA) should be less latent," Diabetologia (2005) 48(11):2206-2212.

Huang et al., "Human proinsulin C-peptide from a precursor overexpressed in *Pichia pastoris*," Acta Biochim. Biophys. Sin. (Shanghai) (2006) 38(8):586-92.

Henriksson et al., "Unordered structured of proinsulin C-peptide in aqueous solution and in the presence of lipid vesicles," Cell. Mol. Life Sci. (2000) 57(2):337-342.

Hills et al., "Cellular and physiological effects of C-peptide," Clin. Sci. (Lond) (2009) 116:565-574.

Ido et al., "Prevention of vascular and neural dysfunction in diabetic rats by C-peptide," Science (1997) 277:563-566.

Johnson et al., "Novel fragmentation process of peptides by collision-induced decomposition in a tandem mass spectrometer: differentiation of leucine and isoleucine," Anal. Chem. (1987) 59(21):2621-2625.

Jonasson et al., "Gene fragment polymerization gives increased yields of recombinant human proinsulin C-peptide," Gene (1998) 210(2):203-210.

Jonasson et al., "Integrated bioprocess for production of human proinsulin C-peptide via heat release of an intracellular heptameric fusion protein," J. Biotechnol. (2000) 76(2-3):215-26.

Kitamura et al., "Proinsulin C-peptide rapidly stimulates mitogen-activated protein kinases in Swiss 3T3 fibroblasts: requirement of protein kinase C, phosphoinositide 3-kinase and pertussis toxin-sensitive G-protein," Biochem. J. (2001) 355:123-129.

Kunt et al., "The effect of human proinsulin C-peptide on erythrocyte deformability in patients with Type I diabetes mellitus," Diabetologia (1999) 42(4):465-471.

Li et al., "Expression of C-peptide multiple gene copies in *Escherichia coli* and stabilities of C-peptide in aqueous solution," Acta Biochim. Biophys. Sin. (2003) 35(11):986-992.

Ludvigsson et al., "GAD treatment and insulin secretion in recent-onset type 1 diabetes," New Engl. J. Med. (2008) 359(18):1909-1920.

Matthes et al., "Simultaneous rapid chemical synthesis of over one hundred oligonucleotides on a microscale," EMBO J. (1984) 3(4):801-805.

Nilsson et al., "Integrated production of human insulin and its C-peptide," J. Biotechnol. (1996) 48(3):241-50.

Ohtomo et al., "C-peptide stimulates rat renal tubular $Na^+$, $K^+$-ATPase activity in synergism with neuropeptide Y," Diabetologia (1996) 39:199-205.

Ohtomo et al., "Differential effects of proinsulin C-peptide fragments on $Na^+$, $K^+$ATPase activity of renal tubule segments," Diabetologia (1998) 41:287-291.

Palmer et al., "Is latent autoimmune diabetes in adults distinct from type 1 diabetes or just type 1 diabetes at an older age?," Diabetes (2005) 54(suppl 2):S62-67.

Pasut et al., "Protein, peptide and non-peptide drug PEGylation for therapeutic application," Expert Opin. Ther. Patents (2004) 14(6):859-893.

Polonsky et al., "Twenty-four-hour profiles and pulsatile patterns of insulin secretion in normal and obese subjects," J. Clin. Invest. (1988) 81(2):442-448.

Pramanik et al., "C-peptide binding to human cell membranes: importance of Glu27," Biochem. Biophys. Res. Commun. (2001) 284:94-98.

Reeck et al., ""Homology" in proteins and nucleic acids: a terminology muddle and a way out of it," Cell (1987) 50(5):667.

Retnakaran et al., "The response to short-term intensive insulin therapy in type 2 diabetes," Diabetes Obes. Metab. (2009) 12(1):65-71.

Rigler et al., "Specific binding of proinsulin C-peptide to human cell membranes," Proc. Natl. Acad. Sci. USA (1999) 96:13318-13323.

Roberts et al., "Chemistry for peptide and protein PEGylation," Adv. Drug Delivery Rev. (2002) 54:459-476.

Roepstorff et al., "Letter to the editors: proposal for a common nomenclature for sequence ions in mass spectra of peptides," Biomedical Spectrometry (1984) 11(11):601.

Russell, "Transcription of the triose-phosphate-isomerase gene of *Schizosaccharomyces pombe* initiates from a start point different from that in *Saccharomyces cerevisiae*," Gene (1985) 40:125-130.

Shafqat et al., "Proinsulin C-peptide and its analogues induce intracellular $Ca2^+$ increases in human renal tubular cells," Cell. Mol. Life Sci. (2002) 59:1185-1189.

Smith et al., "Identification of common molecular subsequences," J. Mol. Biol. (1981) 147(1):195-197.

Turner et al., "Insulin deficiency and insulin resistance interaction in diabetes: estimation of their relative contribution by feedback analysis from basal plasma insulin and glucose concentrations," Metabolism (1979) 28(11):1086-1096.

Veronese et al., "Introduction and overview of peptide and protein PEGylation," Adv. Drug Delivery Rev. (2002) 54(4):453-609.

Wahren et al., "Role of C-peptide in human physiology," Am. J. Phyisiol. (2000) 278:E759-E768.

Wahren et al., "Biological effects of c-peptide and proinsulin," International Textbook of Diabetes Mellitus, Chapter 10, John Wiley & Sons (2004) pp. 165-181.

Wahren et al., "C-peptide improves erectile function in type 1 diabetes," DiabetesPro (2011) Abstract No. 1039-P, retrieved from the Internet Sep. 30, 2013, 1 page.

Zalipsky, "Chemistry of polyethylene glycol conjugates with biologically active molecules," Adv. Drug Delivery Rev. (1995) 16:157-182.

Zander et al., "Effect of 6-week course of glucagon-like peptide 1 on glycaemic control, insulin sensitivity, and beta-cell function in type 2 diabetes: a parallel-group study," Lancet (2002) 359(9309):824-830.

Munte et al., "Solution Structure of Human Proinsulin C-Peptide," *FEBS J. 2995*, 272, 4284-4293, (2005).

NOF Corporation Catalogue Ver. 8 (Apr. 2006).

Foyt, H. et al., "Pharmacokinetics, Safety, and Tolerability of a Long-Acting C-Peptide (CBX129801) in Patients with Type 1 Diabetes," presented at 48th Annual Meeting of the European Association for the Study of Diabetes (EASD), Berlin, Germany, Oct. 1-5, 2012. (1 page).

"Highlights of Prescribing Information" for OMONTYS®, Revised Mar. 2012. (14 pages).

Important Drug Information, Feb. 2013. (2 pages).

Medawala, W. et al., "A Molecular Level Understanding of Zinc Activation of C-peptide and its Effects on Cellular Communication in the Bloodstream," Rev. Diabet. Stud. 2009, 6(3), 1148-1158.

Meyer, J.A. et al., "Metal-Activated C-Peptide Facilitates Glucose Clearance and the Release of a Nitric Oxide Stimulus via the GLUT1 Transporter," *Diabetologia* 2008, 51(1), 175-182.

International Preliminary Report on Patentability for PCT/US2012/065892, issued May 20, 2014, 6 pages.

* cited by examiner

METHOD OF TREATING A DIABETIC SUBJECT HAVING A MICROVASCULAR IMPAIRMENT DISORDER BY A PEGYLATED C-PEPTIDE

This application claims the benefit of U.S. provisional application No. 61/561,254, filed Nov. 17, 2011, the disclosure of which is hereby incorporated by reference as if written herein in its entirety.

BACKGROUND OF THE INVENTION

Field of the Invention

The present invention relates to modified forms of C-peptide, and methods for their use. In one aspect, the modified forms of C-peptide comprise PEGylated C-peptide derivatives comprising at least one PEG group attached to the N-terminus which exhibit superior pharmacokinetic and biological activity in vivo.

C-peptide is the linking peptide segment between the A- and B-chain segments in the proinsulin molecule. After cleavage and processing in the endoplasmic reticulum of pancreatic islet β-cells, insulin and C-peptide are generated. C-peptide is co-secreted with insulin in equimolar amounts from the pancreatic islet β-cells into the portal circulation. Besides of its contribution to the folding of the two-chain insulin structure, further biologic activity of C-peptide was questioned for many years after its discovery.

Type 1 diabetes is generally characterized by insulin and C-peptide deficiency, due to an autoimmune destruction of the pancreatic islet β-cells. The patients are therefore dependent on exogenous insulin to sustain life. Several factors may be of importance for the pathogenesis of the disease, e.g., genetic background, environmental factors, and an aggressive autoimmune reaction following a temporary infection (Akerblom H K et al.: *Annual Medicine* 29(5): 383-385, (1997)). Currently insulin-requiring patients are provided with exogenous insulin which has been separated from the C-peptide, and thus do not receive exogenous C-peptide therapy. By contrast, most type 2 diabetic subjects initially still produce both insulin and C-peptide endogenously, but are generally characterized by insulin resistance in skeletal muscle, adipose tissue, and liver, among other tissues.

Many type 1 diabetic patients and other insulin-requiring patients eventually develop and suffer from a constellation of long-term complications of diabetes that in many cases are more severe and widespread than in type 2 diabetes. For example, microvascular complications involving the retina, kidneys, and nerves are a major cause of morbidity and mortality in patients with type 1 diabetes.

There is increasing support for the concept that C-peptide deficiency may play a role in the development of the long-term complications of insulin-requiring diabetic patients. Additionally, in vivo as well as in vitro studies in diabetic animal models and in patients with type 1 diabetes demonstrate that C-peptide possesses hormonal activity (Wahren J et al.: *American Journal of Physiology* 278: E759-E768, (2000); Wahren J et al.: In *International Textbook of Diabetes Mellitus* Ferranninni E, Zimmet P, De Fronzo R A, Keen H, Eds. John Wiley & Sons, (2004), p. 165-182). Thus, C-peptide used as a complement to conventional insulin therapy may provide an effective approach to the management of long-term complications in insulin-requiring patients.

Studies to date suggest that C-peptide's therapeutic activity involves the binding of C-peptide to a G-protein-coupled membrane receptor, activation of $Ca^{2+}$-dependent intracellular signalling pathways, and phosphorylation of the MAP-kinase complex, eliciting increased activities of sodium/potassium ATPase and endothelial nitric oxide synthase (eNOS) (Hills C E et al.: Clin Sci (Lond) 116: 565-574, (2009)). The latter two enzyme systems are known to be deficient in diabetes mellitus and have been implicated in the pathogenesis of diabetic peripheral neuropathy. The cellular mechanism of action for positive effects of C-peptide on nerve conduction is based on the demonstrated binding of C-peptide to cell membranes of a number of different cell types, notably endothelial cells, fibroblasts, and renal tubular cells (Rigler R et al.: Proc Natl Acad Sci USA 96: 13318-13323, (1999)).

Despite the promise of using C-peptide to treat and prevent the long-term complications of insulin-requiring diabetes, the short biological half-life and requirement to dose C-peptide multiple times per day via subcutaneous (S.C.; s.c.) injection, or intravenous (I.V.; i.v.) administration, have hindered commercial development.

In a single-dose pharmacokinetic study of C-peptide in patients with type 1 diabetes, recombinant human C-peptide was administered subcutaneously at doses of 150 nmol, 600 nmol, 1800 nmol, and intravenously at a dose of 150 nmol with a wash-out period of at least three days. This study resulted in the following measured pharmacokinetic parameters:

TABLE A

Pharmacokinetic Parameters (mean ± SD) at Different Doses of C-peptide (n = 12)

|  | 0.45 mg (150 nmol) i.v. | 0.45 mg (150 nmol) s.c. | 1.8 mg (600 nmol) s.c. | 5.4 mg (1800 nmol) s.c. |
|---|---|---|---|---|
| AUC (nmol/L*min) | 613 ± 100 | 532 ± 110 | 2280 ± 397 | 7401 ± 1205 |
| $C_{max}$ (nmol/L) | 30.8 ± 6.57 | 3.7 ± 1.04 | 14.3 ± 3.22 | 40.3 ± 7.03 |
| $t_{max}$ (min) | — | 50 ± 11.4 | 65 ± 14.4 | 73 ± 20.4 |
| $t_{1/2}$ (min) | 68 ± 13.5 | 68 ± 21.0 | 61 ± 15.7 | 68 ± 14.4 |
| CL (L/min) | 0.25 ± 0.046 | — | — | — |
| CL/F (L/min) | — | 0.29 ± 0.067 | 0.27 ± 0.047 | 0.25 ± 0.041 |
| Vz (L) | 25.6 ± 7.65 | — | — | — |
| Vz/F (L) | — | 28.3 ± 8.96 | 23.4 ± 5.27 | 24.4 ± 5.47 |
| Vss (L) | 10.9 ± 1.97 | — | — | — |
| F (%) | — | 86.9 ± 12.07 | — | — |

An independent study found the half-life of C-peptide to be 42.5 minutes (range of 39.4-48.5 minutes) in subjects with type 1 diabetes and 33.5 minutes (range of 24.9-45.3 minutes) in healthy subjects (Faber O K et al., J. Clin. Invest., 62; 197-203, (1978)). Based on the extensive clinical data accumulated on native C-peptide, a target plasma concentration in the range of 1-3 nM is needed to achieve full therapeutic benefit, which is consistent with the physiological range of the native peptide (Polonsky K S et al., J. Clin. Invest., 81; 442-448, (1988)). The dose of native C-peptide required to obtain a plasma concentration of 1-3 nM for most of the day was 1.5 mg/day, or 10.5 mg/week, whereas the dose of CBX129801 required to obtain a plasma concentration in the range of 1-3 nM is approximately 1 mg/week. The nominal molecular weight for CBX129801 is 46,000 Da. A nominal weight is provided because one C-peptide molecule (3019 Da) is coupled to PEG that has an average molecular weight of 43,000 Da. Therefore, the equivalent amount of C-peptide (in mg) contained within a 1 mg dose of CBX129801 can be expressed as follows:

$$1 \text{ mg } CBX129801 \times \frac{3019 \text{ Da C-peptide}}{46{,}000 \text{ Da } CBX129801} = \frac{0.066 \text{ mg C-peptide}}{\text{mg } CBX129801}$$

Since 1 mg of CBX129801 contains the molar equivalent of 0.066 mg of C-peptide, the systemic exposure of C-peptide is significantly improved by PEGylation (~160-fold on a molar basis). This improved exposure is due to the lower apparent clearance and prolonged half-life.

The present invention is focused on the development of PEGylated versions of C-peptide that retain the biological activity of the native C-peptide and exhibit superior pharmacokinetic properties. These improved therapeutic forms of C-peptide enable the development of more effective therapeutic regimens for the treatment of long-term complications of insulin-requiring diabetic patients, and require significantly less frequent administration.

In one aspect, these therapies are targeted to patients with diabetes, and in a further aspect to insulin-requiring patients. In another aspect, the insulin-requiring patients are suffering from one or more long-term complications of diabetes.

These improved methods are based on clinical studies showing that PEGylated versions of C-peptide retain the biological activity of the native molecule, while exhibiting superior pharmacokinetic characteristics.

SUMMARY OF THE INVENTION

In one embodiment, the present invention includes a PEGylated C-peptide comprising a PEG moiety covalently attached to the N-terminus of C-peptide. In one aspect, the PEGylated C-peptide of the invention comprises a linear polymer PEG polymer. In another aspect, the PEGylated C-peptide of the invention comprises a branched chain PEG polymer.

In another embodiment, the present invention includes a PEGylated C-peptide wherein the PEGylated C-peptide has the structure:

$$R_1-O-(CH_2CH_2O)_{n1}-CH_2$$
$$R_1-O-(CH_2CH_2O)_{n2}-CH$$
$$H_2C-OCH_2CH_2CH_2NHC(CH_2)_3C$$

EAEDLQVGQVELGGGPGAGSLQPLALEGSLQ wherein;
$R_1$ = alkyl;
$n_1$ is 200 to 800;
$n_2$ is 200 to 800.

In another aspect of any of these PEGylated C-peptides, the PEG moiety has a molecular weight of between about 10 kDa and about 80 kDa. In another aspect, the PEG moiety has a molecular weight of between about 20 kDa and about 60 kDa. In another aspect, the PEG moiety has a molecular weight of between about 30 kDa and about 50 kDa. In another aspect, the PEG moiety has a molecular weight of between about 35 kDa and about 45 kDa. In another aspect, the PEG moiety has a molecular weight of about 40 kDa.

In certain embodiments, disclosed herein is a method for administering PEGylated C-peptide to a patient in need thereof, comprising administering to the patient PEGylated C-peptide.

In certain embodiments, disclosed herein is a method for treating one or more long-term complications of diabetes, comprising administering to the patient a therapeutic dose of PEGylated C-peptide.

In further embodiments, the long-term complications of diabetes are selected from the group consisting of peripheral neuropathy, autonomic neuropathy, nephropathy, erectile dysfunction, female sexual dysfunction and retinopathy.

In further embodiments, the long-term complication of diabetes is peripheral neuropathy.

In further embodiments, the long-term complication of diabetes is nephropathy.

In further embodiments, the long-term complication of diabetes is erectile dysfunction.

In further embodiments, the long-term complication of diabetes is female sexual dysfunction.

In further embodiments, the long-term complication of diabetes is retinopathy.

In further embodiments, the method further comprises the dosing and administration of insulin.

In further embodiments, the method further comprises the step of adjusting the dosage amount, type, or frequency of insulin administered based on monitoring the patient's altered insulin requirements after administration of the therapeutic dose of PEGylated C-peptide, wherein the adjusted dose of insulin reduces the risk, incidence, or severity of hypoglycemia, wherein the adjusted dose of insulin is at least 10% less than the patient's insulin dose prior to starting PEGylated C-peptide treatment.

In further embodiments, the adjusted dose of insulin is about 10% less to about 50% less than the patient's insulin dose prior to starting PEGylated C-peptide treatment.

In further embodiments, the administration of an equimolar molar amount of PEGylated C-peptide produces a 2-fold increased AUC or $C_{ave}$ as compared to C-peptide, a 5-fold increased AUC or $C_{ave}$ as compared to C-peptide, a 10-fold increased AUC or $C_{ave}$ as compared to C-peptide, a 20-fold increased AUC or $C_{ave}$ as compared to C-peptide, a 30-fold increased AUC or $C_{ave}$ as compared to C-peptide, a 40-fold increased AUC or $C_{ave}$ as compared to C-peptide, a 50-fold increased AUC or $C_{ave}$ as compared to C-peptide, a 60-fold increased AUC or $C_{ave}$ as compared to C-peptide, a 70-fold increased AUC or $C_{ave}$ as compared to C-peptide, a 80-fold increased AUC or $C_{ave}$ as compared to C-peptide, a 90-fold increased AUC or $C_{ave}$ as compared to C-peptide, a 100-fold increased AUC or $C_{ave}$ as compared to C-peptide, a 110-fold increased AUC or $C_{ave}$ as compared to C-peptide, a 120-fold increased AUC or $C_{ave}$ as compared to C-peptide, a 130-fold increased AUC or $C_{ave}$ as compared to C-peptide, a 140-fold increased AUC or $C_{ave}$ as compared to C-peptide, or a 150-fold increased AUC or $C_{ave}$ as compared to C-peptide.

In further embodiments, the administration of an equimolar molar amount of CBX129801 produces a 2-fold increased AUC or $C_{ave}$ as compared to C-peptide, a 5-fold increased AUC or $C_{ave}$ as compared to C-peptide, a 10-fold increased AUC or $C_{ave}$ as compared to C-peptide, a 20-fold increased AUC or $C_{ave}$ as compared to C-peptide, a 30-fold increased AUC or $C_{ave}$ as compared to C-peptide, a 40-fold increased AUC or $C_{ave}$ as compared to C-peptide, a 50-fold increased AUC or $C_{ave}$ as compared to C-peptide, a 60-fold increased AUC or $C_{ave}$ as compared to C-peptide, a 70-fold increased AUC or $C_{ave}$ as compared to C-peptide, a 80-fold increased AUC or $C_{ave}$ as compared to C-peptide, a 90-fold increased AUC or $C_{ave}$ as compared to C-peptide, a 100-fold increased AUC or $C_{ave}$ as compared to C-peptide, a 110-fold increased AUC or $C_{ave}$ as compared to C-peptide, a 120-fold increased AUC or $C_{ave}$ as compared to C-peptide, a 130-fold increased AUC or $C_{ave}$ as compared to C-peptide, a 140-fold increased AUC or $C_{ave}$ as compared to C-peptide, or a 150-fold increased AUC or $C_{ave}$ as compared to C-peptide.

In further embodiments, the dose of a PEGylated C-peptide is less than 90% of an equally efficacious dose of C-peptide, less than 80% of an equally efficacious dose of C-peptide, less than 70% of an equally efficacious dose of C-peptide, less than 60% of an equally efficacious dose of C-peptide, less than 50% of an equally efficacious dose of C-peptide, less than 40% of an equally efficacious dose of C-peptide, less than 30% of an equally efficacious dose of C-peptide, less than 20% of an equally efficacious dose of C-peptide, less than 10% of an equally efficacious dose of C-peptide, less than 9% of an equally efficacious dose of C-peptide, less than 8% of an equally efficacious dose of C-peptide, less than 7% of an equally efficacious dose of C-peptide, less than 6% of an equally efficacious dose of C-peptide, less than 5% of an equally efficacious dose of C-peptide, less than 4% of an equally efficacious dose of C-peptide, less than 3% of an equally efficacious dose of C-peptide, less than 2% of an equally efficacious dose of C-peptide, less than 1% of an equally efficacious dose of C-peptide, or less than 0.67% of an equally efficacious dose of C-peptide.

In further embodiments, the dose of CBX129801 is less than 90% of an equally efficacious dose of C-peptide, less than 80% of an equally efficacious dose of C-peptide, less than 70% of an equally efficacious dose of C-peptide, less than 60% of an equally efficacious dose of C-peptide, less than 50% of an equally efficacious dose of C-peptide, less than 40% of an equally efficacious dose of C-peptide, less than 30% of an equally efficacious dose of C-peptide, less than 20% of an equally efficacious dose of C-peptide, less than 10% of an equally efficacious dose of C-peptide, less than 9% of an equally efficacious dose of C-peptide, less than 8% of an equally efficacious dose of C-peptide, less than 7% of an equally efficacious dose of C-peptide, less than 6% of an equally efficacious dose of C-peptide, less than 5% of an equally efficacious dose of C-peptide, less than 4% of an equally efficacious dose of C-peptide, less than 3% of an equally efficacious dose of C-peptide, less than 2% of an equally efficacious dose of C-peptide, less than 1% of an equally efficacious dose of C-peptide, or less than 0.67% of an equally efficacious dose of C-peptide.

In further embodiments, a PEGylated C-peptide has a 2-fold decreased clearance as compared to C-peptide, a 5-fold decreased clearance as compared to C-peptide, a 10-fold decreased clearance as compared to C-peptide, a 20-fold decreased clearance as compared to C-peptide, a 50-fold decreased clearance as compared to C-peptide, a 100-fold decreased clearance as compared to C-peptide, a 200-fold decreased clearance as compared to C-peptide, a 400-fold decreased clearance as compared to C-peptide, a 600-fold decreased clearance as compared to C-peptide, a 800-fold decreased clearance as compared to C-peptide, a 1000-fold decreased clearance as compared to C-peptide, a 1200-fold decreased clearance as compared to C-peptide, a 1400-fold decreased clearance as compared to C-peptide, or a 1600-fold decreased clearance as compared to C-peptide.

In further embodiments, CBX129801 has a 2-fold decreased clearance as compared to C-peptide, a 5-fold decreased clearance as compared to C-peptide, a 10-fold decreased clearance as compared to C-peptide, a 20-fold decreased clearance as compared to C-peptide, a 50-fold decreased clearance as compared to C-peptide, a 100-fold decreased clearance as compared to C-peptide, a 200-fold decreased clearance as compared to C-peptide, a 400-fold decreased clearance as compared to C-peptide, a 600-fold decreased clearance as compared to C-peptide, a 800-fold decreased clearance as compared to C-peptide, a 1000-fold decreased clearance as compared to C-peptide, a 1200-fold decreased clearance as compared to C-peptide, a 1400-fold decreased clearance as compared to C-peptide, or a 1600-fold decreased clearance as compared to C-peptide.

In further embodiments, a PEGylated C-peptide has a 2-fold increased half-life as compared to C-peptide, a 5-fold increased half-life as compared to C-peptide, a 10-fold increased half-life as compared to C-peptide, a 20-fold increased half-life as compared to C-peptide, a 50-fold increased half-life as compared to C-peptide, a 100-fold increased half-life as compared to C-peptide, a 200-fold increased half-life as compared to C-peptide, a 300-fold increased half-life as compared to C-peptide, a 400-fold increased half-life as compared to C-peptide, a 500-fold increased half-life as compared to C-peptide, a 600-fold increased half-life as compared to C-peptide, a 700-fold increased half-life as compared to C-peptide, a 800-fold increased half-life as compared to C-peptide, a 900-fold increased half-life as compared to C-peptide, a 1000-fold increased half-life as compared to C-peptide, a 1100-fold increased half-life as compared to C-peptide, a 1200-fold increased half-life as compared to C-peptide, a 1300-fold increased half-life as compared to C-peptide, a 1400-fold increased half-life as compared to C-peptide, or a 1500-fold increased half-life as compared to C-peptide.

In further embodiments, CBX129801 has a 2-fold increased half-life as compared to C-peptide, a 5-fold increased half-life as compared to C-peptide, a 10-fold increased half-life as compared to C-peptide, a 20-fold increased half-life as compared to C-peptide, a 50-fold increased half-life as compared to C-peptide, a 100-fold increased half-life as compared to C-peptide, a 200-fold increased half-life as compared to C-peptide, a 300-fold increased half-life as compared to C-peptide, a 400-fold increased half-life as compared to C-peptide, a 500-fold increased half-life as compared to C-peptide, a 600-fold increased half-life as compared to C-peptide, a 700-fold increased half-life as compared to C-peptide, a 800-fold increased half-life as compared to C-peptide, a 900-fold increased half-life as compared to C-peptide, a 1000-fold increased half-life as compared to C-peptide, a 1100-fold increased half-life as compared to C-peptide, a 1200-fold increased half-life as compared to C-peptide, a 1300-fold increased half-life as compared to C-peptide, a 1400-fold increased half-life as compared to C-peptide, or a 1500-fold increased half-life as compared to C-peptide.

In further embodiments, the $C_{min}$ of PEGylated C-peptide is between about 0.1 nM and about 15 nM, between about 0.34 nM and about 9.0 nM, between about 0.47 nM and about 6.8 nM, between about 1.7 nM and about 4.9 nM, between about 0.1 nM and about 1.5 nM, between about 0.34 nM and about 0.60 nM, between about 0.8 nM and about 1.6 nM, between about 1.4 nM and about 2.1 nM, between about 4.6 nM and about 9.0 nM, between about 0.1 nM and about 0.2 nM, between about 0.2 nM and about 0.3 nM, between about 0.3 nM and about 0.4 nM, between about 0.4 nM and about 0.6 nM, between about 0.6 nM and about 0.8 nM, between about 0.8 nM and about 1.0 nM, between about 0.1 nM and about 0.5 nM, between about 0.5 nM and about 1.0 nM, between about 1.0 nM and about 1.5 nM, between about 1.5 nM and about 2.0 nM, between about 2.0 nM and about 2.5 nM, between about 2.5 nM and about 3.0 nM, between about 3.0 nM and about 3.5 nM, between about 3.5 nM and about 4.0 nM, between about 4.0 nM and about 4.5 nM, between about 4.5 nM and about 5.0 nM, between about 0.1 nM and about 1.0 nM, between about 1.0 nM and about 2.0 nM, between about 2.0 nM and about 3.0 nM, between about 3.0 nM and about 4.0 nM, between about 4.0 nM and about 5.0 nM, between about 5.0 nM and about 6.0 nM, between about 6.0 nM and about 7.0 nM, between about 7.0 nM and about 8.0 nM, between about 8.0 nM and about 9.0 nM, between about 9.0 nM and about 10 nM, between about 10 nM and about 11 nM, between about 11 nM and about 12 nM, between about 12 nM and about 13 nM, between about 13 nM and about 14 nM, between about 14 nM and about 15 nM, between about 0.1 nM and about 2.0 nM, between about 2.0 nM and about 4.0 nM, between about 4.0 nM and about 6.0 nM, between about 6.0 nM and about 8.0 nM, between about 8.0 nM and about 10 nM, between about 10 nM and about 12 nM, between about 12 nM and about 14 nM, between about 0.1 nM and about 5.0 nM, between about 5.0 nM and about 10 nM, between about 10 nM and about 15 nM, or between about 15 nM or about 20 nM.

In further embodiments, the $C_{min}$ of PEGylated C-peptide is between about 0.34 nM and about 9.0 nM.

In further embodiments, the $C_{min}$ of PEGylated C-peptide is between about 0.47 nM and about 6.8 nM.

In further embodiments, the $C_{min}$ of PEGylated C-peptide is between about 1.7 nM and about 4.9 nM.

In further embodiments, the $C_{min}$ of PEGylated C-peptide is about 1.7 nM.

In further embodiments, the $C_{min}$ of PEGylated C-peptide is about 4.9 nM.

In further embodiments, the $C_{avg}$ of PEGylated C-peptide is between about 0.5 nM and about 15.0 nM, between about 0.44 nM and about 12.2 nM, between about 0.62 nM and about 9.5 nM, between about 2.0 nM and about 5.9 nM, between about 0.44 nM and about 0.79 nM, between about 1.4 nM and about 1.9 nM, between about 1.7 nM and about 2.4 nM, between about 1.2 nM and about 2.0 nM, between about 4.0 nM and about 9.0 nM, between about 6.9 nM and about 12.2 nM, between about 0.1 nM and about 0.2 nM, between about 0.2 nM and about 0.3 nM, between about 0.3 nM and about 0.4 nM, between about 0.4 nM and about 0.6 nM, between about 0.6 nM and about 0.8 nM, between about 0.8 nM and about 1.0 nM, between about 0.1 nM and about 0.5 nM, between about 0.5 nM and about 1.0 nM, between about 1.0 nM and about 1.5 nM, between about 1.5 nM and about 2.0 nM, between about 2.0 nM and about 2.5 nM, between about 2.5 nM and about 3.0 nM, between about 3.0 nM and about 3.5 nM, between about 3.5 nM and about 4.0 nM, between about 4.0 nM and about 4.5 nM, between about 4.5 nM and about 5.0 nM, between about 0.1 nM and about 1.0 nM, between about 1.0 nM and about 2.0 nM, between about 2.0 nM and about 3.0 nM, between about 3.0 nM and about 4.0 nM, between about 4.0 nM and about 5.0 nM, between about 5.0 nM and about 6.0 nM, between about 6.0 nM and about 7.0 nM, between about 7.0 nM and about 8.0 nM, between about 8.0 nM and about 9.0 nM, between about 9.0 nM and about 10 nM, between about 10 nM and about 11 nM, between about 11 nM and about 12 nM, between about 12 nM and about 13 nM, between about 13 nM and about 14 nM, between about 14 nM and about 15 nM, between about 0.1 nM and about 2.0 nM, between about 2.0 nM and about 4.0 nM, between about 4.0 nM and about 6.0 nM, between about 6.0 nM and about 8.0 nM, between about 8.0 nM and about 10 nM, between about 10 nM and about 12 nM, between about 12 nM and about 14 nM, between about 0.1 nM and about 5.0 nM, between about 5.0 nM and about 10 nM, between about 10 nM and about 15 nM, or between about 15 nM or about 20 nM.

In further embodiments, the $C_{avg}$ of PEGylated C-peptide is between about 0.44 nM and about 12.2 nM.

In further embodiments, the $C_{avg}$ of PEGylated C-peptide is between about 0.62 nM and about 9.5 nM.

In further embodiments, the $C_{avg}$ of PEGylated C-peptide is between about 2.0 nM and about 5.9 nM.

In further embodiments, the $C_{avg}$ of PEGylated C-peptide is about 2.0 nM.

In further embodiments, the $C_{avg}$ of PEGylated C-peptide is about 5.9 nM.

In further embodiments, the $C_{max}$ of PEGylated C-peptide is between about 1.0 nM and about 20 nM, between about 0.5 nM and about 14.5 nM, between about 0.72 nM and about 11.2 nM, between about 2.3 nM and about 6.7 nM, between about 0.50 nM and about 0.92 nM, between about 1.6 nM and about 2.1 nM, between about 2.0 nM and about 2.6 nM, between about 7.9 nM and about 14.5 nM, between about 0.1 nM and about 0.2 nM, between about 0.2 nM and about 0.3 nM, between about 0.3 nM and about 0.4 nM, between about 0.4 nM and about 0.6 nM, between about 0.6 nM and about 0.8 nM, between about 0.8 nM and about 1.0 nM, between about 0.1 nM and about 0.5 nM, between about 0.5 nM and about 1.0 nM, between about 1.0 nM and about 1.5 nM, between about 1.5 nM and about 2.0 nM, between about 2.0 nM and about 2.5 nM, between about 2.5 nM and about 3.0 nM, between about 3.0 nM and about 3.5 nM, between about 3.5 nM and about 4.0 nM, between about 4.0 nM and about 4.5 nM, between about 4.5 nM and about 5.0 nM, between about 0.1 nM and about 1.0 nM, between about 1.0 nM and about 2.0 nM, between about 2.0 nM and about 3.0 nM, between about 3.0 nM and about 4.0 nM, between about 4.0 nM and about 5.0 nM, between about 5.0 nM and about 6.0 nM, between about 6.0 nM and about 7.0 nM, between about 7.0 nM and about 8.0 nM, between about 8.0 nM and about 9.0 nM, between about 9.0 nM and about 10 nM, between about 10 nM and about 11 nM, between about 11 nM and about 12 nM, between about 12 nM and about 13 nM, between about 13 nM and about 14 nM, between about 14 nM and about 15 nM, between about 0.1 nM and about 2.0 nM, between about 2.0 nM and about 4.0 nM, between about 4.0 nM and about 6.0 nM, between about 6.0 nM and about 8.0 nM, between about 8.0 nM and about 10 nM, between about 10 nM and about 12 nM, between about 12 nM and about 14 nM, between about 0.1 nM and about 5.0 nM, between about 5.0 nM and about 10 nM, between about 10 nM and about 15 nM, or between about 15 nM or about 20 nM.

In further embodiments, the $C_{max}$ of PEGylated C-peptide is between about 0.5 nM and about 14.5 nM.

In further embodiments, the $C_{max}$ of PEGylated C-peptide is between about 0.72 nM and about 11.2 nM.

In further embodiments, the $C_{max}$ of PEGylated C-peptide is between about 2.3 nM and about 6.7 nM.

In further embodiments, the $C_{max}$ of PEGylated C-peptide is about 2.3 nM.

In further embodiments, the $C_{max}$ of PEGylated C-peptide is about 6.7 nM.

In further embodiments, the $T_{max}$ of PEGylated C-peptide is between about 1.8 to about 3.3 days, between 0.5-10 days, between 1-7 days, between 1-2 days, between 2-3 days, between 3-4 days, between 4-5 days, between 5-6 days, between 6-7 days, between 7-8 days, between 8-9 days, between 9-10 days, between 1-3 days, between 2-4 days, between 5-7 days, between 6-8 days, between 7-10 days, between 1-4 days, between 2-5 days, between 3-6 days, between 4-7 days, between 5-8 days, between 6-9 days, or between 7-10 days.

In further embodiments, the $T_{max}$ of PEGylated C-peptide is between about 1.8 to about 3.3 days.

In certain embodiments, the half-life of PEGylated C-peptide is greater than about 6 hours, greater than about 12 hours, greater than about 18 hours, greater than about 1 day, greater than about 2 days, greater than about 3 days, greater than about 4 days, greater than about 5 days, greater than about 6 days, greater than about 7 days, greater than about 8 days, greater than about 9 days, greater than about 10 days, greater than about 11 days, greater than about 12 days, greater than about 13 days, greater than about 14 days, greater than about 15 days, greater than about 16 days, greater than about 17 days, greater than about 18 days, greater than about 19 days, greater than about 20 days, between 1-20 days, between 1-2 days, between 2-3 days, between 3-4 days, between 4-5 days, between 5-6 days, between 6-7 days, between 7-8 days, between 8-9 days, between 9-10 days, between 10-11 days, between 11-12 days, between 12-13 days, between 13-14 days, between 14-15 days, between 15-16 days, between 16-17 days, between 17-18 days, between 18-19 days, between 19-20 days, between 1-3 days, between 2-4 days, between 3-5 days, between 4-6 days, between 5-7 days, between 6-8 days, between 7-9 days, 8-10 days, 9-11 days, 10-12 days, 11-13 days, 12-14 days, 13-15 days, 14-16 days, between 15-17 days, between 16-18 days, between 17-19 days, between 18-20 days, between 1-4 days, between 2-5 days, between 3-6 days, between 4-7 days, between 5-8 days, between 6-9 days, between 7-10 days, between 8-11 days, between 9-12 days, between 10-13 days, between 11-14 days, between 12-15 days, between 13-16 days, between 14-17 days, between 15-18 days, between 16-19 days, between 17-20 days, between 1-6 days, between 2-7 days, between 3-8 days, between 4-9 days, between 5-10 days, between 6-11 days, between 7-12 days, between 8-13 days, between 9-14 days, between 10-15 days, between 11-16 days, between 12-17 days, between 13-18 days, between 14-19 days, between 15-20 days, between about 5.0 days and about 20 days, between about 5.0 days and about 7.1 days, or between about 5.0 days and about 11.2 days.

In certain embodiments, the half-life of PEGylated C-peptide is between about 5.0 days and about 11.2 days.

In further embodiments, the $AUC_T$ of PEGylated C-peptide is between about 3.1 nM·day and about 85 nM·day, between about 4.3 nM·day and about 67 nM·day, between about 13.8 nM·day and about 41.5 nM·day, between about 3.5 nM·day and about 70 nM·day, between about 3.1 nM·day and about 5.6 nM·day, between about 10 nM·day and about 13 nM·day, between about 12 nM·day and about 17 nM·day, between about 48 nM·day and about 85 nM·day, between about 1 nM·day and about 3 nM·day, between about 3 nM·day and about 5 nM·day, between about 7 nM·day and about 9 nM·day, between about 9 nM·day and about 11 nM·day, between about 11 nM·day and about 13 nM·day, between about 13 nM·day and about 15 nM·day, between about 5 nM·day and about 10 nM·day, between about 10 nM·day and about 15 nM·day, between about 15 nM·day and about 20 nM·day, between about 20 nM·day and about 25 nM·day, between about 5 nM·day and about 15 nM·day, between about 10 nM·day and about 20 nM·day, between about 15 nM·day and about 25 nM·day, between about 20 nM·day and about 30 nM·day, between about 25 nM·day and about 35 nM·day, between about 30 nM·day and about 40 nM·day, between about 35 nM·day and about 45 nM·day, between about 40 nM·day and about 50 nM·day, between about 45 nM·day and about 55 nM·day, between about 50 nM·day and about 60 nM·day, between about 55 nM·day and about 65 nM·day, between about 60 nM·day and about 70 nM·day, between about 65 nM·day and about 75 nM·day, between about 70 nM·day and about 80 nM·day, between about 75 nM·day and about 85 nM·day, between about 5 nM·day and about 25 nM·day, between about 15 nM·day and about 35 nM·day, between about 25 nM·day and about 45 nM·day, between about 35 nM·day and about 55 nM·day, between about 45 nM·day and about 65 nM·day, between about 55 nM·day and about 75 nM·day, or between about 65 nM·day and about 85 nM·day.

In further embodiments, the $AUC_T$ of PEGylated C-peptide is between about 3.1 nM·day and about 85 nM·day.

In further embodiments, the $AUC_T$ of PEGylated C-peptide is between about 4.3 nM·day and about 67 nM·day.

In further embodiments, the $AUC_T$ of PEGylated C-peptide is between about 13.8 nM·day and about 41.5 nM·day.

In further embodiments, the $AUC_T$ of PEGylated C-peptide is about 13.8 nM·day.

In further embodiments, the $AUC_T$ of PEGylated C-peptide is about 41.5 nM·day.

In further embodiments, the volume of distribution of PEGylated C-peptide is between about 5 L and about 30 L, between about 5.8 L and about 22 L, between about 10.4 L and about 22 L, between about 8 L and about 22 L, between about 12 L and about 15 L, between about 5 L and about 10 L, between about 10 L and about 15 L, between about 15 L and about 20 L, between about 20 L and about 25 L, between about 25 L and about 30 L, between about 30 L and about 35 L, between about 5 L and about 15 L, between about 10 L and about 20 L, between about 15 L and about 25 L, between about 20 L and about 30 L, or between about 25 L and about 35 L.

further embodiments, the volume of distribution of PEGylated C-peptide is between about 5.8 L and about 22 L.

In further embodiments, the volume of distribution of PEGylated C-peptide is between about 10.4 L and about 22 L.

In further embodiments, the volume of distribution of PEGylated C-peptide is between about 10 L and about 15 L.

In further embodiments, the clearance of PEGylated C-peptide is between about 0.8 L/day and about 2.2 L/day, between about 0.9 L/day and about 2.2 L/day, between about 1.1 L/day and about 1.6 L/day, between about 1.3 L/day and about 1.7 L/day, between about 0.1 L/day and about 5.0 L/day, between about 0.2 L/day and about 0.6 L/day, between about 0.4 L/day and about 0.8 L/day, between about 0.6 L/day and about 1.0 L/day, between about 0.8 L/day and about 1.2 L/day, between about 1.0 L/day and about 1.4 L/day, between about 1.2 L/day and about 1.6 L/day, between about 1.4 L/day and about 1.8 L/day, between about 1.6 L/day and about 2.0 L/day, between about 1.8 L/day and about 2.2 L/day, between about 2.0 L/day and about 2.4 L/day, between about 2.2 L/day and about 2.6 L/day, between about 2.4 L/day and about 2.8 L/day, between about 2.6 L/day and about 3.0 L/day, between about 0.1 L/day and about 1.0 L/day, between about 0.5 L/day and about 1.5 L/day, between about 1.0 L/day and about 2.0 L/day, between about 1.5 L/day and about 2.5 L/day, between about 2.0 L/day and about 3.0 L/day, between about 2.5 L/day and about 3.5 L/day, or between about 3.0 L/day and about 4.0 L/day.

In further embodiments, the clearance of PEGylated C-peptide is between about 0.8 L/day and about 2.2 L/day.

In further embodiments, the clearance of PEGylated C-peptide is between about 1.1 L/day and about 1.6 L/day.

In further embodiments, at least one of $C_{avg}$, $C_{min}$, $C_{max}$, or $AUC_T$ is dose proportional within the range of 0.3 mg to 3.3 mg.

In further embodiments, the amount of PEGylated C-peptide administered is between about 0.25 mg and about 0.50 mg, between about 0.5 mg and about 1.0 mg, between about 1.0 mg and about 1.5 mg, between about 1.5 mg and about 2.0 mg, between about 2.0 mg and about 3.0 mg, between about 3.0 mg and about 4.0 mg, between about 4.0 mg and about 5.0 mg, between about 3.0 mg and about 5.0 mg, or between about 5.0 mg and about 10.0 mg.

In certain embodiments, PEGylated C-peptide is first administered as a loading dose and thereafter a maintenance dose is administered.

In certain embodiments, the PEGylated C-peptide is administered every 7 days.

In further embodiments, the PEGylated C-peptide is CBX129801.

In further embodiments, the amount of CBX129801 administered is between about 0.3 milligrams to about 3.3 milligrams every 7 days.

In further embodiments, the amount of CBX129801 administered is about 0.3 milligrams every 7 days.

In further embodiments, the amount of CBX129801 administered is about 1 milligram every 7 days.

In further embodiments, the amount of CBX129801 administered is about 0.8 milligrams every 7 days.

In further embodiments, the amount of CBX129801 administered is about 2.4 milligrams every 7 days.

In further embodiments, the amount of CBX129801 administered is about 3.3 milligrams every 7 days.

In further embodiments, a loading dose of 1.6 milligrams of CBX129801 is administered on the first day, followed by a maintenance dose of about 0.8 milligrams of CBX129801 every 7 days.

In further embodiments, a loading dose of 1.8 milligrams of CBX129801 is administered on the first day, followed by a maintenance dose of about 0.8 milligrams of CBX129801 every 7 days.

In further embodiments, a loading dose of 2 milligrams of CBX129801 is administered on the first day, followed by a maintenance dose of about 0.8 milligrams of CBX129801 every 7 days.

In further embodiments, a loading dose of 2.4 milligrams of CBX129801 is administered on the first day, followed by a maintenance dose of about 0.8 milligrams of CBX129801 every 7 days.

In further embodiments, the amount of CBX129801 administered is about 2.4 milligrams every 14 days.

In further embodiments, a loading dose of 3.3 milligrams of CBX129801 is administered on the first day, followed by a maintenance dose of about 2.5 milligrams of CBX129801 every 14 days.

In further embodiments, the amount of CBX129801 administered is about 3.3 milligrams every 14 days.

In further embodiments, the amount of CBX129801 administered is about 12.5 milligrams every 30 days.

In further embodiments, steady-state plasma concentrations of PEGylated C-peptide are achieved after repeat dosing within about 3 days of dosing, within about 4 days of dosing, within about 5 days of dosing, within about 6 days of dosing, within about 7 days of dosing, within about 8 days of dosing, within about 9 days of dosing, within about 10 days of dosing, within about 11 days of dosing, within about 12 days of dosing, within about 13 days of dosing, within about 14 days of dosing, within about 15 days of dosing, within about 16 days of dosing, within about 17 days of dosing, within about 18 days of dosing, within about 19 days of dosing, within about 20 days of dosing, within about 21 days of dosing, within about 22 days of dosing, within about 23 days of dosing, within about 24 days of dosing, within about 25 days of dosing, within about 26 days of dosing, within about 27 days of dosing, within about 28 days of dosing, within about 29 days of dosing, within about 30 days of dosing, within about 31 days of dosing, within about 32 days of dosing, within about 33 days of dosing, within about 34 days of dosing, within about 35 days of dosing, within about 36 days of dosing, within about 37 days of dosing, within about 38 days of dosing, within about 39 days of dosing, or within about 40 days of dosing.

In further embodiments, steady state plasma concentrations of PEGylated C-peptide are achieved within about 3 days of repeat dosing.

In further embodiments, steady state plasma concentrations of PEGylated C-peptide are achieved within about 40 days of repeat dosing.

In further embodiments, C-peptide levels are maintained above the minimum effective therapeutic level.

In certain aspects of any of the claimed PEGylated C-peptides, the PEGylated C-peptide has an equi-potent biological activity with the unmodified C-peptide. In certain aspects of any of the claimed PEGylated C-peptides, the PEGylated C-peptide retains at least about 95% of the biological activity of the unmodified C-peptide. In certain aspects of any of the claimed PEGylated C-peptides, the PEGylated C-peptide retains at least about 90% of the biological activity of the unmodified C-peptide. In certain aspects of any of the claimed PEGylated C-peptides, the PEGylated C-peptide retains at least about 80% of the biological activity of the unmodified C-peptide. In another aspect of any of the claimed PEGylated C-peptides, the PEGylated C-peptide retains at least about 70% of the biological activity of the unmodified C-peptide. In another aspect of any of the claimed PEGylated C-peptides, the PEGylated C-peptide retains at least about 60% of the biological activity of the unmodified C-peptide. In another aspect of any of the claimed PEGylated C-peptides, the PEGylated C-peptide retains at least about 50% of the biological activity of the unmodified C-peptide. In another aspect of any of the claimed PEGylated C-peptides, the PEGylated C-peptide retains at least about 40% of the biological activity of the unmodified C-peptide. In another aspect of any of the claimed PEGylated C-peptides, the PEGylated C-peptide retains at least about 30% of the biological activity of the unmodified C-peptide. In another aspect of any of the claimed PEGylated C-peptides, the PEGylated C-peptide retains at least about 20% of the biological activity of the unmodified C-peptide. In another aspect of any of the claimed PEGylated C-peptides, the PEGylated C-peptide retains at least about 10% of the biological activity of the unmodified C-peptide. In another aspect of any of the claimed PEGylated C-peptides, the PEGylated C-peptide retains at least about 5% of the biological activity of the unmodified C-peptide.

In another embodiment, the present invention includes a method for maintaining C-peptide levels above the minimum effective therapeutic level in a patient in need thereof, comprising administering to the patient a therapeutic dose of any of the claimed PEGylated C-peptides.

In another aspect of any of the claimed PEGylated C-peptides, the PEGylated C-peptide is substantially free of adverse side effects when subcutaneously administered to a mammal at an effective therapeutic dose.

In another embodiment, the present invention includes a method for treating one or more long-term complications of diabetes in a patient in need thereof, comprising administering to the patient a therapeutic dose of any of the claimed PEGylated C-peptides.

In another embodiment, the present invention includes a method for treating an insulin-requiring patient comprising administering to the patient a therapeutic dose of PEGylated C-peptide of any of the claimed PEGylated C-peptides in combination with insulin.

In certain embodiments, insulin-requiring patients have diabetes.

In one aspect of any of these methods, the PEGylated C-peptide is administered with a dosing interval of about 1 day or longer. In one aspect of any of these methods, the PEGylated C-peptide is administered with a dosing interval of about 3 days or longer. In one aspect of any of these methods, the PEGylated C-peptide is administered with a dosing interval of about 4 days or longer. In one aspect of any of these methods, the PEGylated C-peptide is administered with a dosing interval of about 5 days or longer. In one aspect of any of these methods, the PEGylated C-peptide is administered with a dosing interval of about 6 days or longer. In one aspect of any of these methods, the PEGylated C-peptide is administered with a dosing interval of about 7 days or longer. In one aspect of any of these methods, the PEGylated C-peptide is administered with a dosing interval of about 10 days or longer. In one aspect of any of these methods, the PEGylated C-peptide is administered with a dosing interval of about 14 days or longer. In one aspect of any of these methods, the PEGylated C-peptide is administered with a dosing interval of about 17 days or longer. In one aspect of any of these methods, the PEGylated C-peptide is administered with a dosing interval of about 21 days or longer.

In another aspect of any of these methods, the therapeutic dose of PEGylated C-peptide is administered subcutaneously. In another aspect of any of these methods, the therapeutic dose of PEGylated C-peptide is administered orally.

In another embodiment, the present invention includes the use of any of the claimed PEGylated C-peptides as a C-peptide replacement therapy in a patient in need thereof.

In another embodiment, the present invention includes the use of any of the claimed PEGylated C-peptides for treating one or more long-term complications of insulin-requiring diabetes in a patient in need thereof. In certain embodiments, the long-term complications of diabetes are selected from the group consisting of microvascular disease, macrovascular disease, retinopathy, peripheral neuropathy, autonomic neuropathy, and nephropathy. In certain embodiments, the long-term complication of insulin-requiring diabetes is peripheral neuropathy. In certain embodiments, the peripheral neuropathy is established peripheral neuropathy. In certain embodiments, treatment results in an improvement of at least 1 m/s in nerve conduction velocity compared to nerve conduction velocity prior to starting PEGylated C-peptide therapy.

In certain embodiments, the dose of PEGylated C-peptide required to achieve a therapeutically effective concentration is less than $\frac{1}{2}$ of a comparatively effective dose of C-peptide. In further embodiments, the dose of PEGylated C-peptide required to achieve a therapeutically effective concentration is less than $\frac{1}{5}$ of a comparatively effective dose of C-peptide. In further embodiments, the dose of PEGylated C-peptide required to achieve a therapeutically effective concentration is less than $\frac{1}{10}$ of a comparatively effective dose of C-peptide. In further embodiments, the dose of PEGylated C-peptide required to achieve a therapeutically effective concentration is less than $\frac{1}{20}$ of a comparatively effective dose of C-peptide. In further embodiments, the dose of PEGylated C-peptide required to achieve a therapeutically effective concentration is less than $\frac{1}{40}$ of a comparatively effective dose of C-peptide. In further embodiments, the dose of PEGylated C-peptide required to achieve a therapeutically effective concentration is less than $\frac{1}{60}$ of a comparatively effective dose of C-peptide. In further embodiments, the dose of PEGylated C-peptide required to achieve a therapeutically effective concentration is less than $\frac{1}{80}$ of a comparatively effective dose of C-peptide. In further embodiments, the dose of PEGylated C-peptide required to achieve a therapeutically effective concentration is less than $\frac{1}{100}$ of a comparatively effective dose of C-peptide. In further embodiments, the dose of PEGylated C-peptide required to achieve a therapeutically effective concentration is less than $\frac{1}{120}$ of a comparatively effective dose of C-peptide. In further embodiments, the dose of PEGylated C-peptide required to achieve a therapeutically effective concentration is less than $\frac{1}{140}$ of a comparatively effective dose of C-peptide. In further embodiments, the dose of PEGylated C-peptide required to achieve a therapeutically effective concentration is less than $\frac{1}{160}$ of a comparatively effective dose of C-peptide.

In another embodiment, the present invention includes a pharmaceutical composition comprising any of the claimed PEGylated C-peptides and a pharmaceutically acceptable carrier or excipient. In certain embodiments, the pharmaceutically acceptable carrier or excipient is sorbitol. In certain embodiments, the sorbitol is present at a concentration of about 2% to about 8% wt/wt. In certain embodiments, the sorbitol is present at a concentration of about 4.7%. In certain embodiments, the pharmaceutical composition is buffered to a pH within the range of about pH 5.5 to about pH 6.5. In certain embodiments, the pharmaceutical composition is buffered to a pH of about 6.0. In certain embodiments, the pharmaceutical composition is buffered with a phosphate buffer at a concentration of about 5 mM to about 25 mM. In certain embodiments, the pharmaceutical composition is buffered with a phosphate buffer at a concentration of about 10 mM. In one aspect of any of these embodiments, the pharmaceutical composition is characterized by improved stability of any of the claimed PEGylated C-peptides compared to a pharmaceutical composition comprising the same PEGylated C-peptide and 0.9% saline at pH 7.0, wherein the stability is determined after incubation for a predetermined time at 40° C. In different embodiments, the pre-determined time is about one week, about 2 weeks, about 3 weeks, about 4 weeks, or about 5 weeks, or about 6 weeks.

In another embodiment, the present invention includes a pharmaceutical composition comprising any of the claimed PEGylated C-peptides and insulin.

Certain embodiments include the use of any of the disclosed PEGylated C-peptides to reduce the risk of hypoglycemia in an insulin-requiring patient, in a regimen which additionally comprises the administration of insulin, comprising; a) administering insulin to the patient; b) administering a therapeutic dose of the PEGylated C-peptide in a different site as that used for the patient's insulin administration; c) adjusting the dosage amount, type, or frequency of insulin administered based on the patient's altered insulin requirements resulting from the therapeutic dose of the PEGylated C-peptide.

In some embodiments, the patient has at least one long-term complication of diabetes.

Certain embodiments include a method for treating an insulin-requiring human patient, comprising the steps of; a) administering insulin to the patient, wherein the patient has neuropathy; b) administering subcutaneously to the patient a therapeutic dose of any of the disclosed PEGylated C-peptides in a different site as that used for the patient's insulin administration; c) adjusting the dosage amount, type, or frequency of insulin administered based on monitoring the patient's altered insulin requirements resulting from the therapeutic dose of PEGylated C-peptide, wherein the adjusted dose of insulin reduces the risk, incidence, or severity of hypoglycemia, wherein the adjusted dose of insulin is at least 10% less than the patient's insulin dose prior to starting PEGylated C-peptide treatment.

Certain embodiments include a method of reducing insulin usage in an insulin-requiring human patient, comprising the steps of; a) administering insulin to the patient; b) administering subcutaneously to the patient a therapeutic dose any of the disclosed PEGylated C-peptides in a different site as that used for the patient's insulin administration; c) adjusting the dosage amount, type, or frequency of insulin administered based on monitoring the patient's altered insulin requirements resulting from the therapeutic dose of PEGylated C-peptide, wherein the adjusted dose of insulin does not induce hypoglycemia, wherein the adjusted dose of insulin is at least 10% less than the patient's insulin dose prior to starting the PEGylated C-peptide treatment.

BRIEF DESCRIPTION OF THE DRAWINGS

A better understanding of the features and advantages of the present invention can be obtained by reference to the following detailed description that sets forth illustrative embodiments, in which the principles of the invention are utilized, and the accompanying drawings of which.

DETAILED DESCRIPTION OF THE INVENTION

Definitions

Figure 1:
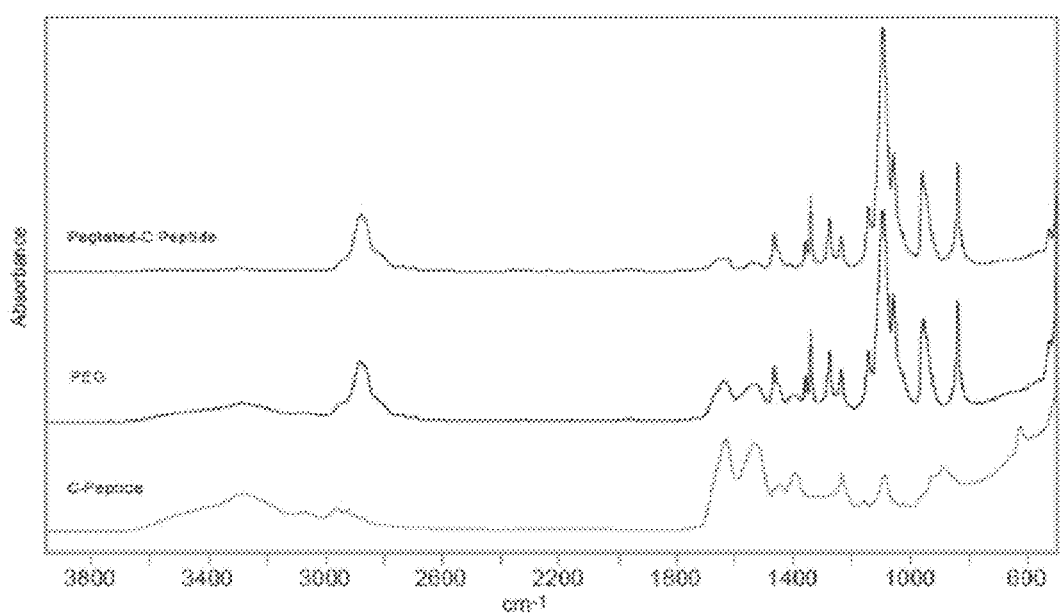
FIG. 1 shows a Fourier Transform Infrared Spectroscopy (FT-IR): of C-peptide, the PEG reagent, and PEGylated C-peptide.

The term "active" or "activated" when used in conjunction with a particular functional group refers to a reactive functional group that reacts readily with an electrophile or a nucleophile on another molecule. This is in contrast to those groups that require strong catalysts or highly impractical reaction conditions in order to react (i.e., a "non-reactive" or "inert" group). As used herein, the term "functional group" or any synonym thereof is meant to encompass protected forms thereof as well as unprotected forms.

The term "alkoxy" refers to an —O—R group, wherein R is alkyl or substituted alkyl, preferably C1-6 alkoxy (e.g., methoxy, ethoxy, propyloxy, and so forth).

The term "alkyl" refers to a hydrocarbon, typically ranging from about 1 to 12 atoms in length. Hydrocarbons may be branched or linear and are preferably, but not necessarily saturated. Exemplary alkyl groups include methyl, ethyl, propyl, butyl, pentyl, 2-methylbutyl, 2-ethylpropyl, etc. As used herein "alkyl" includes cycloalkyl as well as cycloalkylene alkyls. The term "lower alkyl" refers to an alkyl group containing from 1 to 6 carbon atoms, and may be straight chain or branched.

The term "compartmental pharmacokinetic analysis" as used herein is the method of estimating pharmacokinetic parameters assuming a pharmacokinetic model.

The term "non-compartmental pharmacokinetic analysis" as used herein is the method of calculating pharmacokinetic parameters without assumptions for the pharmacokinetic model.

The term "$C_{max}$" as used herein is the maximum serum or plasma concentration of drug after dosing.

The term "$C_{min}$" as used herein is the observed minimum plasma concentration after repeat dosing.

The term "$C_{ave}$" as used herein is the average plasma concentration calculated from $AUC_\tau$ divided by the dosing interval.

The term "$T_{max}$" as used herein is the time to reach $C_{max}$.

The term "half-life" or "$t_{1/2}$" as used herein is terminal half-life calculated by ln(2) divided by λ, where λ is the rate constant for the log-linear portion of the terminal phase. A minimum of three values in the post-distribution phase of the plasma concentration-time curve are required for calculation of λ and the $R^2$ (correlation fit for the regression line after adjusted for the number of included data) value is ≥0.75.

The term "$T_{lag}$" or "lag time" as used herein is the time delay between drug administration and first observed concentration above the limit of quantification in plasma (from the observed plasma concentration time data).

The term "AUC" as used herein means "area under curve" for the serum or plasma concentration-time curve, as calculated by the trapezoidal rule over the complete sample collection interval.

The term "$AUC_{last}$" as used herein is the area under the plasma concentration-time curve from time zero to the last measurable plasma concentration ($C_T$) using the linear trapezoidal rule. It is calculated as the sum of the areas from time zero to the time of the last quantifiable plasma concentration ($C_T$).

The term "$AUC_\tau$" or "$AUC_{tau}$" as used herein is the area under the plasma concentration-time curve over a dosing interval and is calculated using the linear trapezoidal rule.

The term "$AUC_\infty$" or "$AUC_{inf}$" as used herein is the area under the plasma concentration-time curve from time zero to infinity. It is calculated as the sum of the area from time zero to the time of the last quantifiable plasma concentration ($C_T$) and the area from T to infinity, calculated as the last quantifiable plasma concentration divided by λ, where λ is the terminal elimination rate constant as follows:

$$AUC_\infty = AUC_\tau + \frac{C_T}{\lambda}$$

The term "%$AUC_{extrap}$" as used herein is the AUC extrapolated from calculated from $(AUC_\infty - AUC_{last})/AUC_\infty * 100$ The term "CL/F" as used herein is apparent systemic clearance after SC injection. It is determined in the non-compartmental analysis by dividing the total dose by $AUC_\infty$ for a single dose or total dose by $AUC_T$ at steady-state. In the compartment analysis CL/F is a fitted parameter in the pharmacokinetic model.

The term "$V_z/F$" as used herein is the apparent volume of distribution based on the terminal phase after SC injection. It is determined in the non-compartmental analysis by dividing Cl/F by λ.

The term "$V_c/F$" as used herein is the apparent volume of distribution of the central compartment. It is a fitted parameter in the pharmacokinetic compartment analysis.

The term "$DNC_{min}$", "dose-normalized $C_{min}$", "dose-normalized minimum concentration" or "dose-normalized minimum plasma concentration" as used herein is the dose-normalized observed minimum plasma concentration after repeat dosing. It is determined by dividing $C_{min}$ by the dosage weight.

The term "$DNAUC_\tau$", "dose-normalized $AUC_\tau$" or "dose-normalized $AUC_{tau}$" as used herein is the dose-normalized area under the plasma concentration-time curve over a dosing interval. It is determined by dividing $AUC_\tau$ by the dosage weight.

The term "$DNC_{max}$", "dose-normalized $C_{max}$", "dose-normalized maximum concentration", or "dose-normalized maximum plasma concentration" as used herein is the dose-normalized observed maximum plasma concentration after repeat dosing. It is determined by dividing $C_{max}$ by the dosage weight.

The term "D1" as used herein refers to the duration of input of drug from the site of subcutaneous injection into systemic circulation. The dose divided by D1 describes the zero order rate constant for drug input into the circulation.

The term "LD" as used herein is the loading dose, a dose greater than the maintenance dose given at the beginning of a course of treatment to more quickly achieve a desired plasma concentration and a faster onset of effect.

The term "MD" as used herein is the maintenance dose and frequency administered to maintain a desired plasma concentration or therapeutic effect.

The term "% CV" as used herein is the percent coefficient of variation.

The term "bioavailability" refers to the amount of drug that reaches the circulation expressed as the percent compared to that achieved with an intravenous dose. Bioavailability is often referred to in terms of % bioavailability, which is the bioavailability achieved for a drug (such as C-peptide) following administration of a sustained release composition of that drug divided by the bioavailability achieved for the drug following intravenous administration of the same equivalent dose of the drug, multiplied by 100.

The phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz G E and R H Schirmer, *Principles of Protein Structure*, Springer-Verlag (1979)). According to such analyses, groups of amino acids can be defined where amino acids within a group exchange preferentially with each other, and therefore resemble each other most in their impact on the overall protein structure (Schulz G E and R H Schirmer, *Principles of Protein Structure*, Springer-Verlag (1979)).

Examples of amino acid groups defined in this manner include: a "charged/polar group," consisting of Glu, Asp, Asn, Gln, Lys, Arg, and His; an "aromatic or cyclic group," consisting of Pro, Phe, Tyr, and Trp; and an "aliphatic group," consisting of Gly, Ala, Val, Leu, Ile, Met, Ser, Thr, and Cys.

Within each group, subgroups can also be identified, e.g., the group of charged/polar amino acids can be sub-divided into the subgroups consisting of the "positively-charged subgroup," consisting of Lys, Arg, and His; the "negatively-charged subgroup," consisting of Glu and Asp, and the "polar subgroup" consisting of Asn and Gln. The aromatic or cyclic group can be sub-divided into the subgroups consisting of the "nitrogen ring subgroup," consisting of Pro, His, and Trp; and the "phenyl subgroup" consisting of Phe and Tyr. The aliphatic group can be sub-divided into the subgroups consisting of the "large aliphatic non-polar subgroup," consisting of Val, Leu, and Ile; the "aliphatic slightly-polar subgroup," consisting of Met, Ser, Thr, and Cys; and the "small-residue subgroup," consisting of Gly and Ala.

Examples of conservative mutations include amino acid substitutions of amino acids within the subgroups above, e.g., Lys for Arg and vice versa such that a positive charge can be maintained; Glu for Asp and vice versa such that a negative charge can be maintained; Ser for Thr such that a free —OH can be maintained; and Gln for Asn such that a free —NH$_2$ can be maintained. "Semi-conservative mutations" include amino acid substitutions of amino acids with the same groups listed above, which do not share the same subgroup. For example, the mutation of Asp for Asn, or Asn for Lys, all involve amino acids within the same group, but different subgroups. "Non-conservative mutations" involve amino acid substitutions between different groups, e.g., Lys for Leu, Phe for Ser.

The terms "Dalton", "Da", or "D" refers to an arbitrary unit of mass, being 1/12 the mass of the nuclide of carbon-12, equivalent to $1.657 \times 10^{-24}$ g. The term "kDa" is for kilodalton (i.e., 1000 Daltons).

The terms "diabetes", "diabetes mellitus", or "diabetic condition", unless specifically designated otherwise, encompass all forms of diabetes as well as patients who lack a functioning pancreas due to surgical removal, congenital defect, damage, or physical injury. The term "type 1 diabetic patient" or "type 1 diabetes" refers to a patient with a fasting plasma glucose concentration of greater than about 7.0 mmoL/L and a fasting C-peptide level of about, or less than about 0.2 nmoL/L. The term "type 2 diabetic patient" or "type 2 diabetes" generally refers to a patient with a fasting plasma glucose concentration of greater than about 7.0 mmoL/L and fasting C-peptide level during early stages that is within or higher than the normal physiological range of C-peptide levels (about 0.47 to 2.5 nmoL/L). It will be appreciated that a patient initially diagnosed with type 2 diabetes may subsequently develop insulin-requiring diabetes, but will remain diagnosed as a type 2 patient, even though his/her C-peptide levels drop to <0.2 nmol/L.

The terms "insulin-requiring patient" or "insulin-requiring diabetes" encompass all forms of diabetics/diabetes who/that require insulin administration to adequately maintain normal glucose levels unless specified otherwise.

Diabetes is usually diagnosed by measuring fasting blood glucose, and sometimes by glycated hemoglobin levels (which are typically referred to as hemoglobin A1c or $Hb_{A1c}$). Normal fasting adult glucose levels are 70-99 mg/dL. Normal HbA1c levels are generally less than 6%. The World Health Organization defines the diagnostic value of fasting plasma glucose concentration as 7.0 mmoL/L (126 mg/dL) and above for diabetes mellitus, or 2-hour postprandial glucose level greater than or equal to 11.1 mmoL/L (greater than or equal to 200 mg/dL). Other values suggestive of or indicating high risk for diabetes mellitus include elevated arterial pressure greater than or equal to 140/90 mm Hg; elevated plasma triglycerides (greater than or equal to 1.7 mmoL/L [150 mg/dL]) and/or low HDL-cholesterol (less than 0.9 mmoL/L [35 mg/dL] for men; and less than 1.0 mmoL/L [39 mg/dL] for women); central obesity (BMI exceeding 30 kg/m$^2$); microalbuminuria, where the urinary albumin excretion rate is greater than or equal to 20 μg/min or the albumin creatinine ratio is greater than or equal to 30 mg/g.

The term "delivery agent" refers to carrier compounds or carrier molecules that are effective in the oral delivery of therapeutic agents, and may be used interchangeably with "carrier."

The term "homology" describes a mathematically-based comparison of sequence similarities which is used to identify genes or proteins with similar functions or motifs. The nucleic acid and protein sequences of the present invention can be used as a "query sequence" to perform a search against public databases to, e.g., identify other family members, related sequences, or homologs. Such searches can be performed using the NBLAST and XBLAST programs (version 2.0) of Altschul et al.: *J. Mol. Biol.* 215: 403-410, (1990). BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al.: *Nucleic Acids Res.* 25(17): 3389-3402, (1997). When utilizing BLAST and Gapped BLAST programs, the default parameters of the respective programs (e.g., XBLAST and BLAST) can be used.

The term "homologous" refers to the relationship between two proteins that possess a "common evolutionary origin", including proteins from superfamilies (e.g., the immunoglobulin superfamily) in the same species of animal, as well as homologous proteins from different species of animal (e.g., myosin light chain polypeptide; see Reeck et al.: *Cell* 50: 667, (1987)). Such proteins (and their encoding nucleic acids) have sequence homology, as reflected by their sequence similarity, whether in terms of percent identity or by the presence of specific residues or motifs and conserved positions. In specific embodiments, two nucleic acid sequences are "substantially homologous" or "substantially similar" when at least about 85%, and more preferably at least about 90 or at least about 95% of the nucleotides match over a defined length of the nucleic acid sequences, as determined by a sequence comparison algorithm known such as BLAST, FASTA, DNA Strider, CLUSTAL, etc. An example of such a sequence is an allelic or species variant of the specific genes of the present invention. Sequences that are substantially homologous may also be identified by hybridization, e.g., in a Southern hybridization experiment under, e.g., stringent conditions as defined for that particular system.

Similarly, in particular embodiments of the invention, two amino acid sequences are "substantially homologous" or "substantially similar" when greater than 80% of the amino acid residues are identical, or when greater than about 90% of the amino acid residues are similar (i.e., are functionally identical). Preferably the similar or homologous polypeptide sequences are identified by alignment using, e.g., the GCG (Genetics Computer Group, version 7, Madison, Wis.) pileup program, or using any of the programs and algorithms described above. The program may use the local homology algorithm of Smith and Waterman with the default values: gap creation penalty=$-(1+\frac{1}{3}k)$, k being the gap extension number, average match=1, average mismatch=$-0.333$.

As used herein, "identity" means the percentage of identical nucleotide or amino acid residues at corresponding positions in two or more sequences when the sequences are aligned to maximize sequence matching, i.e., taking into account gaps and insertions. Identity can be readily calculated by known methods, including but not limited to those described in *Computational Molecular Biology*, Lesk A M, Ed., Oxford University Press, New York, (1988); *Biocomputing: Informatics and Genome Projects*, Smith D W, Ed., Academic Press, New York, (1993); *Computer Analysis of Sequence Data, Part I*, Griffin A M and Griffin H G, Eds., Humana Press, New Jersey, (1994); *Sequence Analysis in Molecular Biology*, von Heinje G, Academic Press, (1987); and *Sequence Analysis Primer*, Gribskov M and Devereux J, Eds., M Stockton Press, New York, (1991); and Carillo H and Lipman D, *SIAM J. Applied Math.*, 48: 1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux J et al.: *Nucleic Acids Res.* 12(1): 387, (1984)), BLASTP, BLASTN, and FASTA (Altschul S F et al.: *J. Molec. Biol.* 215: 403-410, (1990) and Altschul S F et al.: *Nucleic Acids Res.* 25: 3389-3402, (1997)). The BLAST X program is publicly available from NCBI and other sources (BLAST Manual, Altschul S F et al., NCBI NLM NIH Bethesda, Md. 20894; Altschul S F et al., *J. Mol. Biol.* 215: 403-410, (1990)). The well-known Smith Waterman algorithm (Smith T F, Waterman M S: *J. Mol. Biol.* 147(1): 195-197, (1981)) can also be used to determine similarity between sequences.

The term "insulin" includes all forms and analogs of insulin including, without limitation, rapid-acting forms, such as Insulin Lispro rDNA origin: HUMALOG (1.5 mL, 10 mL, Eli Lilly and Company, Indianapolis, Ind.), Insulin Injection (Regular Insulin) from beef and pork (regular ILETIN I, Eli Lilly), human: rDNA: HUMULIN R (Eli Lilly), NOVOLIN R (Novo Nordisk, New York, N.Y.), Semi synthetic: VELOSULIN Human (Novo Nordisk), rDNA Human, Buffered: VELOSULIN BR, pork: regular Insulin (Novo Nordisk), purified pork: Pork Regular ILETIN II (Eli Lilly), Regular Purified Pork Insulin (Novo Nordisk), and Regular (Concentrated) ILETIN II U-500 (500 units/mL, Eli Lilly); intermediate-acting forms such as Insulin Zinc Suspension, beef and pork: LENTE ILETIN G I (Eli Lilly), Human, rDNA: HUMULIN L (Eli Lilly), NOVOLIN L (Novo Nordisk), purified pork: LENTE ILETIN II (Eli Lilly), Isophane Insulin Suspension (NPH): beef and pork: NPH ILETIN I (Eli Lilly), Human, rDNA: HUMULIN N (Eli Lilly), Novolin N (Novo Nordisk), purified pork: Pork NPH Eetin II (Eli Lilly), NPH-N (Novo Nordisk); and long-acting forms such as Insulin zinc suspension, extended (ULTRALENTE, Eli Lilly), human, rDNA: HUMULIN U (Eli Lilly). Insulin analogs include, without limitation, Humalog (lispro), Novolog (aspart), Levemir (detemir), Lantus (glargine), and Apidra (glulisine), and mixtures thereof.

The terms "measuring" or "measurement" mean assessing the presence, absence, quantity, or amount (which can be an effective amount) of either a given substance within a clinical- or patient-derived sample, including the derivation of qualitative or quantitative concentration levels of such substances, or otherwise evaluating the values or categorization of a patient's clinical parameters.

The term "meal" as used herein means a standard and/or a mixed meal.

The term "mean", when preceding a pharmacokinetic value (e.g., mean $t_{max}$), represents the arithmetic mean value of the pharmacokinetic value unless otherwise specified.

The term "mean baseline level" as used herein means the measurement, calculation, or level of a certain value that is used as a basis for comparison, which is the mean value over a statistically significant number of subjects, e.g., across a single clinical study or a combination of more than one clinical study.

The term "multiple dose" means that the patient has received at least two doses of the drug composition in accordance with the dosing interval for that composition.

The terms "NCV" or "nerve conduction velocity" refers to the speed at which an electrochemical signal propagates down a neural pathway. Nerve conduction velocity can vary with axon diameter, myelination, the internal resistance of the axon, and temperature. Nerve conduction velocity differs from species to species, and to a lesser degree, from individual to individual.

The term "neuropathy" in the context of a "patient with neuropathy" or a patient that "has neuropathy", means that the patient meets at least one of the four criteria outlined in England et al. (Distal symmetric polyneuropathy: A definition for clinical research: Report of the American Academy of Neurology, the American Association of Electrodiagnostic Medicine, and the American Academy of Physical Medicine and Rehabilitation, *Neurology,* 2005, 64, 199-207), which in brief include 1) clinical signs of polyneuropathy, 2) symptoms of nerve dysfunction, 3) nerve conduction deficits in at least two nerves, or 4) quantitative sensory deficits. The term "established neuropathy" means that the patient meets at least two of the four criteria outlined in the San Antonio Conference on diabetic neuropathy. The term "incipient or subclinical neuropathy" refers to a patient that exhibits only nerve conduction deficits, and no other symptoms of neuropathy.

The term "normal glucose levels" is used interchangeably with the term "normoglycemic" and "normal" and refers to a fasting venous plasma glucose concentration of less than about 5.6 mmoL/L (100 mg/dL). Sustained glucose levels above normoglycemic levels (but below diabetic levels) are considered a pre-diabetic condition and referred to as impaired glucose tolerance (or a patient with glucose intolerance).

As used herein, the term "patient" in the context of the present invention is preferably a mammal. The mammal can be a human, non-human primate, mouse, rat, dog, cat, horse, or cow, but are not limited to these examples. Mammals other than humans can be advantageously used as patients that represent animal models of insulin-requiring diabetes mellitus, or diabetic conditions. A patient can be male or female. A patient can be one who has been previously diagnosed or identified as having insulin-requiring diabetes, or a diabetic condition, and optionally has already undergone, or is undergoing, a therapeutic intervention for the diabetes. A patient can also be one who is suffering from a long-term complication of diabetes. Preferably the patient is human.

The terms "PEG", "polyethylene glycol", or "poly(ethylene glycol)" as used herein refers to any water soluble poly (ethylene oxide), and includes molecules comprising the structure —$(CH_2CH_2O)_n$— where n is an integer from 2 to about 800. A commonly used PEG is end-capped PEG, wherein one end of the PEG is capped with a relatively inactive group such as an alkoxy while the other end is a hydroxyl group that may be further modified. An often used capping group is methoxy, and the corresponding end-capped PEG is often denoted mPEG. The notion PEG is often used instead of mPEG. Specific PEG forms of the invention are branched, linear, forked PEGs, and the like and the PEG groups are typically polydisperse, possessing a low polydispersity index of less than about 1.05. The PEG moieties of the invention will for a given molecular weight will typically consist of a range of ethylene glycol (or ethyleneoxide) monomers. For example, a PEG moiety of molecular weight 2000 Da will typically consist of 43±10 monomers, the average being around 43 monomers. The term "PEGylated" refers to the covalent attachment of PEG to another molecule, such as C-peptide.

The term "replacement dose" in the context of a replacement therapy for C-peptide refers to a dose of C-peptide or PEGylated C-peptide that maintains C-peptide or PEGylated C-peptide levels in the blood within a desirable range, particularly at a level which is at or above the minimum effective therapeutic blood concentration. In certain embodiments, the minimum effective therapeutic concentration is a level which is within the normal physiologic range observed in healthy nondiabetic subjects. In certain aspects, the replacement dose maintains the average steady-state concentration C-peptide or PEGylated C-peptide levels above a minimum level of about 0.1 nM between dosing intervals. In certain aspects, the replacement dose maintains the average steady-state concentration C-peptide or PEGylated C-peptide levels above a minimum level of about 0.2 nM between dosing intervals. In certain aspects, the replacement dose maintains the average steady-state concentration C-peptide or PEGylated C-peptide levels above a minimum level of about 0.4 nM between dosing intervals. In certain aspects, the replacement dose maintains the average steady-state concentration C-peptide or PEGylated C-peptide levels above a minimum level of about 0.6 nM between dosing intervals. In certain aspects, the replacement dose maintains the average steady-state concentration C-peptide or PEGylated C-peptide levels above a minimum level of about 0.8 nM between dosing intervals. In certain aspects, the replacement dose maintains the average steady-state concentration C-peptide or PEGylated C-peptide levels above a minimum level of about 1.0 nM between dosing intervals. In certain aspects, the replacement dose maintains the average steady-state concentration C-peptide or PEGylated C-peptide levels above a minimum level of about 1.2 nM between dosing intervals. In certain aspects, the replacement dose maintains the average steady-state concentration C-peptide or PEGylated C-peptide levels above a minimum level of about 1.4 nM between dosing intervals. In certain aspects, the replacement dose maintains the average steady-state concentration C-peptide or PEGylated C-peptide levels above a minimum level of about 1.6 nM between dosing intervals. In certain aspects, the replacement dose maintains the average steady-state concentration C-peptide or PEGylated C-peptide levels above a minimum level of about 1.8 nM between dosing intervals. In certain aspects, the replacement dose maintains the average steady-state concentration C-peptide or PEGylated C-peptide levels above a minimum level of about 2.0 nM between dosing intervals. In certain aspects, the replacement dose maintains the average steady-state concentration C-peptide or PEGylated C-peptide levels above a minimum level of about 4.9 nM between dosing intervals.

The terms "subcutaneous" or "subcutaneously" or "S.C." or "s.c." in reference to a mode of administration of insulin or PEGylated C-peptide, refers to a drug that is administered as a bolus injection, or via an implantable device into the area in, or below the subcutis, the layer of skin directly below the dermis and epidermis, collectively referred to as the cutis. Preferred sites for subcutaneous administration and/or implantation include the outer area of the upper arm, just above and below the waist, except the area right around the navel (a 2-inch circle). The upper area of the buttock, just behind the hipbone. The front of the thigh, midway to the outer side, 4 inches below the top of the thigh to 4 inches above the knee.

The term "single dose" means that the patient has received a single dose of the drug composition or that the repeated single doses have been administered with washout periods in between. Unless specifically designated as "single dose" or at "steady-state" the pharmacokinetic parameters disclosed and claimed herein encompass both single-dose and multiple-dose conditions.

The term "sequence similarity" refers to the degree of identity or correspondence between nucleic acid or amino acid sequences that may or may not share a common evolutionary origin (see Reeck et al., supra). However, in common usage and in the present application, the term "homologous", when modified with an adverb such as "highly", may refer to sequence similarity and may or may not relate to a common evolutionary origin.

By "statistically significant", it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

As defined herein, the terms "sustained release", "extended release", or "depot formulation" refers to the release of a drug such as PEGylated C-peptide from the sustained release composition or sustained release device which occurs over a period which is longer than that period during which the drug would be available following direct I.V. or S.C. administration of a single dose of drug. In one aspect, sustained release will be a release that occurs over a period of at least about one to two weeks, about two to four weeks, about one to two months, about two to three months, or about three to six months. In certain aspects, sustained release will be a release that occurs over a period of about six months to about one year. The continuity of release and level of release can be affected by the type of sustained release device (e.g., programmable pump or osmotically-driven pump) or sustained release composition, and type of PEGylated C-peptides used (e.g., monomer ratios, molecular weight, block composition, and varying combinations of polymers), polypeptide loading, and/or selection of excipients to produce the desired effect, as more fully described herein.

Various sustained release profiles can be provided in accordance with any of the methods of the present invention. "Sustained release profile" means a release profile in which less than 50% of the total release of drug that occurs over the course of implantation/insertion or other method of administering the drug in the body occurs within the first 24 hours of administration. In a preferred embodiment of the present invention, the extended release profile is selected from the group consisting of; a) the 50% release point occurring at a time that is between 48 and 72 hours after implantation/insertion or other method of administration; b) the 50% release point occurring at a time that is between 72 and 96 hours after implantation/insertion or other method of administration; c) the 50% release point occurring at a time that is between 96 and 110 hours after implantation/insertion or other method of administration; d) the 50% release point occurring at a time that is between 1 and 2 weeks after implantation/insertion or other method of administration; e) the 50% release point occurring at a time that is between 2 and 4 weeks after implantation/insertion or other method of administration; f) the 50% release point occurring at a time that is between 4 and 8 weeks after implantation/insertion or other method of administration; g) the 50% release point occurring at a time that is between 8 and 16 weeks after implantation/insertion or other method of administration; h) the 50% release point occurring at a time that is between 16 and 52 weeks (1 year) after implantation/insertion or other method of administration; and i) the 50% release point occurring at a time that is between 52 and 104 weeks after implantation/insertion or other method of administration.

Additionally, use of a sustained release composition can reduce the "degree of fluctuation" ("DFL") of the drugs plasma concentration. DFL is a measurement of how much the plasma levels of a drug vary over the course of a dosing interval $[(C_{max}-C_{min})/C_{avg}]$. For simple cases, such as I.V. administration, fluctuation is determined by the relationship between the elimination half-life ($T_{1/2}$) and dosing interval. If the dosing interval is equal to the half-life then the trough concentration is exactly half of the peak concentration, and the degree of fluctuation is 100%. Thus a sustained release composition with a reduced DFL (for the same dosing interval) signifies that the difference in peak and trough plasma levels has been reduced. In certain embodiments, the patients receiving a sustained release composition of PEGylated C-peptide have a DFL of approximately 100%, 90%, 80%, 70%, 60%, 50%, 40%, 30%, 20%, or 10%. In further embodiments, the patients receiving a sustained release composition of PEGylated C-peptide have a DFL from about 36% to about 50%.

The terms "treating" or "treatment" means to relieve, alleviate, delay, reduce, reverse, improve, manage, or prevent at least one symptom of a condition in a patient. The term "treating" may also mean to arrest, delay the onset (i.e., the period prior to clinical manifestation of a disease), and/or reduce the risk of developing or worsening a condition.

As used herein, the terms "therapeutically effective amount", "prophylactically effective amount", or "diagnostically effective amount" is the amount of the drug, e.g., insulin or PEGylated C-peptide, needed to elicit the desired biological response following administration.

The term "unit-dose forms" refers to physically discrete units suitable for human and animal patients and packaged individually as is known in the art. It is contemplated for purposes of the present invention that dosage forms of the present invention comprising therapeutically effective amounts of drug may include one or more unit doses (e.g., tablets, capsules, powders, semisolids [e.g., gelcaps or films], liquids for oral administration, ampoules or vials for injection, loaded syringes) to achieve the therapeutic effect. It is further contemplated for the purposes of the present invention that a preferred embodiment of the dosage form is a subcutaneously injectable dosage form.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per practice in the art. Alternatively, "about" with respect to the compositions can mean plus or minus a range of up to 20%, preferably up to 10%, more preferably up to 5%.

As used herein and in the appended claims, the singular forms "a", "an", and "the" include plural referents unless the context clearly indicates otherwise. Thus, for example, reference to "a molecule" includes one or more of such molecules, "a reagent" includes one or more of such different reagents, reference to "an antibody" includes one or more of such different antibodies, and reference to "the method" includes reference to equivalent steps and methods known to those of ordinary skill in the art that could be modified or substituted for the methods and pharmaceutical compositions described herein.

Unless defined otherwise, all technical and scientific terms used herein have the same meaning as commonly understood by one of ordinary skill in the art to which the invention belongs. The following abbreviations listed in Table B are used in certain sections of the disclosure:

TABLE B

LIST OF ABBREVIATIONS

| | |
|---|---|
| ADA | Anti-drug antibody |
| AUC | Area under the concentration curve |
| Conc. | Concentration |
| CL/F | Apparent clearance uncorrected for bioavailability (F) |
| $CL_{ss}/F$ | Apparent clearance uncorrected for bioavailability (F) at steady state |
| ELISA | Enzyme-linked immunosorbent assay |
| DFL | Degree of fluctuation in pharmacokinetics |
| F | Bioavailability or female |
| $F_{rel}$ | Relative bioavailability |
| GLP | Good Laboratory Practice |
| h | Hours |
| i.v./I.V. | Intravenous |
| kg | Kilogram |
| L | Liter |
| M | Male |
| mg | Milligram |
| mL | Milliliter |
| min | Minutes |
| MTD | Maximum tolerated dose |
| ND | Not determined |
| ng | Nanogram |
| NOEL | No observed effect level |
| nM/nmol/L | Nanomolar |
| nmol | Nanomole |
| QC | Quality control |
| PEG | Polyethylene glycol |
| RIA | Radioimmunoassay |
| s.c./S.C. | Subcutaneous |

TABLE B-continued

LIST OF ABBREVIATIONS

| | |
|---|---|
| SD | Standard deviation |
| Vc/F | Apparent volume of distribution in the central compartment following subcutaneous administration, uncorrected for bioavailability (F) |
| Vd/F | Apparent volume of distribution following subcutaneous administration, uncorrected for bioavailability (F) |
| $Vd_{ss}$/F | Apparent volume of distribution at steady state following subcutaneous administration, uncorrected for bioavailability (F) |
| wk | Week |
| U | Units |
| ULN | Upper limit of normal |
| MD | Maintenance dose |
| LD | Loading dose |
| Tau | Dosing Interval |
| $DNC_{min}$ | Dose-normalized observed minimum plasma concentration after repeat dosing |
| $DNAUC_\tau$ | Dose-normalized area under the plasma concentration-time curve over a dosing interval |
| $DNC_{max}$ | Dose-normalized observed maximum plasma concentration after repeat dosing |

Although any methods, compositions, reagents, cells, similar or equivalent to those described herein can be used in the practice or testing of the invention, the preferred methods and materials are described herein.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; D. M. J. Lilley and J. E. Dahlberg, 1992, *Methods of Enzymology: DNA Structure Part A: Synthesis and Physical Analysis of DNA Methods in Enzymology*, Academic Press; Handbook of Drug Screening, edited by Ramakrishna Seethala, Prabhavathi B. Fernandes (2001, New York, N.Y., Marcel Dekker, ISBN 0-8247-0562-9); *Lab Ref: A Handbook of Recipes, Reagents, and Other Reference Tools for Use at the Bench*, edited by Jane Roskams and Linda Rodgers, 2002, Cold Spring Harbor Laboratory, ISBN 0-87969-630-3; Harris, J M, and Zalipsky, S, eds, *Poly(ethylene glycol), Chemistry and Biological Applications*, ACS, Washington, 1997; Veronese, F., and J. M. Harris, Eds., *Peptide and protein PEGylation, Advanced Drug Delivery Reviews*, 54(4) 453-609 (2002); Zalipsky, S., et al., "*Use of functionalized Poly(Ethylene Glycols) for modification of polypeptides*" in Polyethylene Glycol Chemistry Biotechnical and Biomedical Applications. Each of these general texts is herein incorporated by reference.

CBX129801 is disclosed in U.S. Patent Application No. 2012/0178676, which is hereby incorporated by reference in its entirety.

The publications discussed above are provided solely for their disclosure before the filing date of the present application. Nothing herein is to be construed as an admission that the invention is not entitled to antedate such disclosure by virtue of prior invention.

I. Polyethylene Glycol (PEG)

PEG is a well-known polymer with good solubility in many aqueous and organic solvents, which exhibits low toxicity, lack of immunogenicity, and is clear, colorless, odorless, and stable. For these reasons and others, PEG has been selected as the preferred polymer for attachment, but it has been employed solely for purposes of illustration and not limitation. Similar products may be obtained with other water-soluble polymers, including without limitation; polyvinyl alcohol, other poly(alkylene oxides) such as poly(propylene glycol) and the like, poly(oxyethylated polyols) such as poly (oxyethylated glycerol) and the like, carboxymethylcellulose, dextran, polyvinyl alcohol, polyvinyl purrolidone, poly-1,3-dioxolane, poly-1,3,6-trioxane, ethylene/maleic anhydride, and polyaminoacids. One skilled in the art will be able to select the desired polymer based on the desired dosage, circulation time, resistance to proteolysis, and other considerations.

Representative polymeric reagents and methods for conjugating such polymers to an active moiety are described in Harris, J. M. and Zalipsky, S., Eds, Poly(ethylene glycol), *Chemistry and Biological Applications*, ACS, Washington, 1997; Veronese, F., and J. M. Harris, Eds., *Peptide and Protein PEGylation, Advanced Drug Delivery Reviews*, 54(4); 453-609 (2002); Zalipsky, S., et al., "Use of Functionalized Poly Ethylene Glycols) for Modification of Polypeptides" in *Polyethylene Glycol Chemistry: Biotechnical and Biomedical Applications*, J. M. Harris, ed., Plenus Press, New York (1992); Zalipsky (1995) *Advanced Drug Reviews* 16:157-182; and in Roberts et al., *Adv. Drug Delivery Reviews*, 54, 459-476 (2002).

A wide variety of PEG derivatives are both commercially available and suitable for use in the preparation of the PEG-conjugates of the invention. For example, NOF Corp.'s SUNBRIGHT® Series provides numerous PEG derivatives, including methoxypolyethylene glycols and activated PEG derivatives such as succinimidyl ester, methoxy-PEG amines, maleimides, and carboxylic acids, for coupling by various methods to C-peptide and Nektar Therapeutics' Advanced PEGylation also offers diverse PEG-coupling technologies to improve the safety and efficacy of therapeutics. Additional PEGs for use in forming a C-peptide conjugate of the invention include those available from Polypure (Norway), QuantaBioDesign LTD, (Ohio) and Sunbio, Inc. (South Korea). Further PEG reagents suitable for use in forming a conjugate of the invention and methods of conjugation are described in Pasut G., et al., *Expert Opin. Ther. Patents* (2004), 14(6), 859-893.

A search of patents, published patent applications, and related publications will also provide those skilled in the art reading this disclosure with significant possible PEG-coupling technologies and PEG-derivatives. For example, U.S. Pat. Nos. 7,026,440; 6,858,736; 6,828,401; 6,602,498; 6,495, 659; 6,448,369, 6,436,386; 5,990,237; 5,932,462; 5,900,461; 5,824,784; 5,739,208; 5,672,662; 5,650,234; 5,629,384; 5,252,714; and 4,904,584; the contents of which are incorporated by reference in their entirety, describe such technologies and derivatives, and methods for their manufacture.

The PEGylated C-peptides according to the invention have PEG moieties with a molecular weight varying within a range of about 4,000 Da to 80,000 Da. The molecular weight ranges will typically be from about 4000 Da to about 10,000 Da, from about 10,000 Da to about 20,000 Da, from about 20,000 Da to about 30,000 Da, from about 30,000 Da to about 40,000 Da, from about 40,000 Da to about 50,000 Da, from about 50,000 Da to about 60,000 Da, from about 60,000 Da to about 70,000 Da, and from about 70,000 Da to about 80,000 Da. Non-limiting examples of average molecular weights of the PEG moieties are about 10,000 Da, about 20,000 Da, about 30,000 Da, about 40,000 Da, about 50,000 Da, about 60,000 Da, about 70,000 Da, and about 80,000 Da.

Because virtually all PEG polymers exist as mixtures of diverse high molecular mass, PEG molecular weight (MW) is typically reported as number average ($M_n$), weight average ($M_w$), or z-average ($M_z$) molecular weights. The weight average is probably the most useful of the three, because it fairly accounts for the contributions of different sized chains to the overall behavior of the polymer, and correlates best with most of the physical properties of interest.

$$\text{Weight average } MW(Mw) = \frac{\sum (Mi^2 Ni)}{\sum (MiNi)}$$

$$\text{Number average } MW(Mn) = \frac{\sum (MiNi)}{\sum Ni}$$

$$Z \text{ average } MW(Mz) = \frac{\sum (Mi^3 Ni)}{\sum (Mi^2 Ni)}$$

where "Ni" is the mole-fraction (or the number-fraction) of molecules with molecular weight "Mi" in the polymer mixture. The ratio of Mw to Mn is known as the polydispersity index (PDI), and provides a rough indication of the breadth of the distribution. The PDI approaches 1.0 (the lower limit) for special polymers with very narrow MW distributions.

The PEG groups of the invention will for a given molecular weight typically consist of a range of ethylene glycol (or ethyleneoxide; $OCH_2CH_2$) monomers. For example, a PEG group of molecular weight 2000 Da will typically consist of 43±10 monomers, the average being around 43-44 monomers.

The PEG groups of the present invention will typically comprise a number of subunits, e.g., each n, $n_1$ or $n_2$ or $n_3$ in any of the claimed compounds may each independently be from about 1 to about 1000 subunits, from about 1 to about 800 subunits, from about 1 to about 600 subunits, from about 1 to about 400 subunits, from about 1 to about 300 subunits, or from about 1 to about 200 subunits. Well-suited PEG groups are such wherein the number of subunits (i.e., $n_1$, $n_2$, and $n_3$) are independently selected from the group consisting of from about 800 to about 1000 subunits; from about 800 to about 950 subunits; from about 600 to about 850 subunits; from about 400 to about 650 subunits; from about 200 to about 450 subunits; from about 180 to about 350 subunits; from about 100 to about 150 subunits; from about 35 to about 55 subunits; from about 42 to about 62 subunits; from about 12 to about 25 subunits subunits; or from about 1 to 10 subunits. In certain embodiments the PEGylated C-peptide will have a molecular weight of about 40 kDa, and thus $n_1$ and $n_2$ for each PEG chain in the branch chain PEGs will be within the range of about 440 to about 550 subunits, or about 450 to about 520 subunits.

II. Therapeutic Forms of C-Peptide

The terms "C-peptide" or "proinsulin C-peptide" as used herein includes all naturally occurring and synthetic forms of C-peptide that retain C-peptide activity. Such C-peptides include the human peptide, as well as peptides derived from other animal species and genera, preferably mammals, or a functionally equivalent derivative thereof, which may differ in their amino acid sequence, e.g., by truncation (e.g., from the N- or C-terminus or both) or other amino acid deletions, additions, insertions, substitutions, or post-translational modifications. Truncated forms of C-peptide must contain at a minimum, five amino acids with the sequence EGSLQ (SEQ. ID. No. 2, shown in Table C). Naturally-occurring chemical derivatives, including post-translational modifications and degradation products of C-peptide, are also specifically included in any of the methods and pharmaceutical compositions of the invention including, e.g., pyroglutamyl, iso-aspartyl, proteolytic, phosphorylated, glycosylated, oxidatized, isomerized, and deaminated variants of C-peptide. Preferably, "C-peptide" refers to human C-peptide having the amino acid sequence EAEDLQVGQVELGGGPGAGSLQ-PLALEGSLQ (SEQ. ID. No. 1, shown in Table C).

TABLE C

| C-peptide Variants | | |
|---|---|---|
| human M-proinsulin | Human<br>EAEDLQVGQVELGGGPGAGSLQPLALEGSLQ<br>GLU ALA GLU ASP LEU GLU VAL GLY GLU VAL<br>GLU LEU GLY GLY GLY PRO GLY ALA GLY SER<br>LEU GLU PRO LEU ALA LEU GLU GLY SER LEU<br>GLU<br>(SEQ. ID. No. 1) | gb\|AAA72531.1\|<br>dbj\|BAH59081.1\| |
| C-peptide fragment | EGSLQ<br>GLU GLY SER LEU GLU<br>(SEQ. ID. No. 2) | |

The PEGylated forms of C-peptide, C-peptide variants, derivatives, and fragments thereof are functionally equivalent in that they have detectable C-peptide activity. More particularly, they exhibit at least about 1%, at least about 5%, at least about 10%, at least about 15%, at least about 20%, at least about 30%, at least about 40%, at least about 50%, at least about 60%, at least about 70%, at least about 80%, at least about 90%, at least about 100%, or higher than 100% of the activity of native proinsulin C-peptide, particularly human C-peptide. Thus, they are capable of functioning as proinsulin C-peptide, i.e., can substitute for C-peptide itself. Such activity means any activity exhibited by a native C-peptide, whether a physiological response exhibited in an in vivo or in vitro test system, or any biological activity or reaction mediated by a native C-peptide, e.g., in an enzyme assay or in binding to test tissues, membranes, or metal ions. Thus, it is known that C-peptide causes an influx of calcium and initiates a range of intracellular signalling cascades such as phosphorylation of the MAP-kinase pathway including phosphorylation of PKC, RhoA, ERK 1 and 2, JNK and p38MAPK, resulting in an increased activation and expression of eNOS, Na+K+ATPase and a wide range of transcription factors (CREB, NF-kappaB, ATF1, ZEB and PPARgamma). An assay for C-peptide activity can thus be made by assaying for the activation or up-regulation of any of these pathways upon addition or administration of the peptide (e.g., fragment or derivative) in question to cells from relevant target tissues including endothelial, kidney, fibroblast and immune cells. Such assays are described in, e.g., Ohtomo Y et al. (*Diabetologia* 39: 199-205, (1996)), Kunt T et al. (*Diabetologia* 42(4): 465-471, (1999)), Shafqat J et al. (*Cell Mol. Life Sci.* 59: 1185-1189, (2002)). Kitamura T et al. (*Biochem. J.* 355: 123-129, (2001)), Hills and Brunskill (Exp Diab Res 2008), as described in WO 98/13384 or in Ohtomo Y et al. (supra) or Ohtomo Y et al. (*Diabetologia* 41: 287-291, (1998)). An assay for C-peptide activity based on endothelial nitric oxide synthase (eNOS) activity is also described in Kunt T et al. (supra) using bovine aortic cells and a reporter cell assay. Binding to particular cells may also be used to assess or assay for C-peptide activity, e.g., to cell membranes from human renal tubular cells, skin fibroblasts, and saphenous vein endothelial cells using fluorescence correlation spectroscopy, as described, e.g., in Rigler R et al. (*PNAS USA* 96: 13318-13323, (1999)), Henriksson M et al. (*Cell Mol. Life Sci.* 57: 337-342, (2000)) and Pramanik A et al. (*Biochem Biophys. Res. Commun.* 284: 94-98, (2001)).

In one aspect the mammal is a dog. In one aspect the mammal is a rat. In one aspect the mammal is a monkey. In one aspect the mammal is a human.

III. C-Peptide and PEGylated C-Peptide Production

C-Peptide Production

C-peptide may be produced synthetically using standard solid-phase peptide synthesis, or by recombinant technology, e.g., as a by-product in the production of human insulin from human proinsulin, or using genetically modified host (see generally WO 1999007735; Jonasson P, et al., *J Biotechnol.* (2000) 76(2-3):215-26; Jonasson P, et al., *Gene* (1998);20 (2):203-10; Li S X, Tian et al., *Sheng Wu Hua Xue Yu Sheng Wu Wu Li Xue Bao* (Shanghai) (2003) 35(11):986-92; Nilsson J, et al., *J Biotechnol*. (1996) 48(3):241-50; Huang Y B, et al., *Acta Biochim Biophys Sin* (Shanghai) (2006) 38(8):586-92).

In an alternative approach to direct coupling to the N-terminus, the PEG reagent, or a lysine residue, may be incorporated at a desired position of the C-peptide during peptide synthesis. In this way, site-selective introduction of one or more PEGs can be achieved. See, e.g., International Patent Publication No. WO 95/00162, which describes the site selective synthesis of conjugated peptides.

C-peptide can be produced by expressing a DNA sequence encoding the C-peptide in question in a suitable host cell by well known techniques used for insulin biosynthesis as disclosed in, e.g., U.S. Pat. No. 6,500,645. The C-peptide may be expressed directly, or as a multimerized construct to increase the yield of product as disclosed in U.S. Pat. No. 6,558,924. The multimerized product is cleaved in vitro after isolation from the culture broth.

The polynucleotide sequence coding for the C-peptide may be prepared synthetically by established standard methods, e.g., the phosphoamidite method described by Beaucage et al. (1981) *Tetrahedron Letters* 22:1859-1869, or the method described by Matthes et al. (1984) *EMBO Journal* 3:801-805. According to the phosphoramidite method, oligonucleotides are synthesized, e.g., in an automatic DNA synthesizer, purified, duplexed and ligated to form the synthetic DNA construct. A currently preferred way of preparing the DNA construct is by polymerase chain reaction (PCR).

The polynucleotide sequences may also be of mixed genomic, cDNA, and synthetic origin. For example, a genomic or cDNA sequence encoding a leader peptide may be joined to a genomic or cDNA sequence encoding the A and B chains, after which the DNA sequence may be modified at a site by inserting synthetic oligonucleotides encoding the desired amino acid sequence for homologous recombination in accordance with well-known procedures or preferably generating the desired sequence by PCR using suitable oligonucleotides.

The recombinant method will typically make use of a vector which is capable of replicating in the selected microorganism or host cell and which carries a polynucleotide sequence encoding the parent single-chain insulin of the invention. The recombinant vector may be an autonomously replicating vector, i.e., a vector which exists as an extra-chromosomal entity, the replication of which is independent of chromosomal replication, e.g., a plasmid, an extra-chromosomal element, a mini-chromosome, or an artificial chromosome.

The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used. The vector may be linear or closed circular plasmids and will preferably contain an element(s) that permits stable integration of the vector into the host cell's genome or autonomous replication of the vector in the cell independent of the genome.

The recombinant expression vector is capable of replicating in yeast. Examples of sequences which enable the vector to replicate in yeast are the yeast plasmid 2 pm replication genes REP 1-3 and origin of replication. The vector may contain one or more selectable markers which permit easy selection of transformed cells. A selectable marker is a gene the product of which provides for biocide or viral resistance, resistance to heavy metals, prototroph to auxotroph, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Selectable markers for use in a filamentous fungal host cell include amdS (acetamidase), argB (ornithine carbamoyl-transferase), pyrG (orotidine-5'-phosphate decarboxylase) and trpC (anthranilate synthase. Suitable markers for yeast host cells are ADE2, H153, LEU2, LYS2, MET3, TRP1, and URA3. A well-suited selectable marker for yeast is the *Schizosaccharomyces pompe* TPI gene (Russell (1985) *Gene* 40:125-130).

In the vector, the polynucleotide sequence is operably connected to a suitable promoter sequence. The promoter may be any nucleic acid sequence which shows transcriptional activity in the host cell of choice including mutant, truncated, and hybrid promoters, and may be obtained from genes encoding extra-cellular or intracellular polypeptides either homologous or heterologous to the host cell.

Examples of suitable promoters for directing the transcription in a bacterial host cell are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), and *Bacillus licheniformis* penicillinase gene (penP). Examples of suitable promoters for directing the transcription in a filamentous fungal host cell are promoters obtained from the genes for *Aspergillus oryzae* TAKA amylase, *Rhizomucor miehei* aspartic proteinase, *Aspergillus niger* neutral alpha-amylase, and *Aspergillus niger* acid stable alpha-amylase. In a yeast host, useful promoters are the *Saccharomyces cerevisiae* Mal, TPI, ADH, or PGK promoters. The polynucleotide sequence encoding the C-peptide of the invention will also typically be operably connected to a suitable terminator. In yeast a suitable terminator is the TPI terminator (Alber et al. (1982) *J. Mol. Appl. Genet.* 1:419-434).

The procedures used to ligate the polynucleotide sequence encoding the parent single-chain insulin of the invention, the promoter and the terminator, respectively, and to insert them into a suitable vector containing the information necessary for replication in the selected host, are well known to persons skilled in the art. It will be understood that the vector may be constructed either by first preparing a DNA construct containing the entire DNA sequence encoding the single-chain insulins of the invention, and subsequently inserting this fragment into a suitable expression vector, or by sequentially inserting DNA fragments encoding genetic information for the individual elements followed by ligation.

The vector comprising the polynucleotide sequence encoding the C-peptide of the invention is introduced into a host cell so that the vector is maintained as a chromosomal integrant or as a self-replicating extra-chromosomal vector. The term "host cell" encompasses any progeny of a parent cell that is not identical to the parent cell due to mutations that occur during replication. The host cell may be a unicellular microorganism, e.g., a prokaryote, or a non-unicellular microorganism, e.g., a eukaryote. Useful unicellular cells are bacterial cells such as gram positive bacteria including, but not limited to, a *Bacillus* cell, *Streptomyces* cell, or gram negative bacteria such as *E. coli* and *Pseudomonas* sp. Eukaryote cells may be mammalian, insect, plant, or fungal cells. In one embodiment, the host cell is a yeast cell. The yeast organism may be any suitable yeast organism which, on cultivation, produces large amounts of the single chain insulin of the invention. Examples of suitable yeast organisms are strains selected from the yeast species *Saccharomyces cerevisiae*, *Saccharomyces kluyveri*, *Schizosaccharomyces pombe*, *Sacchoromyces uvarum*, *Kluyvero-myces lactis*, *Hansenula polymorpha*, *Pichia pastoris*, *Pichia methanolica*, *Pichia kluyveri*, *Yarrowia ilpolytica*, *Candida* sp., *Candida utilis*, *Candida cacaoi*, *Geotrichum* sp., and *Geotrichum fermentans*.

The transformation of the yeast cells may for instance be effected by protoplast formation followed by transformation in a manner known per se. The medium used to cultivate the cells may be any conventional medium suitable for growing yeast organisms. The secreted single-chain insulin, a significant proportion of which will be present in the medium in correctly processed form, may be recovered from the medium by conventional procedures including separating the yeast cells from the medium by centrifugation, filtration or catching the insulin precursor by an ion exchange matrix or by a reverse phase absorption matrix, precipitating the proteinaceous components of the supernatant or filtrate by means of a salt, e.g., ammonium sulphate, followed by purification by a variety of chromatographic procedures, e.g., ion exchange chromatography, affinity chromatography, or the like.

PEGlyated C-Peptide Production

In certain embodiments, C-peptide is reacted with a suitable activated PEG derivative in the presence of an appropriate base, in an appropriate solvent. In further embodiments, the activated PEG derivative is branched, approx. 40 kDa-NHS ester PEG derivative (SUNBRIGHT GL2-400GS2 (NOF Corporation)). In further embodiments, the base is N-methyl morpholine. In further embodiments, the solvent is a mixture of acetonitrile and water. In further embodiments, the solvent is a 50/50 mixture of acetonitrile and water. In further embodiments, the N-methyl morpholine is added portion-wise at intervals. In further embodiments, the N-methyl morpholine is added portion-wise at one hour intervals. In further embodiments, the pH of the reaction mixture is monitored and N-methyl morpholine is added as required to maintain pH. In further embodiments, the pH is maintained at 8.0 to 8.2.

In certain embodiments, the PEGylated C-peptide is purified by preparative reverse phase chromatography. In further embodiments the column is reverse phase silica. In further embodiments the reverse phase silica is C-18 reverse phase silica. In further embodiments the reverse phase silica is Diasogel C-18, 15 µm, 300 Angstrom. In further embodiments the reaction mixture containing C-peptide mixture is diluted with a mixture of an acid and water. In further embodiments the reaction mixture containing C-peptide mixture is diluted with 6 volumes of 0.1% trifluoroacetic acid (TFA)/water. In further embodiments the adsorbed PEGylated C-peptide is eluted from the column by applying a gradient of acetonitrile (ACN) in dilute aqueous acid. In further embodiments the adsorbed PEGylated C-peptide is eluted from the column by applying a gradient of ACN in dilute aqueous TFA (Buffer A is 0.1% TFA, Buffer B is 100% ACN: 0 to 25% B in 5 minutes, then 25% to 50% B during 100 minutes and then hold until the product is eluted).

In certain embodiments, the PEGylated C-peptide is purified and desalted by preparative reverse phase chromatography. In further embodiments the column is reverse phase silica. In further embodiments the reverse phase silica is C-18 reverse phase silica. In further embodiments the reverse phase silica is Diasogel C-18, 15 µm, 300 Angstrom. In further embodiments the adsorbed PEGylated C-peptide is eluted from the column by applying a gradient of ACN in dilute aqueous acid. In further embodiments the adsorbed PEGylated C-peptide is eluted from the column by applying a gradient of ACN in dilute aqueous acetic acid (AcOH) (Buffer A is 2% acetic acid, Buffer B is 100% acetonitrile: 0 to 25% B in 5 minutes, then 25% to 50% B during 50 minutes and then hold until the product is eluted). In further embodiments the PEGylated C-peptide containing fractions are lyophilized.

In certain embodiments, the PEGylated C-peptide is purified by preparative ion exchange chromatography. In further embodiments the ion exchange column is a modified cellulose column. In further embodiments the ion exchange column is DEAE52 Cellulose. In certain embodiments the PEGylated C-peptide is dissolved in an aqueous solvent mixture and applied to the column. In further embodiments the aqueous solvent mixture is ACN/water. In further embodiments the aqueous solvent mixture is 5% ACN/water. In further embodiments the PEGylated C-peptide is eluted from the column with an aqueous buffer. In further embodiments the buffer is an aqueous solution of sodium chloride and ammonium acetate. In further embodiments the buffer is an aqueous solution of sodium chloride (1M) and ammonium acetate (1M). In further embodiments the buffer is aqueous AcOH in 5% ACN. In further embodiments the aqueous AcOH in 5% is applied as a gradient. In further embodiments the aqueous AcOH gradient is 1% to 5%.

In certain embodiments, the PEGylated C-peptide is purified by preparative reverse phase chromatography. In further embodiments the column is reverse phase silica. In further embodiments the reverse phase silica is C-18 reverse phase silica. In further embodiments the reverse phase silica is Diasogel C-18, 15 µm, 300 Angstrom. In further embodiments the fractions from the ion exchange chromatography step containing C-peptide mixture are diluted with water. In further embodiments the column is washed with dilute acid. In further embodiments the column is washed with 2% AcOH. In further embodiments the adsorbed PEGylated C-peptide is eluted from the column by applying a gradient of ACN in dilute AcOH. In further embodiments the adsorbed PEGylated C-peptide is eluted from the column by applying a gradient of ACN in dilute AcOH (Buffer A is 2% AcOH, Buffer B is 100% ACN: 0 to 25% B in 5 minutes, then 25% to 50% B during 50 minutes and then hold until the product is eluted). In certain embodiments the PEGylated C-peptide containing fractions are lyophilized.

In certain embodiments PEGylated C-peptide is reconstituted as an aqueous acid solution. In further embodiments the PEGylated C-peptide is reconstituted in 2% aqueous AcOH. In further embodiments the PEGylated C-peptide is reconstituted at a concentration of about 15-20 g/L. In further embodiments the PEGylated C-peptide solution is lyophilized to give the pure PEGylated C-peptide drug substance as its free acid.

IV. Methods of Use

In one aspect, the present invention includes a method for maintaining C-peptide levels above the minimum effective therapeutic level in a patient in need thereof, comprising administering to the patient a therapeutic dose of any of the claimed PEGylated C-peptides.

In another aspect, the present invention includes a method for maintaining C-peptide levels at or above an average effective therapeutic level in a patient in need thereof, comprising administering to the patient a therapeutic dose of any of the claimed PEGylated C-peptides.

In another aspect, the present invention includes a method for treating one or more long-term complications of diabetes in a patient in need thereof, comprising administering to the patient a therapeutic dose of any of the claimed PEGylated C-peptides.

In another aspect, the present invention includes a method for treating a patient with diabetes comprising administering to the patient a therapeutic dose of any of the claimed PEGylated C-peptides in combination with insulin.

In another aspect, the present invention includes any of the claimed PEGylated C-peptides for use as a C-peptide replacement therapy or dose in a patient in need thereof.

In broad terms, diabetes refers to the situation where the body either fails to properly respond to its own insulin, does not make enough insulin, or both. The primary result of impaired insulin production is the accumulation of glucose in the blood, and a C-peptide deficiency leading to various short- and long-term complications. Three principal forms of diabetes exist:

Type 1:

Results from the body's failure to produce insulin and C-peptide. It is estimated that 5-10% of Americans who are diagnosed with diabetes have type 1 diabetes. Presently almost all persons with type 1 diabetes must take insulin injections. The term "type 1 diabetes" has replaced several former terms, including childhood-onset diabetes, juvenile diabetes, and insulin-dependent diabetes mellitus (IDDM). For patients with type 1 diabetes, basal levels of C-peptide are typically less than about 0.20 nM (Ludvigsson et al.: *New Engl. J. Med.* 359: 1909-1920, (2008)).

Type 2:

Results from tissue insulin resistance, a condition in which cells fail to respond properly to insulin, sometimes combined with relative insulin deficiency. The term "type 2 diabetes" has replaced several former terms, including adult-onset diabetes, obesity-related diabetes, and non-insulin-dependent diabetes mellitus (NIDDM). For type 2 patients in the basal state, C-peptide levels of about 0.8 nM (range 0.64 to 1.56 nM), and glucose stimulated levels of about 5.7 nM (range 3.7 to 7.7 nM) have been reported. (Retnakaran R et al.: *Diabetes Obes. Metab.* (2009) DOI 10.11 111/j.1463-1326.2009.01129.x; Zander et al.: *Lancet* 359: 824-830, (2002)).

In addition to type 1 and type 2 diabetic patients, there is increasing recognition of a subclass of diabetes referred to as latent autoimmune diabetes in the adult (LADA) or late-onset autoimmune diabetes of adulthood, or "slow onset type 1" diabetes, and sometimes also "type 1.5" or "type one-and-a-half" diabetes. In this disorder, diabetes onset generally occurs in ages 35 and older, and antibodies against components of the insulin-producing cells are always present, demonstrating that autoimmune activity is an important feature of LADA. It is primarily antibodies against glutamic acid decarboxylase (GAD) that are found. Some LADA patients show a phenotype similar to that of type 2 patients with increased body mass index (BMI) or obesity, insulin resistance, and abnormal blood lipids. Genetic features of LADA are similar to those for both type 1 and type 2 diabetes. During the first 6-12 months after debut the patients may not require insulin administration and they are able to maintain relative normoglycemia via dietary modification and/or oral anti-diabetic medication. However, eventually all patients become insulin dependent, probably as a consequence of progressive autoimmune activity leading to gradual destruction of the pancreatic islet β-cells. At this stage the LADA patients show low or absent levels of endogenous insulin and C-peptide, and they are prone to develop long-term complications of diabetes involving the peripheral nerves, the kidneys, or the eyes similar to type 1 diabetes patients and thus become candidates for C-peptide therapy (Palmer et al.: *Diabetes* 54(suppl 2): S62-67, (2005); Desai et al.: *Diabetic Medicine* 25(suppl 2): 30-34, (2008); Fourlanos et al.: *Diabetologia* 48: 2206-2212, (2005)).

Additional subclasses of insulin-requiring patients which would benefit from administration of the PEGylated C-peptide disclosed herein include patients who lack a properly functioning pancreas due to injury, congenital defect, or through damage or physical injury.

Accordingly in any of these methods, the term "patient" refers to an individual who has one of more of the symptoms of diabetes. In one aspect of any of these methods, the term "patient" refers to an individual who has one or more of the symptoms of any of insulin-requiring diabetes. In one aspect of any of these methods, the term "patient" refers to an individual who has one or more of the symptoms of any of type 2 diabetes. In one aspect of any of these methods, the term "patient" refers to an individual who has one or more of the symptoms of LADA. Accordingly in one aspect of any of these methods, the term "patient" refers to an individual who has a fasting C-peptide level of less than about 0.4 nM. In another aspect of any of these methods, the term "patient" refers to an individual who has a fasting C-peptide level of less than about 0.2 nM.

In another aspect, the present invention includes a method for treating one or more long-term complications of diabetes in a patient in need thereof, comprising administering to the patient a therapeutic dose of any of the claimed PEGylated C-peptides.

In another aspect, the present invention includes a method for treating a patient with diabetes comprising administering to the patient a therapeutic dose of any of the claimed PEGylated C-peptides in combination with insulin.

In this context "in combination" means: 1) part of the same unitary dosage form; 2) administration separately, but as part of the same therapeutic treatment program or regimen, typically but not necessarily, on the same day. In one aspect, any of the claimed PEGylated C-peptides may be administered at a fixed daily dosage, and the insulin taken on an as needed basis.

In another aspect, the present invention includes any of the claimed PEGylated C-peptides for use for treating one or more long-term complications of diabetes in a patient in need thereof.

In any of these methods, the terms "long-term complication of type 1 diabetes", or "long-term complications of diabetes" refers to the long-term complications of impaired glycemic control, and C-peptide deficiency associated with type 1 diabetes. Typically long-term complications of type 1 diabetes are associated with type 1 diabetic patients. However, the term can also refer to long-term complications of diabetes that arise in type 1.5 and type 2 diabetic patients or patients with a damaged or missing pancreas who develop a C-peptide deficiency as a consequence of losing pancreatic islet β-cells and therefore also become insulin requiring. In broad terms, many such complications arise from the primary damage of blood vessels (angiopathy), resulting in subsequent problems that can be grouped under "microvascular disease" (due to damage to small blood vessels) and "macrovascular disease" (due to damage to the arteries).

Specific diseases and disorders included within the term long-term complications of diabetes include, without limitation; retinopathy including early stage retinopathy with microaneurysms, proliferative retinopathy, and macular edema; peripheral neuropathy including sensorimotor polyneuropathy, painful sensory neuropathy, autonomic neuropathy involving the cardiovascular system, the gastrointestinal tract, the respiratory system, the urogenital system, sudomotor function and papillary function; and nephropathy including disorders with microalbuminuria, overt proteinuria, and end-stage renal disease.

Impaired microcirculatory perfusion appears to be crucial to the pathogenesis of both neuropathy and retinopathy in diabetic patients. This in turn reflects a hyperglycemia-mediated perturbation of vascular endothelial function that results in: over-activation of protein kinase C, reduced availability of nitric oxide (NO), increased production of superoxide and endothelin-1 (ET-1), impaired insulin function, diminished synthesis of prostacyclin/PGE1, and increased activation and endothelial adherence of leukocytes. This is ultimately a catastrophic group of clinical events.

Accordingly in some embodiments, the term "patient" refers to an individual who has one of more of the symptoms of the long-term complications of diabetes.

Diabetic retinopathy is an ocular manifestation of the systemic damage to small blood vessels leading to microangiopathy. In retinopathy, growth of friable and poor-quality new blood vessels in the retina as well as macular edema (swelling of the macula) can lead to severe vision loss or blindness. As new blood vessels form at the back of the eye as a part of proliferative diabetic retinopathy (PDR), they can bleed (hemorrhage) and blur vision. It affects up to 80% of all patients who have had diabetes for 10 years or more.

The symptoms of diabetic retinopathy are often slow to develop and subtle and include blurred version and progressive loss of sight. Macular edema, which may cause vision loss more rapidly, may not have any warning signs for some time. In general, however, a person with macular edema is likely to have blurred vision, making it hard to do things like read or drive. In some cases, the vision will get better or worse during the day.

Accordingly in some embodiments, the term "patient" refers to an individual who has one of more of the symptoms of diabetic retinopathy.

Diabetic neuropathies are neuropathic disorders that are associated with diabetic microvascular injury involving small blood vessels that supply nerves (vasa nervorum). Relatively common conditions which may be associated with diabetic neuropathy include diabetic amyotrophy; painful polyneuropathy; and autonomic neuropathy.

Diabetic neuropathy affects all peripheral nerves: pain fibers, motor neurons, autonomic nerves. It therefore necessarily can affect all organs and systems since all are innervated. There are several distinct syndromes based on the organ systems and members affected, but these are by no means exclusive. A patient can have sensorimotor and autonomic neuropathy or any other combination. Symptoms vary depending on the nerve(s) affected and may include symptoms other than those listed. Symptoms usually develop gradually over years.

Symptoms of diabetic neuropathy may include: numbness and tingling of extremities, dysesthesia (decreased or loss of sensation to a body part), diarrhea, erectile dysfunction, female sexual dysfunction, urinary incontinence (loss of bladder control), impotence, facial, mouth and eyelid drooping, vision changes, dizziness, muscle weakness, difficulty swallowing, speech impairment, fasciculation (muscle contractions), anorgasmia, and burning or electric pain.

Additionally, different nerves are affected in different ways by neuropathy. Sensorimotor polyneuropathy, in which longer nerve fibers are affected to a greater degree than shorter ones, because nerve conduction velocity is slowed in proportion to a nerve's length. In this syndrome, decreased sensation and loss of reflexes occurs first in the toes on each foot, then extends upward. It is usually described as glove-stocking distribution of numbness, sensory loss, dysesthesia, and night-time pain. The pain can feel like burning, pricking sensation, achy, or dull. Pins and needles sensation is common. Loss of proprioception, the sense of where a limb is in space, is affected early. These patients cannot feel when they are stepping on a foreign body, like a splinter, or when they are developing a callous from an ill-fitting shoe. Consequently, they are at risk for developing ulcers and infections on the feet and legs, which can lead to amputation. Similarly, these patients can get multiple fractures of the knee, ankle, or foot, and develop a Charcot joint. Loss of motor function results in dorsiflexion, contractures of the toes, loss of the interosseous muscle function, and leads to contraction of the digits, so called hammer toes. These contractures occur not only in the foot, but also in the hand where the loss of the musculature makes the hand appear gaunt and skeletal. The loss of muscular function is progressive.

Autonomic neuropathy impacts the autonomic nervous system serving the heart, gastrointestinal system, and genitourinary system. The most commonly recognized autonomic dysfunction in diabetic patients is orthostatic hypotension, or fainting when standing up. In the case of diabetic autonomic neuropathy, it is due to the failure of the heart and arteries to appropriately adjust heart rate and vascular tone to keep blood continually and fully flowing to the brain. This symptom is usually accompanied by a loss of the usual change in heart rate seen with normal breathing. These two findings suggest cardiac autonomic neuropathy.

Gastrointestinal system symptoms associated with autonomic neuropathy include delayed gastric emptying, gastroparesis, nausea, bloating, and diarrhea. Because many diabetic patients take oral medication for their diabetes, absorption of these medicines is greatly affected by the delayed gastric emptying. This poor absorption can lead to hyperglycemia when an oral diabetic agent is taken before a meal and does not get absorbed until hours later. Sluggish movement of the small intestine can cause bacterial overgrowth, made worse by the presence of hyperglycemia. This leads to bloating, gas, and diarrhea.

Genitourinary system symptoms associated with autonomic neuropathy include urinary frequency, urgency, incontinence, retention, impotence, erectile dysfunction, and female sexual dysfunction. Urinary retention can lead to bladder diverticula, stones, reflux nephropathy, and frequent urinary tract infections. Administration of C-peptide has been shown to improve erectile function in insulin-requiring diabetic patients (Wahren et al.: *Diabetes* 60, Suppl 1: A285, (2011)). Accordingly in any of these methods, the term "patient" refers to an individual who has one of more of the symptoms of autonomic neuropathy. In certain methods, the term "patient" refers to an individual who has one or more symptoms of erectile dysfunction, female sexual dysfunction, or impotence.

Accordingly in some embodiments, the term "patient" refers to an individual who has one of more of the symptoms of diabetic neuropathy. In another aspect of any of these methods, the patient has "established peripheral neuropathy" which is characterized by reduced nerve conduction velocity (NCV) in two or more peripheral nerves (less than −1.5 SD from a body height-corrected reference value for a matched normal individual). In certain embodiments, the term "patient" refers to an individual who has one of more of the symptoms of incipient neuropathy.

Accordingly in certain embodiments, the current invention includes a method of treating or preventing a decrease in a subject's, or patient's, height-adjusted sensory or motor nerve conduction velocity. In one aspect of this method, the motor nerve conduction velocity is initial nerve conduction velocity. In another embodiment, the motor nerve conduction velocity is the peak nerve conduction velocity.

In certain embodiments the subject is a patient with diabetes. In certain embodiments, the subject has at least one long-term complication of diabetes. In one aspect, the patient exhibits a peak nerve conduction velocity that is at least about 2 standard deviations from the mean peak nerve conduction velocity for a similar height-matched subject group. In one aspect, the patients have a peak nerve conduction velocity of less than about 35 m/s. In one aspect of any of the claimed methods, the patients have a peak nerve conduction velocity of less than about 40 m/s. In one aspect, the patients have a peak nerve conduction velocity of less than about 45 m/s. In one aspect, the patients have a peak nerve conduction velocity of less than about 50 m/s.

In one aspect of any of the claimed methods, treatment results in an improvement in nerve conduction velocity of at least about 0.2 m/s. In one aspect of any of the claimed methods, treatment results in an improvement in nerve conduction velocity of at least about 0.4 m/s. In one aspect of any of the claimed methods, treatment results in an improvement in nerve conduction velocity of at least about 0.6 m/s. In one aspect of any of the claimed methods, treatment results in an improvement in nerve conduction velocity of at least about 0.8 m/s. In one aspect of any of the claimed methods, treatment results in an improvement in nerve conduction velocity of at least about 1.0 m/s. In one aspect of any of the claimed methods, treatment results in an improvement in nerve conduction velocity of at least about 1.2 m/s. In one aspect of any of the claimed methods, treatment results in an improvement in nerve conduction velocity of at least about 1.5 m/s. In another aspect of these methods, treatment results in an improvement in nerve conduction velocity of at least about 2.0 m/s. In another aspect of these methods, treatment results in an improvement in nerve conduction velocity of at least about 2.5 m/s. In another aspect of these methods, treatment results in an improvement in nerve conduction velocity of at least about 3.0 m/s. In another aspect of these methods, treatment results in an improvement in nerve conduction velocity of at least about 3.5 m/s. In another aspect of these methods, treatment results in an improvement in nerve conduction velocity of at least about 4.0 m/s. In another aspect of these methods, treatment results in an improvement in nerve conduction velocity of at least about 4.5 m/s. In another aspect of these methods, treatment results in an improvement in nerve conduction velocity of at least about 5.0 m/s. In another aspect of these methods, treatment results in an improvement in nerve conduction velocity of at least about 5.5 m/s. In another aspect of these methods, treatment results in an improvement in nerve conduction velocity of at least about 6.0 m/s. In another aspect of these methods, treatment results in an improvement in nerve conduction velocity of at least about 7.0 m/s. In another aspect of these methods, treatment results in an improvement in nerve conduction velocity of at least about 8.0 m/s. In another aspect of these methods, treatment results in an improvement in nerve conduction velocity of at least about 9.0 m/s. In another aspect of these methods, treatment results in an improvement in nerve conduction velocity of at least about 10.0 m/s. In another aspect of these methods, treatment results in an improvement in nerve conduction velocity of at least about 15.0 m/s. In another aspect of these methods, treatment results in an improvement in nerve conduction velocity of at least about 20.0 m/s.

In further embodiments, the improvement in nerve conduction velocity is achieved in 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 5 months, 6 months, 7 months, 8 months, 9 months, 10 months, 11 months, 12 months, 18 months, or two years.

Diabetic nephropathy is a progressive kidney disease caused by angiopathy of capillaries in the kidney glomeruli. It is characterized by nephrotic syndrome and diffuse glomerulosclerosis. It is due to long-standing diabetes mellitus, and is a prime cause for dialysis in many Western countries.

The symptoms of diabetic nephropathy can be seen in patients with chronic diabetes (15 years or more after onset). The disease is progressive and is more frequent in men. Diabetic nephropathy is the most common cause of chronic kidney failure and end-stage kidney disease in the United States. People with both type 1 and type 2 diabetes are at risk. The risk is higher if blood-glucose levels are poorly controlled. Further, once nephropathy develops, the greatest rate of progression is seen in patients with poor control of their blood pressure. Also people with high cholesterol levels in their blood have much more risk than others.

The earliest detectable change in the course of diabetic nephropathy is an abnormality of the glomerular filtration barrier. At this stage, the kidney may start allowing more serum albumin than normal in the urine (albuminuria), and this can be detected by sensitive medical tests for albumin. This stage is called "microalbuminuria." As diabetic nephropathy progresses, increasing numbers of glomeruli are destroyed by nodular glomerulosclerosis. Now the amounts of albumin being excreted in the urine increases, and may be detected by ordinary urinalysis techniques. At this stage, a kidney biopsy clearly shows diabetic nephropathy.

Kidney failure provoked by glomerulosclerosis leads to fluid filtration deficits and other disorders of kidney function. There is an increase in blood pressure (hypertension) and fluid retention in the body plus a reduced plasma oncotic pressure causes edema. Other complications may be arteriosclerosis of the renal artery and proteinuria.

Throughout its early course, diabetic nephropathy has no symptoms. They develop in late stages and may be a result of excretion of high amounts of protein in the urine or due to renal failure. Symptoms include edema and swelling, usually around the eyes in the mornings; later, general body swelling may result, such as swelling of the legs, foamy appearance or excessive frothing of the urine (caused by the proteinuria), unintentional weight gain (from fluid accumulation), anorexia (poor appetite), nausea and vomiting, malaise (general ill feeling), fatigue, headache, frequent hiccups, and generalized itching.

Accordingly in some embodiments, the term "patient" refers to an individual who has one of more of the symptoms of diabetic nephropathy.

Macrovascular diseases of diabetes include coronary artery disease, leading to angina or myocardial infarction ("heart attack"), stroke (mainly the ischemic type), peripheral vascular disease, which contributes to intermittent claudication (exertion-related leg and foot pain), as well as diabetic foot and diabetic myonecrosis ("muscle wasting").

In certain embodiments, the term "patient" refers to an individual who has one of more of the symptoms of a macrovascular disease of diabetes.

Methods for Preventing Hypoglycemia.

In certain embodiments, the present invention includes the use of any of the disclosed PEGylated C-peptides whereby the risk of hypoglycemia in a human patient with insulin-requiring diabetes is reduced, in a regimen which additionally comprises the administration of insulin, comprising; a) administering insulin to said patient; b) administering a therapeutic dose of PEGylated C-peptide in a different site as that used for said patient's insulin administration; c) adjusting the dosage amount, type, or frequency of insulin administered based on said patient's altered insulin requirements resulting from said therapeutic dose of PEGylated C-peptide.

In another aspect, the present invention includes a method of reducing insulin usage in an insulin-requiring human patient, comprising the steps of; a) administering insulin to said patient; b) administering subcutaneously to said patient a therapeutic dose of any of the disclosed PEGylated C-peptides in a different site as that used for said patient's insulin administration; c) adjusting the dosage amount, type, or frequency of insulin administered based on monitoring said patient's altered insulin requirements resulting from said therapeutic dose of PEGylated C-peptide, wherein said adjusted dose of insulin does not result in hyperglycemia, wherein said adjusted dose of insulin is at least 10% less than said patient's insulin dose prior to starting PEGylated C-peptide. (See for example U.S. Pat. No. 7,855,177, which is herein incorporated by reference).

In any of these methods, the term "hypoglycemia" or "hypoglycemic events" refers to all episodes of abnormally low plasma glucose concentration that exposes the patient to potential harm. The American Diabetes Association Workgroup has recommended that people with insulin-requiring diabetes become concerned about the possibility of developing hypoglycemia at a plasma glucose concentration of less than 70 mg/dL (3.9 mmoL/L). Accordingly in one aspect of any of the claimed methods, the terms hypoglycemia or hypoglycemic event refers to the situation where the plasma glucose concentration of the patient drops to less than about 70 mg/dL (3.9 mmoL/L).

Hypoglycemia is a serious medical complication in the treatment of diabetes, and causes recurrent morbidity in most people with type 1 diabetes and many with advanced type 2 diabetes and is sometimes fatal. In addition, hypoglycemia compromises physiological and behavioral defenses against subsequent falling plasma glucose concentrations and thus causes a vicious cycle of recurrent hypoglycemia and hypoglycemic unawareness. Accordingly the prevention of hypoglycemia is of significant importance in the treatment of diabetes, as well as the treatment of the long-term complications of diabetes.

Unfortunately hypoglycemia is a fact of life for most people with type 1 diabetes (Cryer P E et al.: *Diabetes* 57: 3169-3176, (2008)). The average patient has multiple episodes of asymptomatic hypoglycemia and suffers recurrent symptomatic hypoglycemia per week. He or she may also suffer periodic episodes of severe, temporarily disabling hypoglycemia often with seizure or coma, requiring the assistance of a third party.

Overall, hypoglycemia is less frequent in type 2 diabetes; however, the risk of hypoglycemia becomes progressively more frequent and limiting to glycemic control later in the course of type 2 diabetes. The prospective, population-based data of Donnelly et al. (*Diabetes Med.* 22: 749-755, (2005)) indicate that the overall incidence of hypoglycemia in insulin-treated type 2 diabetes is approximately one third of that in type 1 diabetes. The incidence of any hypoglycemia and of severe hypoglycemia was 4,300 and 115 episodes per 100 patient years, respectively, in type 1 diabetes and 1600 and 35 episodes per 100 patient years, respectively, in insulin-treated type 2 diabetes.

Hypoglycemia may be classified based on the severity of the hypoglycemic event. For example, the American Diabetes Association Workgroup has suggested the following classification of hypoglycemia in diabetes: 1) severe hypoglycemia (i.e., hypoglycemic coma requiring assistance of another person); 2) documented symptomatic hypoglycemia (with symptoms and a plasma glucose concentration of less than 70 mg/dL); 3) asymptomatic hypoglycemia (with a plasma glucose concentration of less than 70 mg/dL without symptoms); 4) probable symptomatic hypoglycemia (with symptoms attributed to hypoglycemia, but without a plasma glucose measurement); and 5) relative hypoglycemia (with a plasma glucose concentration of greater than 70 mg/dL but falling towards that level).

Thus, in another aspect of any of the methods disclosed herein, the term "hypoglycemia" refers to severe hypoglycemia, and/or hypoglycemic coma. In another aspect of any of these methods, the term "hypoglycemia" refers to symptomatic hypoglycemia. In another aspect of any of these methods, the term "hypoglycemia" refers to probable symptomatic hypoglycemia. In another aspect of any of these methods, the term "hypoglycemia" refers to asymptomatic hypoglycemia. In another aspect of any of these methods, the term "hypoglycemia" refers to relative hypoglycemia.

Insulin Types and Administration Forms

There are over 180 individual insulin preparations available worldwide which have been developed to provide different lengths of activity (activity profiles). Approximately 25% of these are soluble insulin (unmodified form); about 35% are long- or intermediate-acting basal insulins (mixed with NPH [neutral protamine Hagedorn] insulin or Lente insulin [insulin zinc suspension], or forms that are modified to have an increased isoelectric point [insulin glargine], or acylation [insulin detemir]; these forms have reduced solubility, slow subcutaneous absorption, and long duration of action relative to soluble insulins); about 2% are rapid-acting insulins (e.g., which are engineered by amino acid change, and have reduced self-association and increased subcutaneous absorption); and about 38% are pre-mixed insulins (e.g., mixtures of short-, intermediate-, and long-acting insulins; these preparations have the benefit of a reduced number of daily injections).

Short-acting insulin preparations that are commercially available in the US include regular insulin and rapid-acting insulins. Regular insulin has an onset of action of 30-60 minutes, peak time of effect of 1.5 to 2 hours, and duration of activity of 5 to 12 hours. Rapid-acting insulins, such as aspart (NovoLog), lispro (Humalog), and glulisine (Apidra), have an onset of action of 10-30 minutes, peak time of effect of around 30 minutes, and a duration of activity of 3 to 5 hours.

Intermediate-acting insulins, such as NPH and Lente insulins, have an onset of action of 1 to 2 hours, peak time of effect of 4 to 8 hours, and a duration of activity of 10 to 20 hours.

Long-acting insulins, such as Ultralente insulin, have an onset of action of 2 to 4 hours, peak time of effect of 8 to 20 hours, and a duration of activity of 16 to 24 hours. Other examples of long-acting insulins include glargine (Lantus) and determir (Levemir). Glargine insulin has an onset of action of 1 to 2 hours, and a duration of action of 24 hours, but with no peak effect.

In many cases, regimens that use insulin in the management of diabetes combine long-acting and short-acting insulin. Some of these regimens involve premixed insulin formulations. Lantus (glargine), from Aventis Pharmaceuticals Inc., is a recombinant human insulin analog that is a long-acting, parenteral blood-glucose-lowering agent whose longer duration of action (up to 24 hours) is directly related to its slower rate of absorption. Lantus is administered subcutaneously once a day, preferably at bedtime, and is said to provide a continuous level of insulin, similar to the slow, steady (basal) secretion of insulin provided by the normal pancreas. The activity of such a long-acting insulin results in a relatively constant concentration/time profile over 24 hours with no pronounced peak, thus allowing it to be administered once a day as a patient's basal insulin. Such long-acting insulin has a long-acting effect by virtue of its chemical composition, rather than by virtue of an addition to insulin when administered.

More recently automated wireless controlled systems for continuous infusion of insulin, such as the system sold under the trademark OMNIPOD™ Insulin Management System (Insulet Corporation, Bedford, Mass.) have been developed. These systems provide continuous subcutaneous insulin delivery with blood glucose monitoring technology in a discreet two-part system. This system eliminates the need for daily insulin injections, and does not require a conventional insulin pump which is connected via tubing.

OMNIPOD™ is a small lightweight device that is worn on the skin like an infusion set. It delivers insulin according to pre-programmed instructions transmitted wirelessly from the Personal Diabetes Manager (PDM). The PDM is a wireless, hand-held device that is used to program the OMNIPOD™ Insulin Management System with customized insulin delivery instructions, monitor the operation of the system, and check blood glucose levels using blood glucose test strips sold under the trademark FREESTYLE™. There is no tubing connecting the device to the PDM. OMNIPOD™ Insulin Management System is worn beneath the clothing, and the PDM can be carried separately in a backpack, briefcase, or purse. Similar to currently available insulin pumps, the OMNIPOD™ Insulin Management System features fully programmable continuous subcutaneous insulin delivery with multiple basal rates and bolus options, suggested bolus calculations, safety checks, and alarm features.

The aim of insulin treatment of diabetic patients is typically to administer enough insulin such that the patient will have blood glucose levels within the physiological range and normal carbohydrate metabolism throughout the day. Because the pancreas of a diabetic individual does not secrete sufficient insulin throughout the day, in order to effectively control diabetes through insulin therapy, a long-lasting insulin treatment, known as basal insulin, must be administered to provide the slow and steady release of insulin that is needed to control blood glucose concentrations and to keep cells supplied with energy when no food is being digested. Basal insulin is necessary to suppress glucose production between meals and overnight and preferably mimics the patient's normal pancreatic basal insulin secretion over a 24-hour period. Thus, a diabetic patient may administer a single dose of a long-acting insulin each day subcutaneously, with an action lasting about 24 hours.

Furthermore, in order to effectively control diabetes through insulin therapy by dealing with postprandial rises in glucose levels, a bolus, fast-acting treatment must also be administered. The bolus insulin, which is generally administered subcutaneously, provides a rise in plasma insulin levels at approximately 1 hour after administration, thereby limiting hyperglycemia after meals. Thus, these additional quantities of regular insulin, with a duration of action of, e.g., 5 to 6 hours, may be subcutaneously administered at those times of the day when the patient's blood glucose level tends to rise too high, such as at meal times. As an alternative to administering basal insulin in combination with bolus insulin, repeated and regular lower doses of bolus insulin may be administered in place of the long-acting basal insulin, and bolus insulin may be administered postprandially as needed.

Currently, regular subcutaneously injected insulin is recommended to be dosed at 30 to 45 minutes prior to mealtime. As a result, diabetic patients and other insulin users must engage in considerable planning of their meals and of their insulin administrations relative to their meals. Unfortunately, intervening events that may take place between administration of insulin and ingestion of the meal may affect the anticipated glucose excursions.

Furthermore, there is also the potential for hypoglycemia if the administered insulin provides a therapeutic effect over too great a time, e.g., after the rise in glucose levels that occur as a result of ingestion of the meal has already been lowered. Accordingly, in one aspect of any of the methods disclosed herein, the present invention includes a method for reducing the risk of the patient developing hypoglycemia by reducing the average daily dose of insulin administered to the patient by about 5% to about 50% after starting PEGylated C-peptide therapy. In another aspect, the dose of insulin administered is reduced by about 5% to about 45% compared to the patient's insulin dose prior to starting PEGylated C-peptide treatment. In another aspect, the dose of insulin administered is reduced by about 5% to about 40% compared to the patient's insulin dose prior to starting PEGylated C-peptide treatment. In another aspect, the dose of insulin administered is reduced by about 5% to about 35% compared to the patient's insulin dose prior to starting PEGylated C-peptide treatment. In another aspect, the dose of insulin administered is reduced by about 5% to about 30% compared to the patient's insulin dose prior to starting PEGylated C-peptide treatment. In another aspect, the dose of insulin administered is reduced by about 5% to about 25% compared to the patient's insulin dose prior to starting PEGylated C-peptide treatment. In another aspect, the dose of insulin administered is reduced by about 5% to about 20% compared to the patient's insulin dose prior to starting PEGylated C-peptide treatment. In another aspect, the dose of insulin administered is reduced by about 5% to about 15% compared to the patient's insulin dose prior to starting PEGylated C-peptide treatment. In another aspect, the dose of insulin administered is reduced by about 5% to about 10% compared to the patient's insulin dose prior to starting PEGylated C-peptide treatment.

In another aspect, the dose of insulin administered is reduced by about 2% to about 10% compared to the patient's insulin dose prior to starting PEGylated C-peptide treatment. In another aspect, the dose of insulin administered is reduced by about 2% to about 15% compared to the patient's insulin dose prior to starting PEGylated C-peptide treatment. In another aspect, the dose of insulin administered is reduced by about 2% to about 20% compared to the patient's insulin dose prior to starting PEGylated C-peptide treatment.

In another aspect, the dose of insulin administered is reduced by about 10% to about 50% compared to the patient's insulin dose prior to starting PEGylated C-peptide treatment. In another aspect, the dose of insulin administered is reduced by about 10% to about 45% compared to the patient's insulin dose prior to starting PEGylated C-peptide treatment. In another aspect, the dose of insulin administered is reduced by about 10% to about 40% compared to the patient's insulin dose prior to starting PEGylated C-peptide treatment. In another aspect, the dose of insulin administered is reduced by about 10% to about 35% compared to the patient's insulin dose prior to starting C-peptide treatment. In another aspect, the dose of insulin administered is reduced by about 10% to about 30% compared to the patient's insulin dose prior to starting PEGylated C-peptide treatment. In another aspect, the dose of insulin administered is reduced by about 10% to about 25% compared to the patient's insulin dose prior to starting PEGylated C-peptide treatment. In another aspect, the dose of insulin administered is reduced by about 10% to about 20% compared to the patient's insulin dose prior to starting PEGylated C-peptide treatment. In another aspect, the dose of insulin administered is reduced by at least 10% compared to the patient's insulin dose prior to starting PEGylated C-peptide treatment.

In one aspect of any of these methods, the dose of short-acting insulin administered is selectively reduced by any of the prescribed ranges listed above. In another aspect of any of these methods, the dose of intermediate-acting insulin administered is selectively reduced by any of the prescribed ranges. In one aspect of any of these methods, the dose of long-acting insulin administered is selectively reduced by any of the prescribed ranges listed above.

In another aspect of any of these methods, the dose of intermediate- and long-acting insulin administered is independently reduced by any of the prescribed ranges listed above, while the dose of short-acting insulin remains substantially unchanged.

In one aspect of these methods, the dose of short-acting insulin administered is reduced by about 5% to about 50% compared to the patient's insulin dose prior to starting PEGylated C-peptide treatment. In another embodiment, the dose of short-acting insulin administered is reduced by about 5% to about 35% compared to the patient's insulin dose prior to starting PEGylated C-peptide treatment. In another embodiment, the dose of short-acting insulin administered is reduced by about 10% to about 20% compared to the patient's insulin dose prior to starting PEGylated C-peptide treatment. In one aspect of these methods, the dose of short-acting insulin administered preprandially for a meal is reduced. In another aspect of these methods, the dose of short-acting insulin administered in the morning or at nighttime is reduced. In another aspect of any of these methods, the dose of short-acting insulin administered is reduced while the dose of long-acting and/or intermediate-acting insulin administered to the patient is substantially unchanged.

In another aspect of any of the methods disclosed herein, the present invention includes a method for reducing the risk of the patient developing hypoglycemia by reducing the average daily dose of intermediate-acting insulin administered to the patient by about 5% to about 35% after starting PEGylated C-peptide therapy. In one aspect of these methods, the dose of intermediate-acting insulin administered is reduced by about 5% to about 50% compared to the patient's insulin dose prior to starting PEGylated C-peptide treatment. In another embodiment, the dose of intermediate-acting insulin administration is reduced by about 5% to about 35% compared to the patient's insulin dose prior to starting PEGylated C-peptide treatment. In another embodiment, the dose of intermediate-acting insulin administered is reduced by about 10% to about 20% compared to the patient's insulin dose prior to starting PEGylated C-peptide treatment. In another aspect of these methods, the dose of intermediate-acting insulin administered in the morning or at nighttime is reduced. In another aspect of any of these methods, the dose of intermediate-acting insulin administered is reduced while the dose of short-acting insulin administered to the patient is substantially unchanged.

In another aspect of any of the methods disclosed herein, the present invention includes a method for reducing the risk of the patient developing hypoglycemia by reducing the average daily dose of long-acting insulin administered to the patient by about 5% to about 50% after starting PEGylated C-peptide therapy. In one embodiment, the dose of long-acting insulin administered is reduced by about 5% to about 35% compared to the patient's insulin dose prior to starting PEGylated C-peptide treatment. In another embodiment, the dose of long-acting insulin administered is reduced by about 10% to about 20% compared to the patient's insulin dose prior to starting PEGylated C-peptide treatment. In another aspect of these methods, the dose of long-acting insulin administered in the morning or at nighttime is reduced. In another aspect of any of these methods, the dose of long-acting insulin administered is reduced while the dose of short-acting insulin administered to the patient is substantially unchanged.

In certain preferred embodiments, the patient achieves improved insulin utilization and insulin sensitivity while experiencing a reduced risk of developing hypoglycemia after treatment with PEGylated C-peptide as compared with baseline levels prior to treatment. Preferably, the improved insulin utilization and insulin sensitivity are measured by a statistically significant decline in HOMA (Homeostasis Model Assessment) (Turner et al.: *Metabolism* 28(11): 1086-1096, (1979)).

Subcutaneous administration of the PEGylated C-peptide will typically not be into the same site as that most recently used for insulin administration, i.e. PEGylated C-peptide and insulin will be injected into different sites. Specifically in one aspect, the site of PEGylated administration will typically be at least about 10 cm way from the site most recently used for insulin administration. In another aspect, the site of PEGylated C-peptide administration will typically be at least about 15 cm away from the site most recently used for insulin administration. In another aspect, the site of PEGylated C-peptide administration will typically be at least about 20 cm away from the site most recently used for insulin administration.

Examples of different sites include for example, and without limitation, injections into the left and right arm, or injections into the left and right thigh, or injections into the left or right buttock, or injections into the opposite sides of the abdomen. Other obvious variants of different sites include injections in an arm and thigh, or injections in an arm and buttock, or injections into an arm and abdomen, etc.

Moreover one of ordinary skill in the art, i.e., a physician, or diabetic patient, will recognize and understand how to inject PEGylated C-peptide and insulin into any other combination of different sites, based on the prior art teaching, and numerous text books and guides on insulin administration that provide disclosure on how to select different insulin injection sites. See for example, the following representative text books (Learning to live well with diabetes, Ed. Cheryl Weiler, (1991) DCI Publishing, Minneapolis, Minn.; American Diabetes Association Complete Guide to Diabetes, ISBN 0-945448-64-3 (1996)).

In one aspect of any of the claimed methods, PEGylated C-peptide is administered to the opposite side of the abdomen to the site most recently used for insulin administration, approximately 15 to 20 cm apart.

In one aspect, the positively charged ion may be a divalent metal ion. In one aspect, the metal ion is selected from calcium, magnesium, and zinc.

In further embodiments, the amount of PEGylated C-peptide administered is about 0.1 mg, about 0.2 mg, about 0.3 mg, about 0.4 mg, about 0.5 mg, about 0.6 mg, about 0.7 mg, about 0.8 mg, about 0.9 mg, about 1.0 mg, about 1.1 mg, about 1.2 mg, about 1.3 mg, about 1.4 mg, about 1.5 mg, about 1.6 mg, about 1.7 mg, about 1.8 mg, about 1.9 mg, about 2.0 mg, about 2.1 mg, about 2.2 mg, about 2.3 mg, about 2.4 mg, about 2.5 mg, about 2.6 mg, about 2.7 mg, about 2.8 mg, about 2.9 mg, about 3.0 mg, about 3.1 mg, about 3.2 mg, about 3.3 mg, about 3.4 mg, about 3.5 mg, about 3.6 mg, about 3.7 mg, about 3.8 mg, about 3.9 mg, about 4.0 mg, about 4.1 mg, about 4.2 mg, about 4.3 mg, about 4.4 mg, about 4.5 mg, about 4.6 mg, about 4.7 mg, about 4.8 mg, about 4.9 mg, about 5.0 mg, between about 0.1 mg and about 0.5 mg, between about 0.3 mg and about 0.7 mg, between about 0.5 mg and about 0.9 mg, between about 0.7 mg and about 1.1 mg, between about 0.9 mg and about 1.3 mg, between about 1.1 mg and about 1.5 mg, between about 1.3 mg and about 1.7 mg, between about 1.5 mg and about 1.9 mg, between about 1.7 mg and about 2.1 mg, between about 1.9 mg and about 2.3 mg, between about 2.1 mg and about 2.5 mg, between about 2.3 mg and about 2.7 mg, between about 2.5 mg and about 2.9 mg, between about 2.7 mg and about 3.1 mg, between about 2.9 mg and about 3.3 mg, between about 3.1 mg and about 3.5 mg, between about 3.3 mg and about 3.7 mg, between about 3.5 mg and about 3.9 mg, between about 3.7 mg and about 4.1 mg, between about 3.9 mg and about 4.3 mg, between about 4.1 mg and about 4.5 mg, between about 4.3 mg and about 4.7 mg, between about 4.5 mg and about 5.0 mg, between about 5 mg and about 6 mg, between about 6 mg and about 7 mg, between about 7 mg and about 8 mg, between about 8 mg and about 9 mg, between about 9 mg and about 10 mg, between about 10 mg and about 11 mg, between about 11 mg and about 12 mg, between about 12 mg and about 13 mg, between about 13 mg and about 14 mg, or between about 14 mg and about 15 mg.

In further embodiments, the amount of PEGylated C-peptide administered as a loading dose is 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, 5.0 mg, between about 0.1 mg and about 0.5 mg, between about 0.3 mg and about 0.7 mg, between about 0.5 mg and about 0.9 mg, between about 0.7 mg and about 1.1 mg, between about 0.9 mg and about 1.3 mg, between about 1.1 mg and about 1.5 mg, between about 1.3 mg and about 1.7 mg, between about 1.5 mg and about 1.9 mg, between about 1.7 mg and about 2.1 mg, between about 1.9 mg and about 2.3 mg, between about 2.1 mg and about 2.5 mg, between about 2.3 mg and about 2.7 mg, between about 2.5 mg and about 2.9 mg, between about 2.7 mg and about 3.1 mg, between about 2.9 mg and about 3.3 mg, between about 3.1 mg and about 3.5 mg, between about 3.3 mg and about 3.7 mg, between about 3.5 mg and about 3.9 mg, between about 3.7 mg and about 4.1 mg, between about 3.9 mg and about 4.3 mg, between about 4.1 mg and about 4.5 mg, between about 4.3 mg and about 4.7 mg, or between about 4.5 mg and about 4.9 mg, between about 5 mg and about 6 mg, between about 6 mg and about 7 mg, between about 7 mg and about 8 mg, between about 8 mg and about 9 mg, between about 9 mg and about 10 mg, between about 10 mg and about 12 mg, between about 12 mg and about 14 mg, between about 14 mg and about 16 mg, between about 16 mg and about 18 mg, between about 18 mg and about 20 mg, between about 20 mg and about 22 mg, between about 22 mg and about 24 mg, between about 24 mg and about 26 mg, between about 26 mg and about 28 mg, or between about 28 mg and about 30 mg.

In further embodiments, the amount of PEGylated C-peptide administered as a maintenance dose is 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, 5.0 mg, between about 0.1 mg and about 0.5 mg, between about 0.3 mg and about 0.7 mg, between about 0.5 mg and about 0.9 mg, between about 0.7 mg and about 1.1 mg, between about 0.9 mg and about 1.3 mg, between about 1.1 mg and about 1.5 mg, between about 1.3 mg and about 1.7 mg, between about 1.5 mg and about 1.9 mg, between about 1.7 mg and about 2.1 mg, between about 1.9 mg and about 2.3 mg, between about 2.1 mg and about 2.5 mg, between about 2.3 mg and about 2.7 mg, between about 2.5 mg and about 2.9 mg, between about 2.7 mg and about 3.1 mg, between about 2.9 mg and about 3.3 mg, between about 3.1 mg and about 3.5 mg, between about 3.3 mg and about 3.7 mg, between about 3.5 mg and about 3.9 mg, between about 3.7 mg and about 4.1 mg, between about 3.9 mg and about 4.3 mg, between about 4.1 mg and about 4.5 mg, between about 4.3 mg and about 4.7 mg, or between about 4.5 mg and about 5.0 mg.

In further embodiments, the PEGylated C-peptide is administered by continuous infusion, four times daily, three times daily, twice daily, daily, every 2 days, every 3 days, every 4 days, every 5 days, every 6 days, every 7 days, every 8 days, every 9 days, every 10 days, every 11 days, every 12 days, every 13 days, every 14 days, every 15 days, every 16 days, every 17 days, every 18 days, every 19 days, every 20 days, every 21 days, every 22 days, every 23 days, every 24 days, every 25 days, every 26 days, every 27 days, every 28 days, every 29 days, every 30 days, every 31 days, or monthly.

The PEGylated C-peptide may be administered at any time during the day. For humans, the total dosage (weekly) may range from about 0.1 to about 200 mg/week of PEGylated C-peptide, e.g., from about 0.1 mg/week, about 0.2 mg/week, about 0.3 mg/week, about 0.4 mg/week, about 0.5 mg/week, about 0.6 mg/week, about 0.7 mg/week, about 0.8 mg/week, about 0.9 mg/week, about 1.0 mg/week, about 1.1 mg/week, about 1.2 mg/week, about 1.3 mg/week, about 1.4 mg/week, about 1.5 mg/week, about 1.6 mg/week, about 1.7 mg/week, about 1.8 mg/week, about 1.9 mg/week, about 2.0 mg/week, about 2.1 mg/week, about 2.2 mg/week, about 2.3 mg/week, about 2.4 mg/week, about 2.5 mg/week, about 2.6 mg/week, about 2.7 mg/week, about 2.8 mg/week, about 2.9 mg/week, about 3.0 mg/week, about 3.1 mg/week, about 3.2 mg/week, about 3.3 mg/week, about 3.4 mg/week, about 3.5 mg/week, about 3.6 mg/week, about 3.7 mg/week, about 3.8 mg/week, about 3.9 mg/week, about 4.0 mg/week, about 4.1 mg/week, about 4.2 mg/week, about 4.3 mg/week, about 4.4 mg/week, about 4.5 mg/week, about 4.6 mg/week, about 4.7 mg/week, about 4.8 mg/week, about 4.9 mg/week, about 5.0 mg/week, about 5.5 mg/week, about 6 mg/week, about 7 mg/week, about 8 mg/week, about 9 mg/week, about 10 mg/week, about 12 mg/week, about 15 mg/week, about 18 mg/week, about 21 mg/week, about 24 mg/week, about 27 mg/week, about 30 mg/week, about 33 mg/week, about 36 mg/week, about 39 mg/week, about 42 mg/week, about 45 mg/week, about 50 mg/week, about 60 mg/week, about 70 mg/week, about 80 mg/week, about 90 mg/week, about 100 mg/week, about 110 mg/week, about 120 mg/week, about 130 mg/week, about 140 mg/week, about 150 mg/week, about 160 mg/week, about 170 mg/week, about 180 mg/week, about 190 mg/week, about 200 mg/week, between about 0.1 mg/week and about 0.5 mg/week, between about 0.3 mg/week and about 0.7 mg/week, between about 0.5 mg/week and about 0.9 mg/week, between about 0.7 mg/week and about 1.1 mg/week, between about 0.9 mg/week and about 1.3 mg/week, between about 1.1 mg/week and about 1.5 mg/week, between about 1.3 mg/week and about 1.7 mg/week, between about 1.5 mg/week and about 1.9 mg/week, between about 1.7 mg/week and about 2.1 mg/week, between about 1.9 mg/week and about 2.3 mg/week, between about 2.1 mg/week and about 2.5 mg/week, between about 2.3 mg/week and about 2.7 mg/week, between about 2.5 mg/week and about 2.9 mg/week, between about 2.7 mg/week and about 3.1 mg/week, between about 2.9 mg/week and about 3.3 mg/week, between about 3.1 mg/week and about 3.5 mg/week, between about 3.3 mg/week and about 3.7 mg/week, between about 3.5 mg/week and about 3.9 mg/week, between about 3.7 mg/week and about 4.1 mg/week, between about 3.9 mg/week and about 4.3 mg/week, between about 4.1 mg/week and about 4.5 mg/week, between about 4.3 mg/week and about 4.7 mg/week, between about 4.5 mg/week and about 5.0 mg/week, between about 5.0 and about 10 mg/week, between about 10 and about 20 mg/week, between 20 and about 40 mg/week, between about 40 and about 60 mg/week, between about 60 and about 80 mg/week, between about 80 and about 100 mg/week, between about 100 and about 120 mg/week, between about 120 and about 140 mg/week, between about 140 and about 160 mg/week, between about 160 and about 180 mg/week, and between about 180 and about 200 mg/week.

Preferably the total weekly dose used of PEGylated C-peptide is about 0.8 mg to about 3.5 mg, about 1 mg to about 20 mg, about 20 mg to about 50 mg, about 50 mg to about 100 mg, about 100 mg to about 150 mg, or about 150 mg to about 200 mg.

The total weekly dose of PEGylated C-peptide may be about 0.1 mg, about 0.5 mg, about 0.8 mg, about 1 mg, about 1.5 mg, about 2 mg, about 2.5 mg, about 3 mg, about 3.5 mg, about 4 mg, about 4.5 mg, about 5 mg, about 5.5 mg, about 6 mg, about 7 mg, about 8 mg, about 9 mg, about 10 mg, about 12 mg, about 15 mg, about 18 mg, about 21 mg, about 24 mg, about 27 mg, about 30 mg, about 33 mg, about 36 mg, about 39 mg, about 42 mg, about 45 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, or about 200 mg. (It will be appreciated that masses of PEGylated C-peptide referred to above are dependent on the bioavailability of the delivery system and based on the use of PEGylated C-peptide with a molecular mass of approximately 40,000 Da.)

V. Pharmaceutical Compositions

In one aspect, the present invention includes a pharmaceutical composition comprising PEGylated C-peptide, and a pharmaceutically acceptable carrier, diluent or excipient.

Pharmaceutical compositions suitable for the delivery of PEGylated C-peptide and methods for their preparation will be readily apparent to those skilled in the art and may comprise any of the known carriers, diluents, or excipients. Such compositions and methods for their preparation may be found, e.g., in *Remington's Pharmaceutical Sciences,* 19th Edition (Mack Publishing Company, 1995).

In one aspect, the pharmaceutical compositions may be in the form of sterile aqueous solutions and/or suspensions of the pharmaceutically active ingredients, aerosols, ointments, and the like. Formulations which are aqueous solutions are most preferred. Such formulations typically contain the PEGylated C-peptide itself, water, and one or more buffers which act as stabilizers (e.g., phosphate-containing buffers) and optionally one or more preservatives or antioxidants such as BHT. Such formulations containing, e.g., about 0.5 to 200 mg, about 0.5 to 100 mg, about 0.5 to 80 mg, about 0.5 to 60 mg, about 0.5 to 40 mg, about 0.5 to 30 mg, about 0.3 to 3.3 mg, about 1 to 3.3 mg, about 1 to 2 mg, about 1 to 3.3 mg, about 2 to 3.3 mg or any of the ranges mentioned herein, e.g., about 200 mg, about 150 mg, about 120 mg, about 100 mg, about 80 mg, about 60 mg, about 50 mg, about 40 mg, about 30 mg, about 20 mg, or about 10 mg, or about 8 mg, or about 6 mg, or about 5 mg, or about 4 mg, or about 3 mg, or about 2 mg, or about 1 mg, or about 0.5 mg of the PEGylated C-peptide and constitute a further aspect of the invention.

Pharmaceutical compositions may include pharmaceutically acceptable salts of PEGylated C-peptide. For a review on suitable salts, see *Handbook of Pharmaceutical Salts: Properties, Selection, and Use* by Stahl and Wermuth (Wiley-VCH, 2002). Suitable base salts are formed from bases which form non-toxic salts. Representative examples include the aluminium, arginine, benzathine, calcium, choline, diethylamine, diolamine, glycine, lysine, magnesium, meglumine, olamine, potassium, sodium, tromethamine, and zinc salts. Hemisalts of acids and bases may also be formed, e.g., hemisulphate and hemicalcium salts. In one embodiment, PEGylated C-peptide may be prepared as a gel with a pharmaceutically acceptable positively charged ion.

In one aspect, the positively charged ion may be a monovalent metal ion. In one aspect, the metal ion is selected from sodium and potassium.

The dose may or may not be in solution. If the dose is administered in solution, it will be appreciated that the volume of the dose may vary, but will typically be 20 µL-2 mL. Preferably the dose for S.C. administration will be given in a volume of 2000 µL, 1500 µL, 1200 µL, 1000 µL, 900 µL, 800 µL, 700 µL, 600 µL, 500 µL, 400 µL, 300 µL, 200 µL, 100 µL, 50 µL, or 20 µL.

PEGylated C-peptide doses in solution can also comprise a preservative and/or a buffer. For example, the preservatives m-cresol, or phenol can be used. Typical concentrations of preservatives include 0.5 mg/mL, 1 mg/mL, 2 mg/mL, 3 mg/mL, 4 mg/mL, or 5 mg/mL. Thus, a range of concentration of preservative may include 0.2 to 10 mg/mL, particularly 0.5 to 6 mg/mL, or 0.5 to 5 mg/mL. Examples of buffers that can be used include histidine (pH 6.0), sodium phosphate buffer (pH 6 to 7.5), or sodium bicarbonate buffer (pH 7 to 7.5). It will be appreciated that the PEGylated C-peptide dose may comprise one or more of a native or intact C-peptide, fragments, derivatives, or other functionally equivalent variants of C-peptide.

PEGylated C-peptide doses in solution can also comprise an antioxidant and/or a buffer. For example, the antioxidants butylated hydroxytoluene (BHT) can be used. Concentrations of antioxidants include 0.005%-0.03% BHT. It will be appreciated that the PEGylated C-peptide dose may comprise one or more of a native or intact C-peptide, fragments, derivatives, or other functionally equivalent variants of C-peptide.

Pharmaceutical compositions to be used in the invention suitable for parenteral administration are typically sterile aqueous solutions and/or suspensions of the pharmaceutically active ingredients preferably made isotonic with the blood of the recipient. Such compositions generally comprise excipients, salts, carbohydrates, and buffering agents (preferably to a pH of from 3 to 9), such as sodium chloride, glycerin, glucose, mannitol, sorbitol, and the like.

For some applications, pharmaceutical compositions for parenteral administration may be suitably formulated as a sterile non-aqueous solution or as a dried form to be used in conjunction with a suitable vehicle such as sterile, pyrogen-free water. The preparation of parenteral formulations under sterile conditions, e.g., by lyophilization, may readily be accomplished using standard pharmaceutical techniques well-known to those skilled in the art.

Pharmaceutical compositions of PEGylated C-peptide for parenteral administration may be administered directly into the blood stream, into muscle, or into an internal organ. Suitable means for parenteral administration include intravenous, intra-arterial, intraperitoneal, intrathecal, intraventricular, intraurethral, intrasternal, intracranial, intramuscular, intrasynovial, and subcutaneous. Suitable devices for parenteral administration include needle (including microneedle) injectors, needle-free injectors, and infusion techniques.

Subcutaneous administration of PEGylated C-peptide will typically not be into the same site as that most recently used for insulin administration. In one aspect of any of the claimed methods and pharmaceutical compositions, PEGylated C-peptide is administered to the opposite side of the abdomen to the site most recently used for insulin administration. In another aspect of any of the claimed methods and pharmaceutical compositions, PEGylated C-peptide is administered to the upper arm. In another aspect of any of the claimed methods and pharmaceutical compositions, PEGylated C-peptide is administered to the abdomen. In another aspect of any of the claimed methods and pharmaceutical compositions, PEGylated C-peptide is administered to the upper area of the buttock. In another aspect of any of the claimed methods and pharmaceutical compositions, PEGylated C-peptide is administered to the front of the thigh.

EXAMPLES

Abbreviations. The following abbreviations have been used in the specification and examples: ACN=acetonitrile; Bzl=Bn=benzyl; DIEA=N,N-diisopropylethylamine; DMF=N,N-dimethylformamide; tBu=tert-butyl; OtBu=tert-butoxy; TSTU=O—(N-succinimidyl)-1,1,3,3-tetramethyluronium tetrafluoroborate; THF=tetrahydrofuran; EtOAc=ethyl acetate; DIPEA=DIEA=diisopropylethylamine; HOAt=1-hydroxy-7-azabenzotriazole; HOBt=1-hydroxy-benzotriazole; NMP=N-methylpyrrolidin-2-one; TEA=triethyl amine; SA=sinapinic acid; Su=1-succinimidyl=2,5-dioxo-pyrrolidin-1-yl; TFA=trifluoroacetic acid; DCM=dichloromethane; DMSO=dimethyl sulphoxide; RT=room temperature; Fmoc=fluorenylmethyloxycarbonyl; Trt=triphenylmethyl; DIC=N,N'-diisopropylcarbodiimide; NMM=N-methylmorpholine; TIS=triisopropylsilane; EtOH=ethanol;

General Procedures: The following examples and general procedures refer to intermediate compounds and final products identified in the specification. Alternatively, other reactions disclosed herein or otherwise conventional will be applicable to the preparation of the corresponding compounds of the invention. In all preparative methods, all starting materials are known or may easily be prepared from known starting materials. All temperatures are set forth in degrees Celsius (° C.) and unless otherwise indicated, all parts and percentages are by weight (i.e., w/w) when referring to yields and all parts are by volume (i.e., v/v) when referring to solvents and eluents.

Example 1

GMP Batch Preparation of PEGylated C-Peptide (CBX129801)

Overview

Human C-peptide (EAEDLQVGQVELGGGPGAGSLQPLALEGSLQ) (SEQ. ID. No. 1)

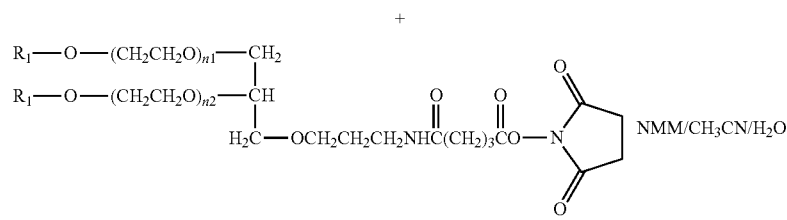

1. Purification/Desalting/Ion Exchange chromatography/Desalting
2. Lypophilization

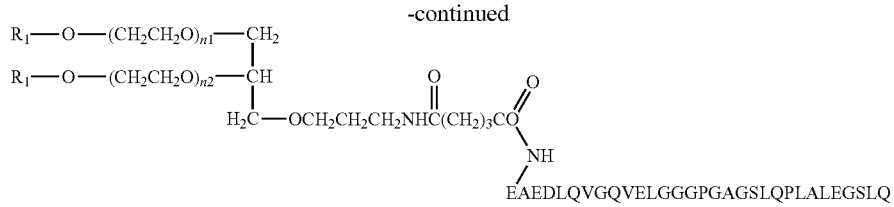

C-Peptide Synthesis:

The solid phase peptide synthesis (SPPS) is performed according to standard procedures and well-developed protocols as described below. SPPS is the sequential synthesis of a peptide chain anchored on a solid support by repetition of a cycle encompassing the following steps: removal of the N-terminal protecting group of the last amino acid added; wash; coupling of the activated amino acid; capping by acetylation; wash. This cycle is repeated until the sequence of the desired peptide is synthesized as described below.

The synthesis of C-peptide (CBX129800) is carried out following the general solid-phase procedure outlined above in which the α-amino group of each amino acid is protected with the base-sensitive 9-fluorenylmethyloxycarbonyl (Fmoc) group while side chain functional groups are protected with acid-labile groups, except the C-terminal Gln which is attached to the solid support by activation of the α-carboxyl group of glutamic acid protected at the α-carboxyl group with an acid-labile group. All amino acids have side chain standard protection groups: Glu(O-t-Bu), Glu-O-t-Bu, Ser(t-Bu), Gln(Trt), and Asp(O-t-Bu). The amino acids Ala, Leu, Gly, Pro, and Val have no side chain protection.

The Fmoc-Rink-OH linker is first coupled to the resin with DIC/HOBt, DMF to obtain the Fmoc-Rink-amide resin. The peptide is then assembled by Fmoc-SPPS on the Fmoc-Rink-amide resin. The couplings are performed in DMF with variable amino acid equivalents using diisopropylcarbodiimide/1-hydroxybenzotriazole (DIC/HOBt) for activation. Couplings can be terminated by capping of un-reacted amino groups, using acetic anhydride and N-methylmorpholine (NMM). After each coupling, the Fmoc group is removed with piperidine in DMF before the next coupling. The final protected CBX129800 peptide resin is washed and dried.

Process monitoring, using the ninhydrin/Kaiser or chloranil test are performed at the end of each synthesis cycle as an evaluation step. These are color tests measuring residual resin-bound amino groups (negative test result indicates absence of free amines). The process can then proceed to the next coupling step. The intensity of a positive test result dictates which alternate step is to be executed. If the test indicates incomplete coupling, prolonged or re-coupling of the Fmoc-amino acid is performed. Blocking of any remaining free amine sites by acetic anhydride in the presence of a tertiary amine is performed last.

The crude peptide is cleaved from the resin by treatment with TFA in the presence of scavengers (water and TIS). This results in the concomitant cleavage of the peptide from the resin as well as the removal of the side chain protecting groups from the peptide. This mixture is then neutralized with an aqueous solution of ammonium acetate. The resin is filtered off, producing the crude peptide as a solution.

The crude intermediate peptide is purified by preparative, reverse-phase HPLC techniques, on $C_{18}$ reverse-phase silica using a three-stage procedure (RPC 1, RPC 2, and RPC 3) during which the purity of the fractions is assessed by analytical HPLC. The combined fractions are concentrated, filtered, and lyophilized.

The crude CBX129800 peptide solution is pre-treated by filtration.

Purification by Preparative Reversed Phase Chromatography (RPC 1)

The crude CBX129800 solution is purified by preparative RPC using reversed phase silica or equivalent based packing material. The peptide adsorbed is eluted from the column by applying an aqueous solution containing ethanol and ammonium acetate buffer (ambient temperature).

Purification by Preparative Reversed Phase Chromatography (RPC 2)

The combined fractions from RPC 1 are purified by preparative RPC using reversed phase silica or equivalent based packing material. The peptide adsorbed is eluted from the column by applying an aqueous solution containing ethanol and aqueous ammonium acetate buffer (ambient temperature).

Counter Ion Exchange by Preparative Reversed Phase Chromatography (RPC 3)

Counter ion exchange is performed on the combined fractions from RPC 2 by preparative HPLC using reversed phase silica, or equivalent packing material, pre-equilibrated with aqueous sodium acetate and ethanol. The peptide adsorbed is first washed with a sodium acetate/ethanol buffer then with water and ethanol before being eluted from the column by applying an aqueous solution containing ethanol (ambient temperature).

Prior to lyophilization, the peptide pool is concentrated. The concentrated solution is filtered and lyophilized to the final CBX129800 sodium salt. It is then packaged in high density polyethylene (HDPE) container with polypropylene (PP) screw cap and the bottle placed in an aluminum barrier foil and sealed by heat.

PEGylation:

The synthesis of the human PEGylated C-peptide was carried out in a single step by coupling of the N-terminus of the human C-peptide (sodium salt) with the branched, approx. 40 kDa-NHS ester PEG derivative (SUNBRIGHT GL2-400GS2 (NOF Corporation)) in the presence of NMM.

SUNBRIGHT GL2-400GS2 (115 g) is first dissolved in 600 mL of a solution of (50/50) acetonitrile/water. The resulting solution was stirred and charged with another solution containing human C-peptide (7.9 g) in a solution of 175 mL of acetonitrile/water, followed by addition of 1.2 mL of NMM. Addition of NMM was repeated several times at ~1 hr intervals, with the progress of the reaction monitored by HPLC prior to each addition. This process was repeated about 8 to 10 times and then the reaction was stirred overnight for about 8 to 12 hrs (In an alternative procedure, the pH of the reaction mixture is monitored and NMM is added as needed to maintain a pH of 8.0 to 8.2). The resulting reaction mixture was carried on to the purification step once the reaction was verified as complete by HPLC analysis. Typically during this process several sub-lots were prepared and then combined for purification as described below.

Purification of Crude PEGylated C-Peptide by Preparative Reversed Phase Chromatography The crude PEGylated C-peptide solution was diluted with 6 volumes in 0.1% TFA/water. The pH was adjusted to a pH of ≤3 and purified by preparative HPLC using reverse phase silica (Diasogel C-18, 15 µm, 300 Angstrom). The adsorbed PEGylated C-peptide was eluted from the column by applying a gradient of ACN in dilute aqueous TFA (Buffer A is 0.1% TFA, Buffer B is 100% ACN: 0 to 25% B in 5 minutes, then 25% to 50% B during 100 minutes and then hold until the product is eluted). The eluate was monitored by UV at 230 nm. Fraction with purity of 90%, no single impurity >6.0% are pooled. Fractions with purity >70% may be recycled.

Desalting and Purification of PEGylated C-Peptide by Preparative Reversed Phase Chromatography The combined pure fractions obtained from the preceding step were desalted and purified by preparative HPLC using reverse phase silica. The column was washed with dilute aqueous TFA, followed by dilute aqueous ammonium acetate. The PEGylated C-peptide was then eluted from the column by applying a gradient of ACN in dilute aqueous AcOH (Buffer A is 2% acetic acid, Buffer B is 100% ACN: 0 to 25% B in 5 minutes, then 25% to 50% B during 75 minutes and then hold until the product is eluted). The eluate was monitored by UV at 230 nm. The pure fractions obtained from chromatography were pooled (purity ≥95%, no single impurity >3.0%) and lyophilized. Fractions with purity >80% maybe recycled for further purification.

Ion Exchange Purification of PEGylated C-Peptide by Preparative HPLC

The crude lyophilized PEGylated human C-peptide from the step above (~180 g) was dissolved in 5% ACN/water and applied to an ion exchange column (DEAE52 Cellulose). The column was then washed with ~50 L of water and the product was eluted off the column with ~40 L of an aqueous solution of sodium chloride (1M)/ammonium acetate (1M). In an alternative procedure, the product is eluted from the column with an aqueous solution of acetic acid in 5% ACN (1% to 5% AcOH). It was found that elution with an aqueous acetic acid gradient resulted in improved removal of free PEG and increased purity of the final product with improved stability to the GMP material based on short-term forced degradation studies. The eluate was monitored by UV at 230 nm. The pure fractions obtained from the chromatography were pooled (≥92% purity; no single impurity >4%) and carried on for desalting/purification. Fractions with purity >80% may be recycled.

Desalting and Purification of CBX129801 by Preparative Reversed Phase Chromatography The pure fractions from the ion exchange chromatography step were diluted with an equal volume of water and applied to a preparative HPLC column (silica). The column was then washed with dilute 2% acetic acid (1 BV) and the product eluted with a solution of ACN in dilute acetic acid (Buffer A is 2% acetic acid, Buffer B is 100% ACN: 0 to 25% B in 5 minutes, then 25% to 50% B during 50 minutes and then hold until the product is eluted). The eluate was monitored by UV at 230 nm. The pure fractions (purity ≥95%, no single impurity >3.0%) obtained from chromatography were pooled and lyophilized. Fractions with purity >80% maybe recycled.

Lyophilization of PEGylated C-Peptide

The product from the preceding purification was reconstituted at a concentration of about 15-20 g/L in 2% aqueous acetic acid and lyophilized to give the pure PEGylated C-peptide drug substance as its free acid.

Example 2

Biophysical Characterization of PEGylated C-Peptide

A reference standard batch of the PEGylated C-peptide prepared similarly to the GMP batch described in Example 1 above, with purity of 99.5%, as determined by RP-HPLC with UV detection, was used in the analytical investigations described below unless noted otherwise. The structural studies conducted are listed in Table E1. All analyses confirm the chemical structure of the drug substance.

TABLE E1

Structural testing performed

| Test | Analytical Technique |
|---|---|
| Molecular mass | MALDI-TOF MS |
| Identity | FT-IR |
| Identity and ratios of individual amino acids | Amino acid analysis for DS |
| Identity and chirality of individual amino acids | Chiral amino acid analysis |
| Molecular mass and sequence of amino acids (performed at the C-peptide stage) | CID-MS/MS |
| Peptide Mapping (to confirm sequence on PEGylated peptide) | Chymotrysin digest followed by HPLC and MS/MS analysis of fragments |
| Absence of Counter ion | Ion chromatography, RP-HPLC, ICP-MS |

Molecular Mass by MS:

Matrix Assisted Laser Desorption Ionization-Time of Flight (MALDI-TOF) was used to verify the molecular mass of the drug substance. The sample gave a positive ion MALDI-TOF mass spectrum with a broad singly-charged pseudomolecular ion cluster observed centered approximately at m/z 45743.

Figure 2:
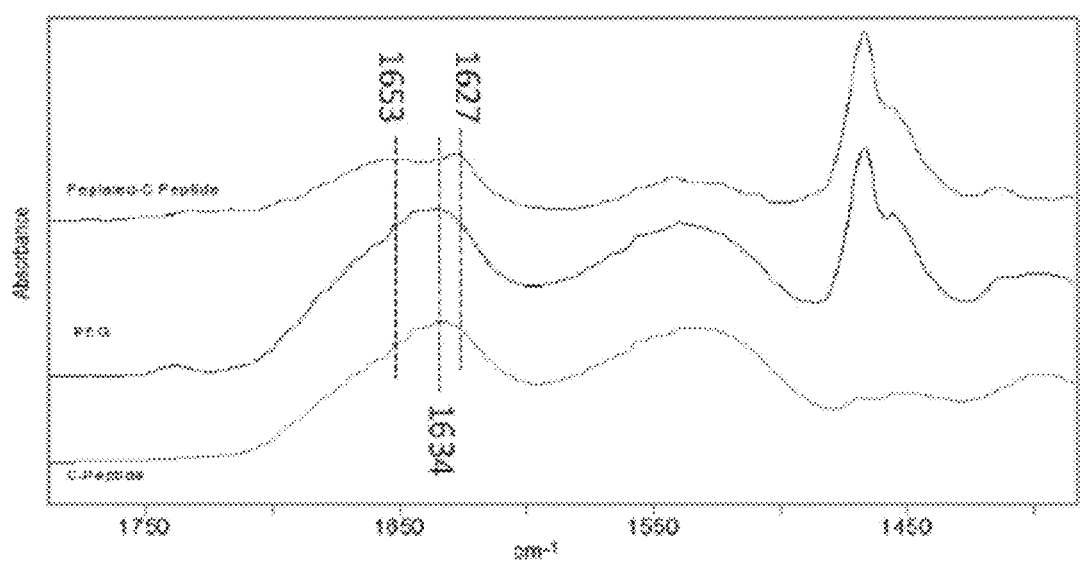
FIG. 2 shows an expanded region of the Fourier Transform Infrared Spectroscopy (FT-IR): of C-peptide, the PEG reagent, and PEGylated C-peptide.

Fourier Transform Infrared Spectroscopy (FT-IR):

FT-IR spectra of C-peptide, the PEG reagent, and PEGylated C-peptide were collected on a Jasco 4200 FT-IR spectrometer equipped with a TGS detector and a single-bounce ZnSe crystal mounted on an ATR accessory. Solid samples were pressed against the Zn Se crystal with a Teflon rod. Residual moisture peaks were subtracted from the spectra. The results are shown in FIG. 1 and FIG. 2 (expanded region). The spectrum of PEGylated C-peptide is very similar to the spectra of the PEG reagent. This is not surprising given the mass ratio of peptide to PEG.

However, there is a slight difference in the amide I region as shown in FIG. 2. Specifically, the amide I bands of PEGylated C-peptide show two peaks at 1627 and 1653 $cm^{-1}$, while the spectrum of free C-peptide only exhibits one broad amide I band peak at 1634 $cm^{-1}$. An amide I band near 1630 $cm^{-1}$ is normally associated with β-sheet structures or β-turns, while an amide I band near 1650 $cm^{-1}$ is normally assigned to α-helix, irregular, or random coil structures. The appearance of an absorbance at 1653 $cm^{-1}$ is consistent with a more random structure for the PEGylated peptide compared to C-peptide.

Figure 3:
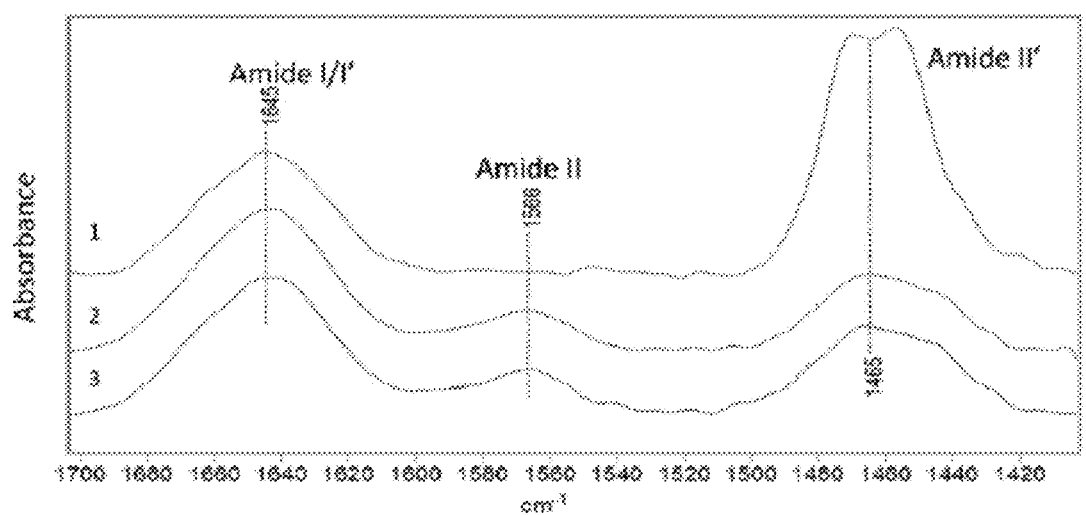
FIG. 3 shows a Fourier Transform Infrared Spectroscopy (FT-IR): of C-peptide, the PEG reagent, and PEGylated C-peptide collected in $D_2O$.
Figure 4:
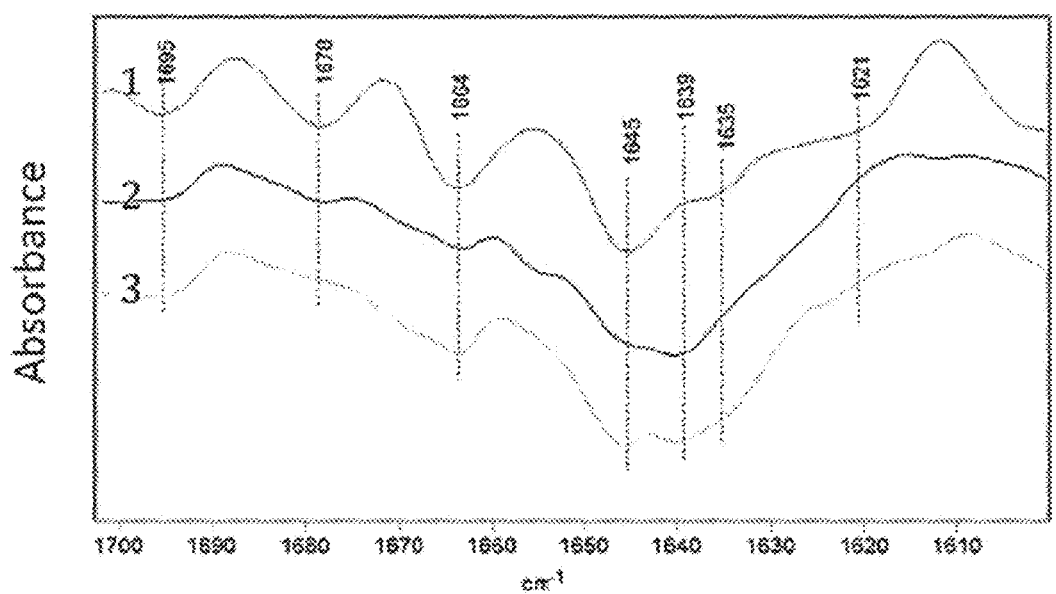
FIG. 4 shows a Fourier Transform Infrared Spectroscopy (FT-IR): of C-peptide, the PEG reagent, and PEGylated C-peptide collected in $D_2O$.

To investigate if the difference in the amide I region is due to differences in hydrogen bonding between amide groups and solvent water, the FT-IR spectra were collected in $D_2O$ as shown in FIG. 3 and FIG. 4. For the collection of $D_2O$ spectra, sample in $D_2O$ solution was placed between two $CaF_2$ windows with a 6 µm spacer.

The FT-IR spectrum of PEGylated C-peptide in $D_2O$ shows minimum amide II band intensity (at 1566 $cm^{-1}$), which indicates all amide groups undergo H-D exchange. Upon H-D exchange, the amide II band is shifted from 1566 to 1465 cm$^{-1}$ (becomes an amide II' band). There is remaining amide II intensity for free C-peptide at both higher (~25 mg/mL) and lower concentrations (~12.5 mg/mL) in D$_2$O, which indicates some un-exchanged amide groups. The un-exchanged amide groups are likely protected by either intramolecular hydrogen bonds within beta-turns or inter-molecular hydrogen bonds formed among peptide oligomers (aggregates) at high concentration. For the PEGylated C-peptide in D$_2$O, the effective C-peptide concentration is much lower because of the low mass ratio of C-peptide to the 40 kDa PEG.

However, as can be seen from the second derivative FT-IR spectra (shown in FIG. 4), the amide I' band for the high concentration sample of C-peptide (~25 mg/mL) shows a major peak at 1639 cm$^{-1}$, with a shoulder at 1645 cm$^{-1}$, whereas the low concentration sample (~12.5 mg/mL) shows major peaks at both 1639 cm$^{-1}$ and 1645 cm$^{-1}$. This indicates the difference in the amide I' region may be concentration related. In comparison to the spectrum of PEGylated C-peptide, the spectra of free C-peptide shows more intensity near 1635-1640 cm$^{-1}$, indicating more β-turn structures in free C-peptide. It should be noted that signal to noise was poor for more dilute samples of C-peptide samples precluding assessment of lower concentrations.

Identity and Ratio of Individual Amino Acids by Amino Acid Analysis:

To ensure the identity and the correct ratio of the constituent amino acids, amino acid analysis was performed on the PEGylated C-peptide. This method involves hydrolyzing the peptide in strong acid, separating the amino acids on an ion-exchange column, and, finally, detecting the eluents after ninhydrin derivatization. The results of the study are shown in Table E2. The results from the amino acid analysis confirm the identity and theoretical relative occurrence of amino acids in the PEGylated C-peptide within experimental error.

Identity and Chirality of Individual Amino Acids by GC:

TABLE E2

Results of amino acid analysis

| Amino Acid | Theoretical Relative Occurrence | Observed Relative Occurrence |
|---|---|---|
| Asp | 1 | 1.1 |
| Pro | 2 | 2.1 |
| Ser | 2 | 2.2 |
| Glx* | 8 | 6.9 |
| Gly | 7 | 7.3 |
| Ala | 3 | 3.0 |
| Val | 2 | 2.0 |
| Leu | 6 | 6.5 |

Notes:
*Glx = results from Gln + Glu.

Chiral amino acid analysis was performed to investigate the chiral identity of the constituent amino acid residues. The peptide is hydrolyzed in deuterated solvents (DCl/D$_2$O), derivatized as the N(O,S)-fluoroacetyl amino acid esters, and analyzed with GC-MS to determine each amino acid enantiomer. GC was performed using a deactivated glass capillary coated with Chirasil-Val. The carrier gas was hydrogen. The results are shown in Table E3. The values obtained confirm the chirality expected for the amino acids constituting the structure of the PEGylated C-peptide.

TABLE E3

Results of chiral amino acid analysis

| Amino Acid | Content of L-amino Acid (%) |
|---|---|
| Asp | >99.9 |
| Pro | 99.86 |
| Ser | 99.51 |
| Glx | >99.9 |
| Ala | 99.9 |
| Val | >99.9 |
| Leu | 99.89 |

Sequence of Amino Acids by MS/MS:

Given the large size and polydispersity of the PEG, sequencing by MS/MS is performed at the C-peptide stage (prior to PEGylation). The amino acid sequence of C-peptide was investigated by performing MS/MS using CID (Collision Induced Dissociation), a technique in which the intact sample molecule is deliberately fragmented with the intention of gaining structural information from the product ion spectrum created by the process.

The types of fragment ions observed in a MS/MS spectrum depend on many factors including primary sequence, the amount of internal energy, how the energy was introduced, charge state, etc. The accepted nomenclature for fragment ions was first proposed by Roepstorff and Fohlman [*Biomedical Spectrometry*, 1984, 11(11): 601], and subsequently modified by Johnson et al. [*Annals of Chemistry*, 1987, 59(21): 2621-2625].

Fragments will only be detected if they carry at least one charge. If this charge is retained on the N-terminal fragment, the ion is classed as either a, b, or c. If the charge is retained on the C-terminal, the ion type is either x, y, or z. A subscript indicates the number of residues in the fragment.

In addition to the proton(s) carrying the charge, c ions and y ions abstract an additional proton from the precursor peptide. Thus, six singly-charged sequence ion are possible. Note that these structures include a single charge-carrying proton. In electrospray ionization, peptides generally carry two or more charges, so that fragment ions may carry more than one proton.

The expected, multiply-charged b and y and fragment ions were calculated using a computer program developed by Croker et al. [*Journal of Biomolecular Techniques*, 2000, volume 11, issue 3, 135-141]. The results are shown in Tables E4 and E5. Fragmentation and sequence analysis by MS/MS and MS/MS/MS confirmed the suggested primary sequence of the C-peptide.

TABLE E4

Summary of MS Fragmentation and sequence analysis

N-terminal Ion Series

| Sequence Example 2 | Pos. | Expected b$^{1+}$ | Observed m/z | Expected b$^{2+}$ | Observed m/z | Expected b$^{3+}$ | Observed m/z |
|---|---|---|---|---|---|---|---|
| Glu | b1 | 130.1 | — | 65.5 | — | 44 | — |
| Ala | b2 | 201.1 | 201.1 | 101.1 | — | 67.7 | — |
| Glu | b3 | 330.1 | 330.1 | 165.6 | — | 110.7 | — |
| Asp | b4 | 445.2 | 445.1 | 223.1 | — | 149.1 | — |

TABLE E4-continued

Summary of MS Fragmentation and sequence analysis

N-terminal Ion Series

| Sequence Example 2 | Pos. | Expected $b^{1+}$ | Observed m/z | Expected $b^{2+}$ | Observed m/z | Expected $b^{3+}$ | Observed m/z |
|---|---|---|---|---|---|---|---|
| Leu | b5 | 558.2 | 558.2 | 279.6 | — | 186.8 | — |
| Gln | b6 | 686.3 | 686.2 | 343.7 | — | 229.4 | — |
| Val | b7 | 785.4 | 785.3 | 393.2 | — | 262.5 | — |
| Gly | b8 | 842.4 | 842.3 | 421.7 | — | 281.5 | — |
| Gln | b9 | 970.5 | 970.4 | 485.7 | — | 324.2 | — |
| Val | b10 | 1069.5 | 1069.5 | 535.3 | — | 357.2 | — |
| Glu | b11 | 1198.6 | 1198.4 | 599.8 | — | 400.19 | — |
| Leu | b12 | 1311.6 | 1311.6 | 656.3 | — | 437.9 | — |
| Gly | b13 | 1368.7 | 1368.6 | 684.8 | 684.8 | 456.9 | — |
| Gly | b14 | 1425.7 | 1425.6 | 713.4 | 713.3 | 475.9 | — |
| Gly | b15 | 1482.7 | 1482.6 | 741.9 | 741.8 | 494.9 | — |
| Pro | b16 | 1579.8 | — | 790.4 | — | 527.3 | — |
| Gly | b17 | 1636.8 | 1636.8 | 818.9 | 818.8 | 546.3 | — |
| Ala | b18 | 1707.8 | 1707.8 | 854.4 | 854.3 | 569.9 | — |
| Gly | b19 | 1764.8 | 1764.9 | 882.9 | 882.8 | 589 | — |
| Ser | b20 | 1851.9 | 1851.8 | 926.4 | 926.4 | 618 | — |
| Leu | b21 | 1965 | 1964.9 | 983 | 982.9 | 655.7 | — |
| Gln | b22 | 2093 | — | 1047 | 1046.9 | 698.3 | — |
| Pro | b23 | 2190.1 | — | 1095.5 | — | 730.7 | — |
| Leu | b24 | 2303.2 | — | 1152.1 | 1151 | 768.4 | — |
| Ala | b25 | 2374.2 | — | 1187.6 | 1187.5 | 792.1 | — |
| Leu | b26 | 2487.3 | — | 1244.1 | 1244.1 | 829.8 | — |
| Glu | b27 | 2616.3 | — | 1308.7 | 1308.6 | 872.8 | — |
| Gly | b28 | 2673.3 | — | 1337.2 | 1337.1 | 891.8 | — |
| Ser | b29 | 2760.4 | — | 1380.7 | 1380.6 | 920.8 | — |
| Leu | b30 | 2873.5 | — | 1437.2 | 1437.1 | 958.5 | 958.3 |
| Gln | b31 | 3001.5 | — | 1501.3 | 1501.2 | 1001.2 | — |
| OH | — | — | — | — | — | — | — |

TABLE E5

Summary of MS Fragmentation and sequence analysis

C-terminal Ion Series

| Sequence Example 2 | Pos. | Expected $y^{1+}$ | Observed m/z | Expected $y^{2+}$ | Observed m/z | Expected $y^{3+}$ | Observed m/z |
|---|---|---|---|---|---|---|---|
| Glu | y31 | 3019.5 | — | 1510.3 | 1510.3 | 1007.2 | 1007.2 |
| Ala | y30 | 2890.5 | — | 1445.7 | — | 964.2 | — |
| Glu | y29 | 2819.4 | — | 1410.2 | — | 940.5 | — |
| Asp | y28 | 2690.4 | — | 1345.7 | 1345.5 | 897.5 | — |
| Leu | y27 | 2575.4 | — | 1288.2 | 1288.1 | 859.1 | — |
| Gln | y26 | 2462.3 | — | 1231.7 | 1231.5 | 821.4 | — |
| Val | y25 | 2334.2 | — | 1167.6 | 1167.5 | 778.8 | — |
| Gly | y24 | 2235.2 | — | 1118.1 | 1117.9 | 745.7 | — |
| Gln | y23 | 2178.1 | — | 1089.6 | 1089.4 | 726.7 | — |
| Val | y22 | 2050.1 | — | 1025.5 | — | 684 | — |
| Glu | y21 | 1951 | 1951 | 976 | 975.9 | 651 | — |
| Leu | y20 | 1822 | 1821.9 | 911.5 | 911.4 | 908 | — |
| Gly | y19 | 1708.9 | 1708.8 | 855 | — | 570.3 | — |
| Gly | y18 | 1651.9 | 1651.9 | 826.4 | 826.4 | 551.3 | — |
| Gly | y17 | 1594.8 | 1594.9 | 797.9 | 797.8 | 532.3 | — |
| Pro | y16 | 1537.8 | 1537.8 | 769.4 | 769.3 | 513.3 | — |
| Gly | y15 | 1440.8 | — | 720.9 | — | 480.9 | — |
| Ala | y14 | 1383.8 | 1383.7 | 692.4 | — | 461.9 | — |
| Gly | y13 | 1312.7 | 1312.6 | 656.9 | — | 438.2 | — |
| Ser | y12 | 1255.7 | 1255.6 | 928.4 | — | 419.2 | — |
| Leu | y11 | 1168.7 | 1168.6 | 584.8 | — | 390.2 | — |
| Gln | y10 | 1055.6 | 1055.5 | 528.3 | — | 352.5 | — |
| Pro | y9 | 927.5 | 927.5 | 464.3 | — | 309.8 | — |
| Leu | y8 | 830.5 | — | 415.7 | — | 277.5 | — |
| Ala | y7 | 717.4 | 717.3 | 359.2 | — | 239.8 | — |
| Leu | y6 | 646.3 | 646.3 | 323.7 | — | 516.1 | — |
| Glu | y5 | 533.3 | 533.2 | 267.1 | — | 178.4 | — |
| Gly | y4 | 404.2 | 404.2 | 202.6 | — | 135.4 | — |

TABLE E5-continued

Summary of MS Fragmentation and sequence analysis

| | | C-terminal Ion Series | | | | | |
|---|---|---|---|---|---|---|---|
| Sequence Example 2 | Pos. | Expected $y^{1+}$ | Observed m/z | Expected $y^{2+}$ | Observed m/z | Expected $y^{3+}$ | Observed m/z |
| Ser | y3 | 347.2 | 347.2 | 174.1 | — | 116.4 | — |
| Leu | y2 | 260.2 | 260.2 | 130.6 | — | 87.4 | — |
| Gln | y1 | 147.1 | — | — | — | 49.7 | — |
| OH | | — | — | — | — | — | — |

Peptide Mapping:

A peptide map is a fragmentation pattern generated by digestion of a protein with proteolytic enzymes. The pattern of peptide fragments is characteristic of a particular protein and may be used to identify structure. A method for mapping C-peptide was previously developed and four fragments were identified by mass spectrometry. The four fragments contain amino acids 25-31 (labeled as fragment A), 13-24 (labeled as fragment B), 1-12 (labeled as fragment C), and 1-24 (labeled fragment as D) as shown on the bottom panel of FIG. 5.

Figure 5:
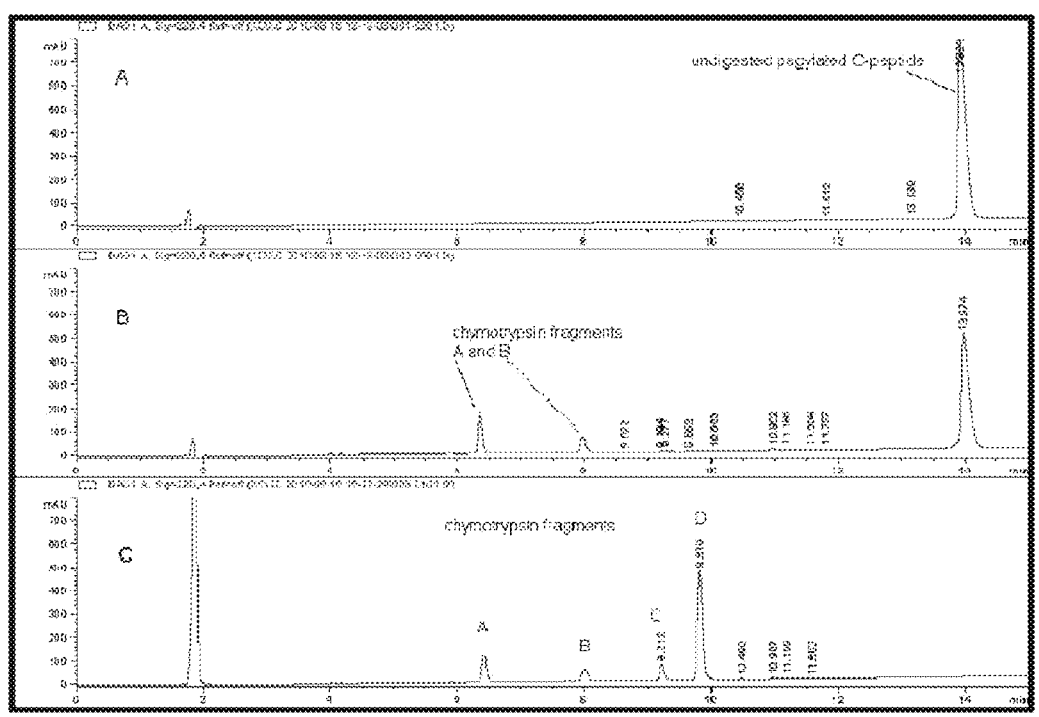
FIG. 5 shows a peptide map for C-peptide (1 mg/mL) and PEGylated C-peptide (10 mg/mL) after incubation with chymotrypsin.

A side-by-side comparison was performed wherein C-peptide (1 mg/mL) and PEGylated C-peptide (10 mg/mL) were dissolved in 25 mM ammonium bicarbonate buffer. To each 1 mL of sample, 40 µL of 0.25 mg/mL chymotrypsin was added and the samples were incubated for four hours at 37° C. The digestion was stopped by the addition of formic acid, and the samples were analyzed by RP-HPLC. The results are shown in FIG. 5.

As expected for PEGylated C-peptide, fragment C (1-12) and D (1-24) were not observed since the PEG moiety is attached at the N-terminus. Fragments 25-31 and 13-24 were observed for the PEGylated C-peptide. To investigate whether the peak at 14 minutes was undigested PEGylated C-peptide, a time course study for the digestion was performed over 27 hours. No additional fragments were obtained consistent with the digestion going to completion. In addition, a 50/50 mixture of undigested PEGylated C-peptide and digested PEGylated C-peptide was analyzed by RP-HPLC with an extended gradient to see if any separation could be achieved; however, only a single peak was observed. Therefore it is concluded that the peak at 14 minutes contains PEGylated 1-12 and 1-24 fragments and possibly some intact PEGylated C-peptide. The inability to resolve these fragments is not unexpected since the chromatographic behavior of the molecule is dominated by the large PEG moiety.

Absence of Counterion:

The ammonium content was measured by Ion Chromatography (IC), acetic acid by HPLC, and sodium content by ICP/MS to assure little or no counter ion remained after the desalting procedure.

The ammonium content was determined to be 0.035% w/w, and the sodium content was found to be 0.02% w/w, below the specification limit.

Although the levels of counterions in the drug substance were low, when calculated on a molar basis, may be indicative of some association of ammonia (0.9 molar ratio) and or sodium (0.4 molar ratio) to the final drug substance.

Sedimentation Velocity by Analytical Ultracentrifugation:

To assess the homogeneity and distribution of any aggregates in PEGylated C-peptide, the sedimentation velocity was measured in an analytical ultracentrifuge. Using this technique, aggregates can be detected on the basis of their different sedimentation coefficients. Sedimentation velocity is an absolute method based on simple physical principles. Its calibration is based on fundamental units of length and time, requiring no standard molecules as reference. Sedimentation coefficients depend on molecular shape as well as molecular mass, thus it is not possible to predict the sedimentation coefficient for an oligomer even when the monomer sedimentation coefficient is known.

Figure 6:
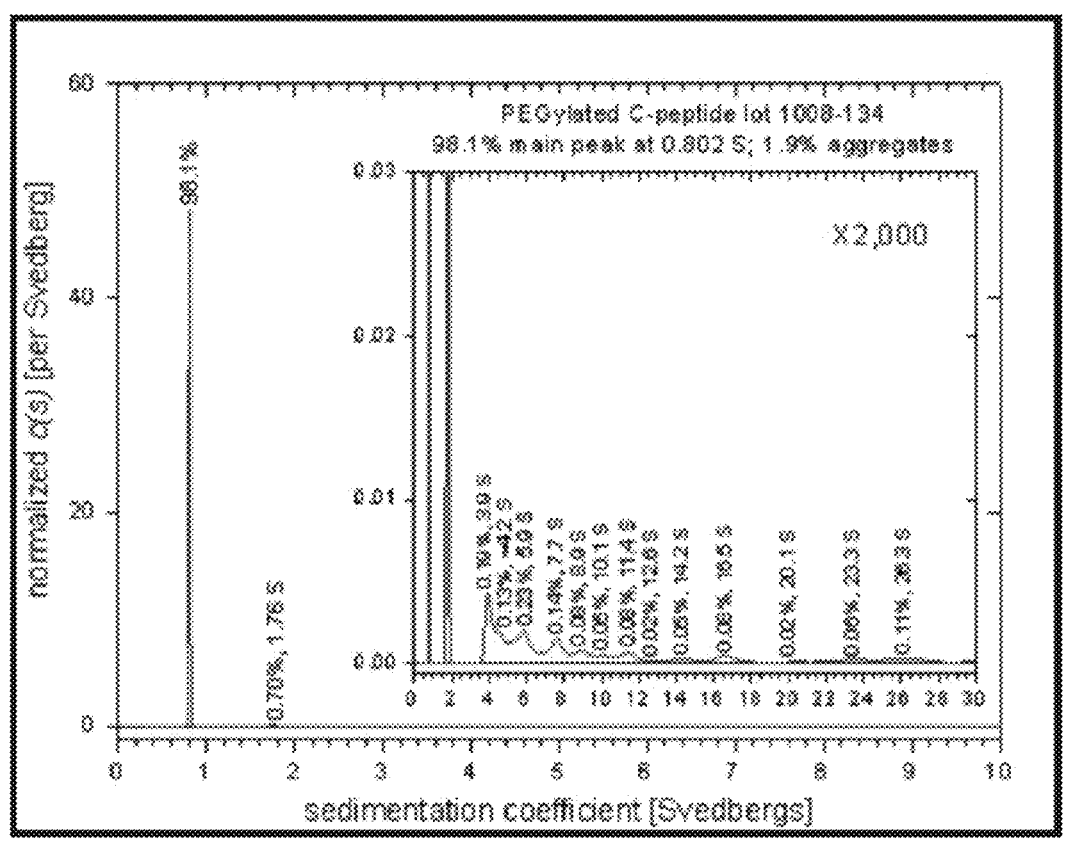
FIG. 6 shows the normalized sedimentation coefficient distribution for PEGylated C-peptide (at ~0.6 mg/mL) in PBS buffer.

The normalized sedimentation coefficient distribution for PEGylated C-peptide lot 1008-134 (at ~0.6 mg/mL) in PBS buffer is shown in FIG. 6. The main peak at 0.802 S is 98.1%, indicating the sample is homogenous. The sedimentation coefficient of C-peptide (unPEGylated) was previously determined to be in the range of ~0.4-0.5 S. No signal in this range was detected, indicating there is no free C-peptide. In addition, the sedimentation coefficient is consistent with a 40 kDa branched PEG (0.82 S).

Circular Dichroism Analysis of C-Peptide and PEGylated C-Peptide:

Near and far UV Circular Dichroism (CD) analysis was performed on C-peptide and PEGylated C-peptide. Samples were dissolved in 20 mM phosphate buffer containing 4.7% sorbitol, pH 6.0 at 1 mg/mL for C-peptide and ~10.4 mg/mL for PEGylated C-peptide (equivalent to 0.69 mg/mL of C-peptide). The solvent subtracted spectrum was converted to the mean residue ellipticity using the peptide concentration (1 or 0.69 mg/mL), the mean residue weight (97.4), and the path-length of the cell (1 cm for the absorbance measurement or 0.02 cm for the CD). Measurements were carried out on a Jasco J-715 spectropolarimeter.

Figure 7:
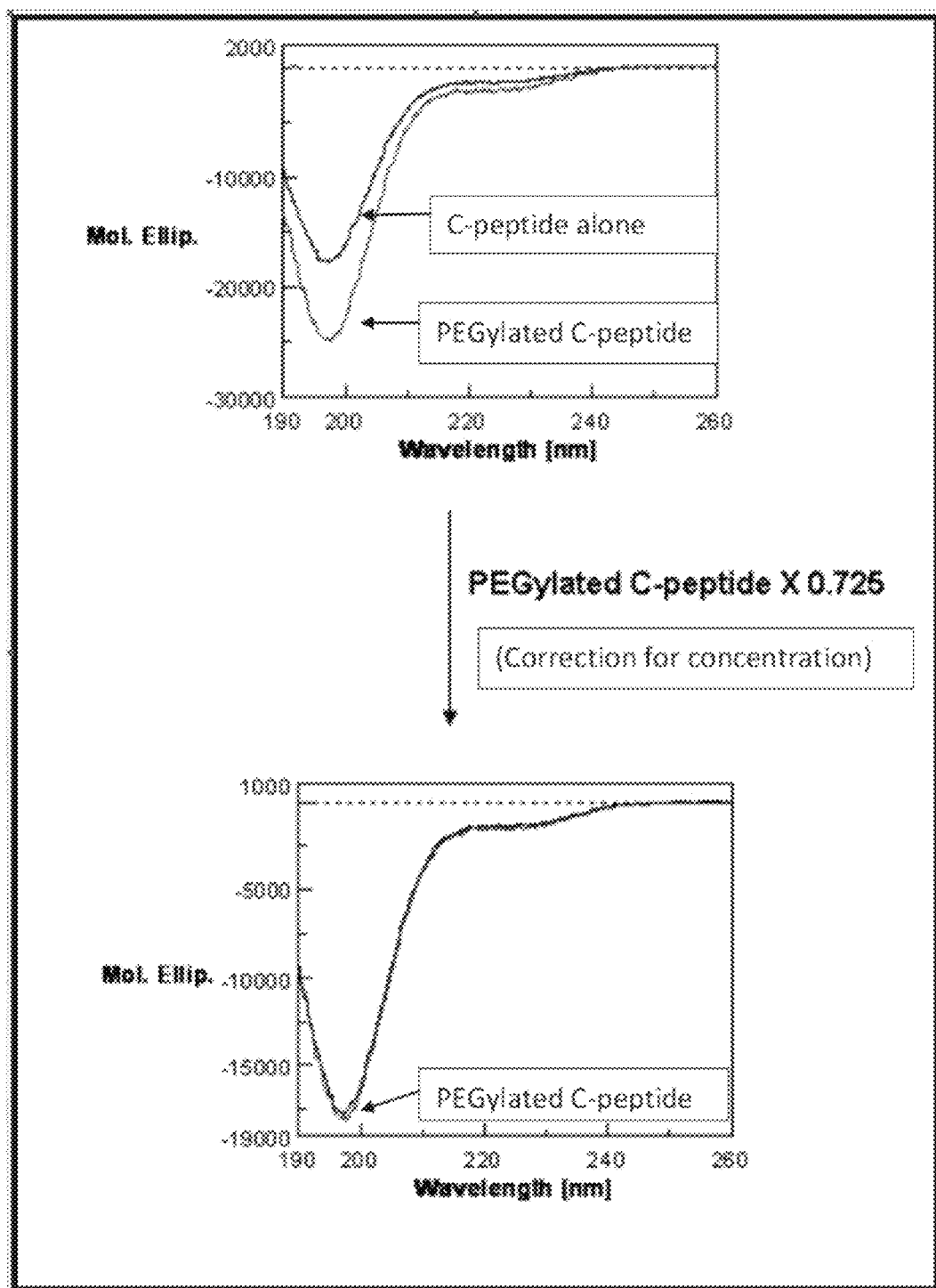
FIG. 7 shows a Circular Dichroism Analysis of C-peptide and PEGylated C-peptide.

As shown in FIG. 7, the mean residue ellipticity of C-peptide (upper line and PEGylated C-peptide (lower line) in the near UV region is essentially zero for both samples as there are no aromatic groups and disulfide bonds (shown in the upper panel of FIG. 7).

The far UV CD spectra of C-peptide and PEGylated C-peptide show the secondary structure is largely disordered. There is no double minima at 220 and 208 nm typical for a α-helix and no valley at 217 nm typical for anti-parallel β-sheet.

CD analysis shows a nearly identical spectral shape for C-peptide and PEGylated C-peptide when corrected for concentration (lower panel of FIG. 7) (note there is some error in the concentration estimates as the sample weights were not corrected for water or salts/solvents). Therefore, it can be concluded that PEGylation does not alter the secondary structure of the peptide.

Figure 8:
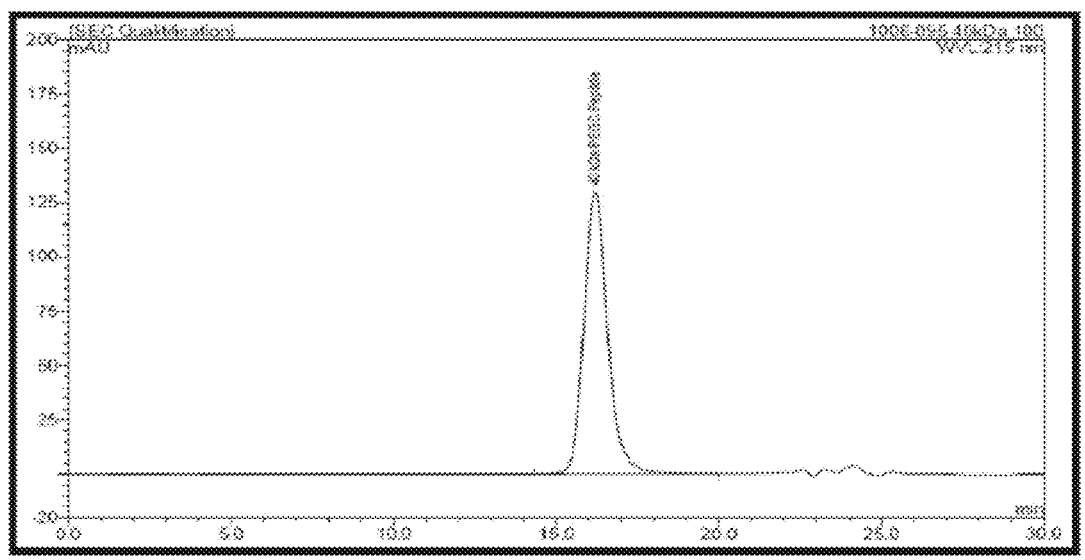
FIG. 8 shows the results of Size Exclusion Chromatography (SEC) of a sample of PEGylated C-peptide.

Size Exclusion Chromatography (SEC):

A sample of the PEGylated C-peptide of Example 1 (100 µg in 20 mM phosphate buffer, 4.7% sorbitol, pH 6.0) was analyzed by size exclusion chromatography as shown in FIG. 8.

Figure 9:
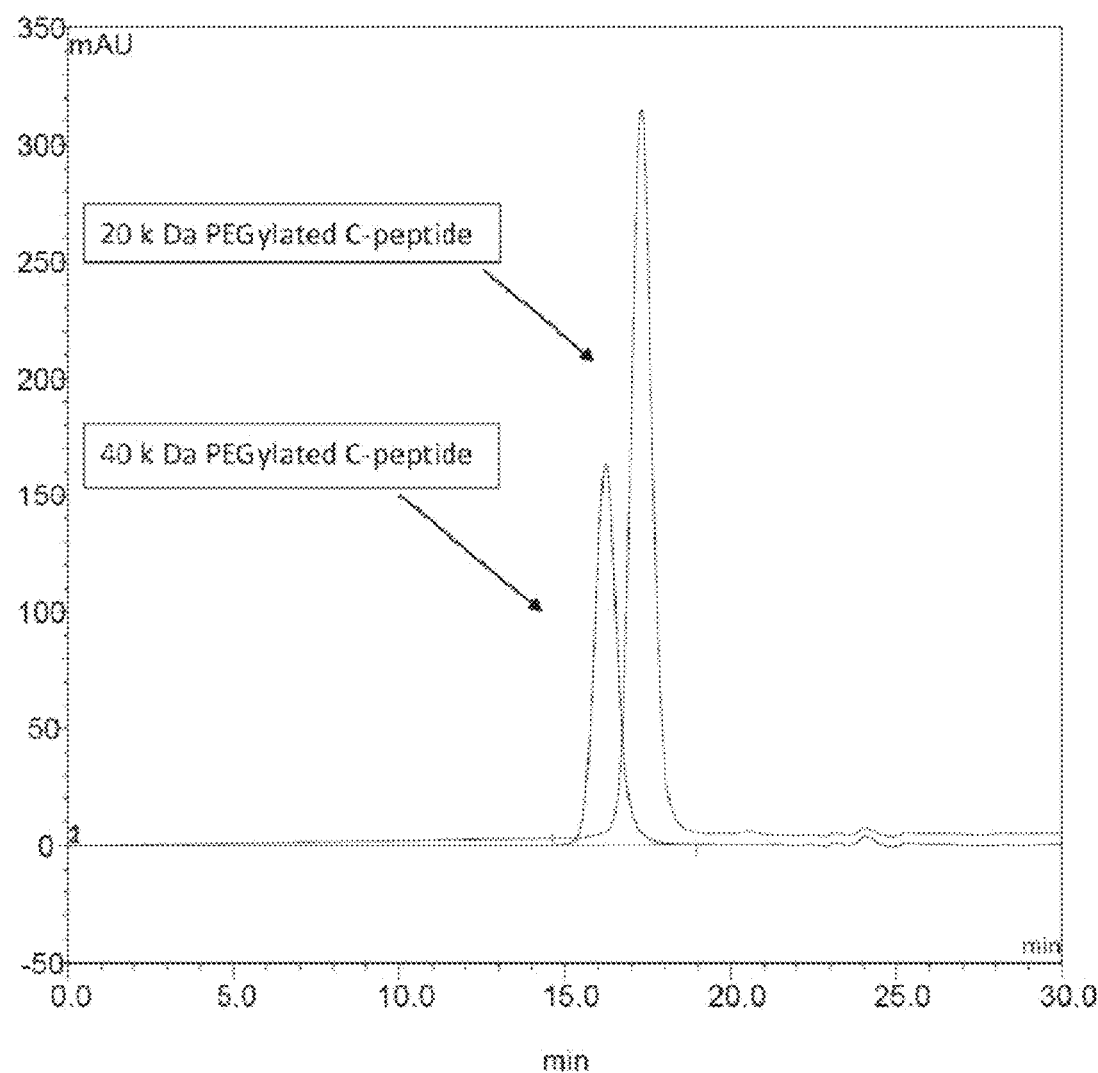
FIG. 9 shows an overlay of the chromatogram of 20 kDa PEGylated C-peptide and 40 kDa PEGylated C-peptide.

As part of the SEC method qualification, a 20 kDa PEGylated peptide was independently synthesized and analyzed by SEC to show the method was capable of distinguishing related compounds based on size. An overlay of the chromatogram of the kDa PEGylated C-peptide (both samples at 100 μg load, in the same buffer system) with the PEGylated C-peptide is shown in FIG. 9. As can be seen in FIG. 9, peaks of lower molecular weight elute later from the SEC column. The absence of peaks before the main peak indicates there are no appreciable levels of higher molecular weight species present in the PEGylated C-peptide. Similarly, the absence of peaks after the main peak indicates there are not appreciable levels of lower molecular weight species.

Figure 10:
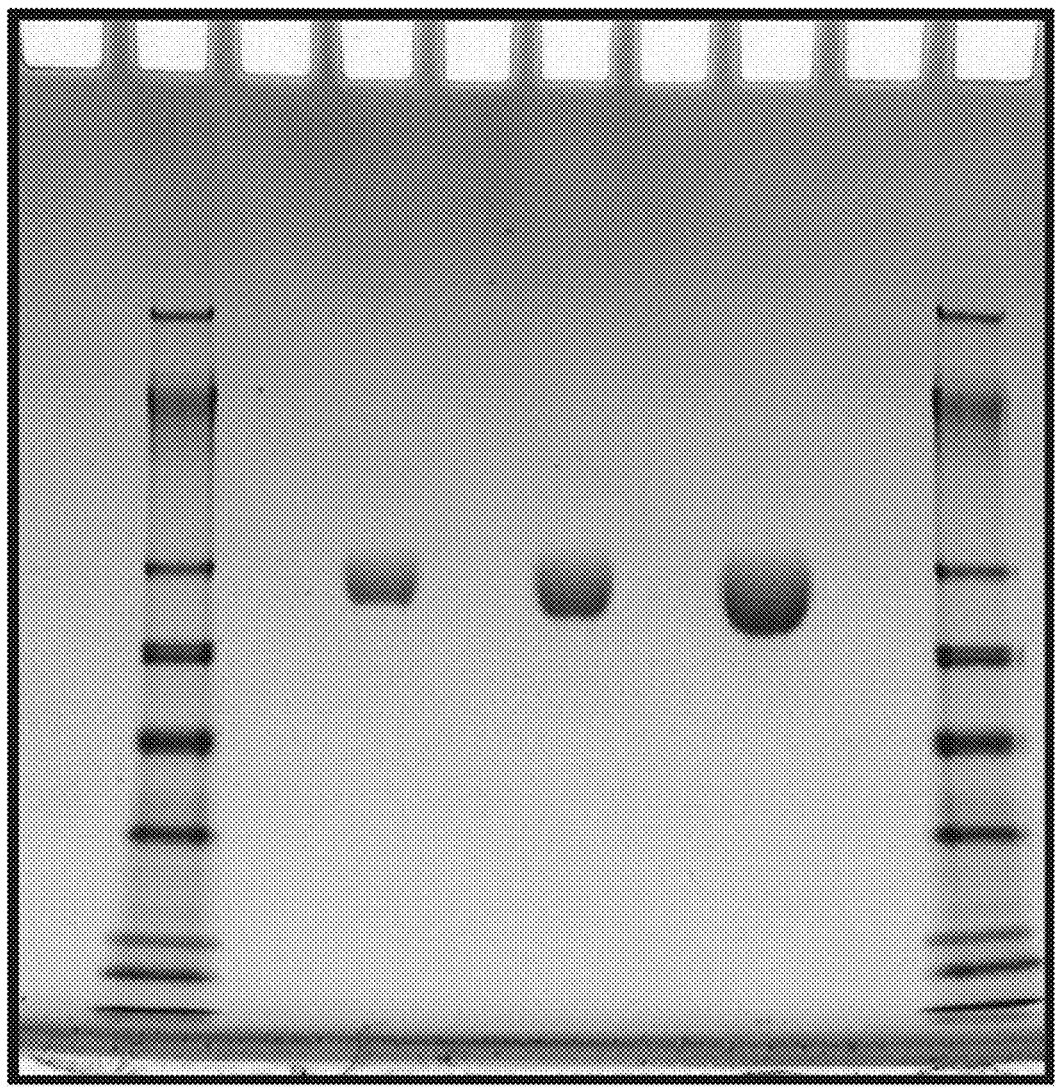
FIG. 10 shows the results of sodium dodecyl sulfate polyacrylamide gel electrophoresis SDS-PAGE: Gel electrophoresis of the PEGylated C-peptide with sample load ranging from 2-10 mcg.

SDS-PAGE:

Gel electrophoresis was conducted using a 4-12% Tris-Glycine gel. Molecular weight standards (see Blue Plus2, Prestained Standards from Invitrogen) were applied in Lanes 2 and 10 as displayed in FIG. 10. Different amounts of PEGylated C-peptide ranging from 2 μg to 10 μg were applied to the gel in Lanes 4, 6, and 8. A single intense band between 64-98 kDa was visualized by Coomassie staining. The hydrodynamic radius of PEG is known to be greater than the size predicted based on the molecular weight of the protein markers. Therefore, this result is not unexpected. The SDS-PAGE results also show the absence of other higher molecular weight impurities.

Activity Profiling:

Samples of PEGylated C-peptide, were compared to authentic unlabeled C-peptide to confirm that the PEGylated product retained the activity of the unlabelled peptide.

Methods:

Human kidney (HK2) cells were seeded at a density of 20,000 cells/well in (non-coated) 96 well (bl/cl) plates and incubated for 48 hours. On the day of the experiment, HK2 cells were washed and starved in Dubelco's Modified Eagles Medium+0.5% bovine serum albumin for 1 hour. Cells were treated with 1 nM (final concentration) with ten replicates for 5 minutes. C-Peptide PEG GMP (lot #1-FIN-0988), C-Peptide PEG Tox (lot #1007-119), C-Peptide PEG Tox (lot #1008-090), unmodified C-Peptide (lot #209400-3) and C-Peptide PEG reference (lot #1008-134) were added in equal volumes. Plates were spun at 1000 rpm for 5 minutes. The total treatment time was 7-10 minutes. Immediately after treatment, cells were fixed with 2% (final) paraformaldehyde and permeabilized with ice-cold methanol. Cells were then treated with anti-pERK antibody and the plates were processed using the IF+Tyramide amplification, following standard protocols.

Figure 11:
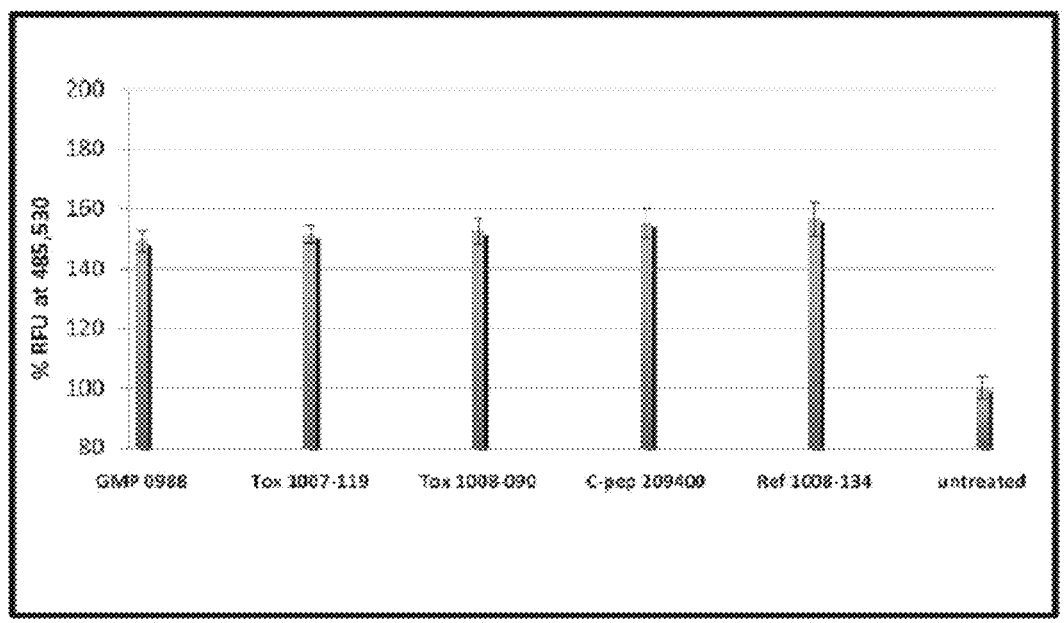
FIG. 11 shows the results of an assessment of the biological activity of the PEGylated C-peptide compared to native C-peptide in the ERK phosphorylation assay, wherein Lots 1007-119, 1008-134, 1008-080, and 1-FIN-0988 represent different samples of CBX129801 and lot 209400 is a sample of native C-peptide.

Results:

The results shown in FIG. 11, demonstrate that the PEGylated C-peptide retains the activity of the un-PEGylated product, and this activity is consistent across several different lots of C-peptide.

Example 3

Pharmaceutical Composition

The drug product is a sterile aqueous solution of CBX129801 (20 mg/mL) in 10 mM sodium phosphate buffer with 4.7% sorbitol at pH 6.0.

The composition of the formulation and the function of each component are shown in Table E6.

TABLE E6

Composition of CBX129801 drug product

| Component | Reference to Quality Standard | Function | Amount per mL |
|---|---|---|---|
| CBX129801 | In-house standard | Drug substance | 20.0 mg |
| Sodium phosphate, monobasic dihydrate | USP | Buffering agent | 1.49 mg |
| Sodium phosphate dibasic, anhydrous | USP | Buffering agent | 0.056 mg |
| Sorbitol | NF | Tonicity and stabilizing agent | 47.0 mg |
| Sodium hydroxide | NF | pH adjustment | q.s. to pH 6.0 |
| Hydrochloric acid | NF | pH adjustment | q.s. to pH 6.0 |
| Water for Injection | USP | Diluent | q.s. to 1.0 mL |

To achieve the desired doses, the drug product may be diluted at the clinical site prior to administration with commercially available Sterile Normal Saline (0.9%).

Description of the Manufacturing Process

Formulation of Bulk Solution

A 10 mM phosphate buffer solution is prepared in a mixing vessel by dissolving sodium phosphate (mono and dibasic) and in ~80% of the total volume of Water for Injection (WFI) required. Sorbitol is added to the buffer solution with mixing until dissolved. The pH is adjusted to 6.0 with 1 M NaOH or HCl. The buffer is brought to final volume with WFI. The CBX129801 drug substance is added to a separate vessel containing the phosphate/sorbitol buffer at approximately 80% of the final batch size (by volume). The drug substance is dissolved with mixing. After the drug substance has dissolved, the pH is adjusted to 6.0 with 1 M NaOH or HCl. Sufficient quantities of the phosphate/sorbitol buffer are then added to bring the batch to final volume. Then a bioburden reduction filtration is performed. Immediately prior to the sterile filtration, samples are taken for bioburden testing (pre-filtration bioburden).

Sterile Filtration

The bulk solution is sterile filtered (two 0.22 μm PVDF hydrophilic filters in series) into a sterile receiving vessel. Each filter is integrity tested before and after use.

Filling

Filling is performed using an automated filler. CBX129801 drug product is aseptically filled into vials closed with a rubber stopper, and then sealed with an aluminum overseal with plastic cap.

Inspection/Labeling

The vials are transferred to the visual inspection area and undergo 100% visual inspection at controlled room temperature. After inspection, the vials are labeled and placed into cartons to protect from light and stored at 2-8° C.

Stability

The clinical batch of CBX129801 drug product was placed on stability at the recommended storage condition of 5° C. Studies were conducted in 5 mL glass vials (with a nominal 4 mL fill volume) with Teflon-faced stoppers and overseals. The 18-month results are shown in Table E7.

TABLE E7

Stability Data for CBX129081 Drug Product Lot 1-FIN-0988
in 10 mM sodium phosphate, 4.7% sorbitol, pH 6.0 at 5° C.

| Time | Appearance | pH | Content (% LC) | Purity[1] (Area-%) | Impurities | Endo-toxin (EU/mL) | Particulate Matter |
|---|---|---|---|---|---|---|---|
| Initial | Clear colorless solution essentially free from visible particulate | 6.0 | 96.5 | 98.59 | RRT 0.99: 1.41% | 0.05 | ≥10 μm = 205 ≥25 μm = 6 |
| 3 month | Clear colorless solution essentially free from visible particulate | 6.1 | 100.2 | 97.81 | RRT 0.99: 2.19% | | |
| 6 month | Clear colorless solution essentially free from visible particulate | 6.1 | 101.2 | 97.44 | RRT 0.63: 0.15% RRT 0.71: 0.14% RRT 0.99: 2.26% | | |
| 12 month | Clear colorless solution essentially free from visible particulate | 6.2 | 94.0 | 97.75 | RRT 0.70: 0.13% RRT 0.72: 0.10% RRT 0.99: 2.01% | | |
| 18 month | Clear colorless solution essentially free from visible particulate | 6.1 | 98.7 | 96.51 | RRT 0.71: 0.12% RRT 0.72: 0.15% RRT 0.99: 3.23% | | |

LC = Label Claim
N/R = Not required under study protocol.

Example 4

Phase 1 Pharmacokinetic Study

A Phase 1, randomized, blinded, placebo-controlled, multiple ascending dose escalation study of CBX129801 administered via subcutaneous injection was performed. One objective of this study was to assess the single and multiple dose pharmacokinetics (PK) of plasma CBX129801 after subcutaneous (SC) administration of CBX129801.

Treatment Groups:

Subjects 18-55 years of age with type 1 diabetes mellitus for a minimum of 5 years and a stable, optimized diabetic regimen for at least 3 months in otherwise good health were enrolled. Subjects had no detectable C-peptide levels (fasting C-peptide concentration <0.3 ng/mL (<0.1 nmol/L)). Body mass index (BMI) was ≥18.0 and <35.0 kg/m². Subjects were required to have recordable sensory nerve conduction responses in both sural nerves on 2 occasions during screening. Exclusionary lab values included abnormal liver function tests (serum aspartate aminotransferase [AST] or alanine aminotransferase [ALT]>1.5×upper limit normal [ULN]), macroalbuminuria defined as urine protein ≥2+ by dipstick, triglycerides ≥600 mg/dL, thyroid-stimulating hormone (TSH) >1.3×ULN, or serum creatinine >1.5 mg/dL (>128 μmol/L). Subjects who had experienced a severe hypoglycemic event (defined as requiring the assistance of another individual) within 6 months of the study or recurrent episodes of non-severe hypoglycemia (≥3 per week on average) that were deemed clinically significant by the investigator were excluded. Treatment with medication for diabetic peripheral neuropathy within 30 days of dosing including but not limited to Neurontin (gabapentin), Lyrica (pregabalin), various anti-seizure medications (e.g., Cymbalta (duloxetine), amitriptyline, Dilatin (phenyloin), Tegretol (carbamazepine)), analgesic creams and gels (made from lidocaine or capsaicin), and narcotics were excluded. Four sequential dose cohorts (n=10 subjects per cohort, 8 on active drug and 2 on placebo for Cohorts A-C; 29 on active drug and 13 on placebo for Cohort D) were administered CBX129801 as follows: Cohort A: 0.3 mg CBX129801 or placebo; Cohort B: 1.0 mg CBX129801 or placebo; Cohort C, 3.3 mg CBX129801 or placebo; and Cohort D: 0.8 mg CBX129801 following a loading dose on day 1 of 2.0 mg CBX129801.

For the subjects enrolled in Cohort A (0.3 mg) and Cohort B (1.0 mg), a single subcutaneous dose was administered; three weeks later, four weekly subcutaneous doses were administered, for a total of five doses. For the subjects enrolled in Cohort C (3.3 mg), a single subcutaneous dose was administered; three weeks later, three weekly subcutaneous doses were administered, for a total of four doses. For the subjects enrolled in Cohort D (0.8 mg, 2.0 mg loading dose), a single subcutaneous dose was administered; one week later, eleven weekly subcutaneous doses were administered, for a total of twelve doses.

Pharmacokinetic samples were collected pre-dose and post-dose at 24, 48, 72, 120, 168, 240, 336, 408 (first dose only), and 504 hours after the first and last doses in Part 1, Cohorts A, B, and C (and additionally at 672 hours for the Cohort C), and before each other dose; the 504 hour post-dose sample after the first dose is the pre-dose sample before Dose 2. In addition, pharmacokinetics samples were collected at 2 and 6 hours post-dose after Dose 1 in all cohorts A, B, and C. In Cohort D, predose samples were collected to determine pharmacokinetics were collected on Days 0, 7, 14, 28, 42, 56, 70, and 84. In addition a sample was collected on Day 105.

Methods:

Plasma concentrations were determined by ELISA using Mercodia's commercial kit for C-peptide. CBX129801 standards ranging from 13.6 to 0.21 nM and quality control (QC) samples (high, medium and low QCs) were prepared in rat plasma and substituted in place of the C-peptide standards and QCs. Plasma sample concentrations below the quantifiable limit (BQL) value were set to zero for the non-compartment pharmacokinetic analysis and were removed for the compartmental pharmacokinetic analysis.

Standard non-compartment pharmacokinetic parameters as shown in Table E8 were calculated from the plasma concentration-time profiles using WinNonlin version 5.3 (Pharsight, a Certara™ company, St. Louis, Mo.). Nominal times from the most recent dose were used for calculation of pharmacokinetic parameters.

TABLE E8

Non-Compartment Pharmacokinetic Parameters

| Parameter | Definition | Method of Determination |
|---|---|---|
| $C_{max}$ | Maximum observed concentration | Observed directly from data |
| $T_{max}$ | Time for $C_{max}$ | Observed directly from data as time of first occurrence with the dosing interval |
| $AUC_\tau$ | Area under the concentration-time profile from time zero to time tau ($\tau$), the dosing interval, where tau was 7 days. | Linear trapezoidal method |
| $t_{1/2}$ | Terminal half-life | $Log_e(2)/k_{el}$, where $k_{el}$ is the rate constant during the terminal phase calculated by a linear regression of the log-linear concentration-time curve. |
| $T_{lag}$ | Lag time | Observed directly from data |
| $CL/F^a$ | Apparent clearance | $Dose/AUC_\tau$ |
| $Vz/F^a$ | Apparent volume of distribution | $Dose/(AUC_\tau \cdot k_{el})$ |
| DFL | Degree of fluctuation | $(Cmax - Cmin)/Cavg \cdot 100$ |
| $DN\,C_{max}$ | Dose normalized $C_{max}$ | $C_{max}/Dose$ |
| $DN\,AUC_\tau$ | Dose normalized $AUC_\tau$ | $AUC_\tau/Dose$ |

Non-compartment pharmacokinetic parameter values calculated using WinNonlin version 5.3.

A compartmental population pharmacokinetic model was built using a non-linear mixed-effects modeling approach. The first-order conditional maximum likelihood estimation method in the NONMEM program (Version 7.2, ICON Development Solutions, Elliott City, Md.) and NM-TRAN pre-processor were used. Models were run using the gfortran Fortran Compiler (GNU Project) on a personal computer (Lenovo T410) under the Microsoft Windows 7 operating system. R (Version 2.11.1, R Foundation for Statistical Computing) was used to manage NONMEM and create graphical output. The subroutines within NONMEM were linear mammillary models (ADVAN1 used with TRANS2 in the PREDPP library) to fit a one-compartment model with zero order input. Analyses were carried out using an additive residual error model on log-transformed data. Model selection was guided by the decrease in the objective function value, the condition number, graphical goodness of fit analysis, and the plausibility of parameter estimates.

The plasma concentration time profiles were simulated using 500 parameters estimated from the compartmental pharmacokinetic parameter estimates and the covariance matrix. Graphical output figures were created in R.

Results:

TABLE E9

Arithmetic (% CV) and geometric mean non-compartmental pharmacokinetics parameters of CBX129801 following single dose CBX129801 administered subcutaneously

| | Dose | | |
|---|---|---|---|
| Parameters | 0.3 mg Mean (% CV) | 1.0 mg Mean (% CV) | 3.3 mg Mean (% CV) |
| $C_{max}$, nM | 0.269 (7.24) | 0.975 (23.4) | 4.13 (43.3) |
| $T_{max}$, day | 4.32 (51.0) | 4.81 (32.2) | 4.24 (23.9) |
| $AUC_{last}$ nM · day | 1.38 (51.9) | 11.8 (32.1) | 49.7 (41.4) |
| $AUC_\infty$, nM · day | NC | 14.5 (29.6) | 60.4 (45.0) |
| % $AUC_{extrap}$ | NC | 19.0 (26.7) | 16.2 (55.6) |
| Half-life (days) | NC | 6.37 (16.4) | 6.92 (40.9) |
| Vz/F (L) | NC | 14.3 (26.9) | 12.7 (45.0) |
| CL/F (L/Day) | NC | 1.59 (33.3) | 1.38 (42) |

NC—Not calculated

TABLE E10

Arithmetic (% CV) and geometric mean non-compartmental pharmacokinetic parameters of CBX129801 following multiple doses of CBX129801 administered subcutaneously

| | Dose | | |
|---|---|---|---|
| Parameters | 0.3 mg every 7 days for 4 doses Mean (% CV) | 1.0 mg every 7 days for 4 doses Mean (% CV) | 3.3 mg every 7 days for 3 doses Mean (% CV) |
| $C_{max}$, nM | 0.718 (29.2) | 2.30 (11.0) | 11.2 (29.5) |
| $T_{max}$, day | 3.28 (63.2) | 1.82 (52.1) | 2.94 (44.1) |
| $AUC_{last}$ nM · day | 8.14 (37.1) | 26.9 (21.8) | 154 (36.1) |
| $AUC_\tau$, nM · day | 4.31 (28.1) | 14.2 (13.4) | 66.7 (27.5) |
| $C_{min}$, nM | 0.469 (26.6) | 1.73 (19.8) | 6.82 (32.1) |
| $C_{ave}$, nM | 0.615 (28.1) | 2.04 (13.4) | 9.52 (27.5) |
| Half-life (days) | 7.92 (41.2) | 6.35 (16.0) | 6.33 (27.8) |
| $Vz_{ss}/F$ (L) | 21.8 (84.1) | 13.7 (12.5) | 10.4 (44.8) |
| $CL_{SS}/F$ (L/Day) | 1.62 (34.1) | 1.52 (12.7) | 1.13 (26.4) |
| $AUC_{T, md}/AUC_{\infty, sd}$ | NC | 1.04 (23.6) | 1.22 (34.6) |
| $RC_{max}$ | 3.29 (12.5) | 2.44 (19.4) | 3.01 (39.2) |
| $RAUC_T$ | 3.70 (NC) | 2.90 (30.2) | 3.41 (45.2) |
| $DNC_{min}$, nM/mg | 1.56 (26.6) | 1.73 (19.8) | 2.07 (32.1) |
| $DNAUC_\tau$, nM · day/mg | 14.4 (28.1) | 14.2 (13.4) | 20.2 (27.5) |
| $DNC_{max}$, nM/mg | 2.39 (29.2) | 2.30 (11.0) | 3.39 (29.5) |

NC—Not calculated
$RAUC_T$ accumulation index for AUC calculated from $AUC_T$
$RC_{max}$ accumulation index for $C_{max}$ calculated from $C_{max}$
pharmacokinetic parameters calculated from the last dose

TABLE E11

Arithmetic (% CV) and mean predose plasma CBX129801 concentrations in an escalating subcutaneous dose study (Cohort D, 2.0 mg loading dose followed by eleven weekly 0.8 mg doses of CBX129801)

| Day | Mean | % CV |
|---|---|---|
| 0 | 0.00 | NC |
| 7 | 2.70 | 50.0 |
| 14 | 2.38 | 43.6 |
| 28 | 2.04 | 43.1 |
| 42 | 1.97 | 37.6 |
| 56 | 1.90 | 40.5 |

TABLE E11-continued

Arithmetic (% CV) and mean predose plasma CBX129801 concentrations in an escalating subcutaneous dose study (Cohort D, 2.0 mg loading dose followed by eleven weekly 0.8 mg doses of CBX129801)

| Day | Mean | % CV |
|---|---|---|
| 70 | 1.73 | 37.1 |
| 84 | 1.82 | 32.3 |
| EOS | NC | NC |

EOS—End of Study

TABLE E12

Statistics for the assessment of dose proportionality of CBX129801 in patients in an escalating subcutaneous dose study

| Parameter | Slope | | |
|---|---|---|---|
| | Mean (SE) | 90% CI | P-value (slope = 1) |
| Single Dose | | | |
| $C_{max}$ | 1.116 (0.08775) | 0.9631 to 1.268 | 0.2045 |
| $AUC_\infty$ | 1.154 (0.1607) | 0.8709 to 1.437 | 0.3544 |
| Multiple Dose | | | |
| $C_{max}$ | 1.150 (0.05749) | 1.051 to 1.248 | 0.0167 |
| $AUC_T$ | 1.148 (0.05481) | 1.054 to 1.243 | 0.0133 |

Figure 12:
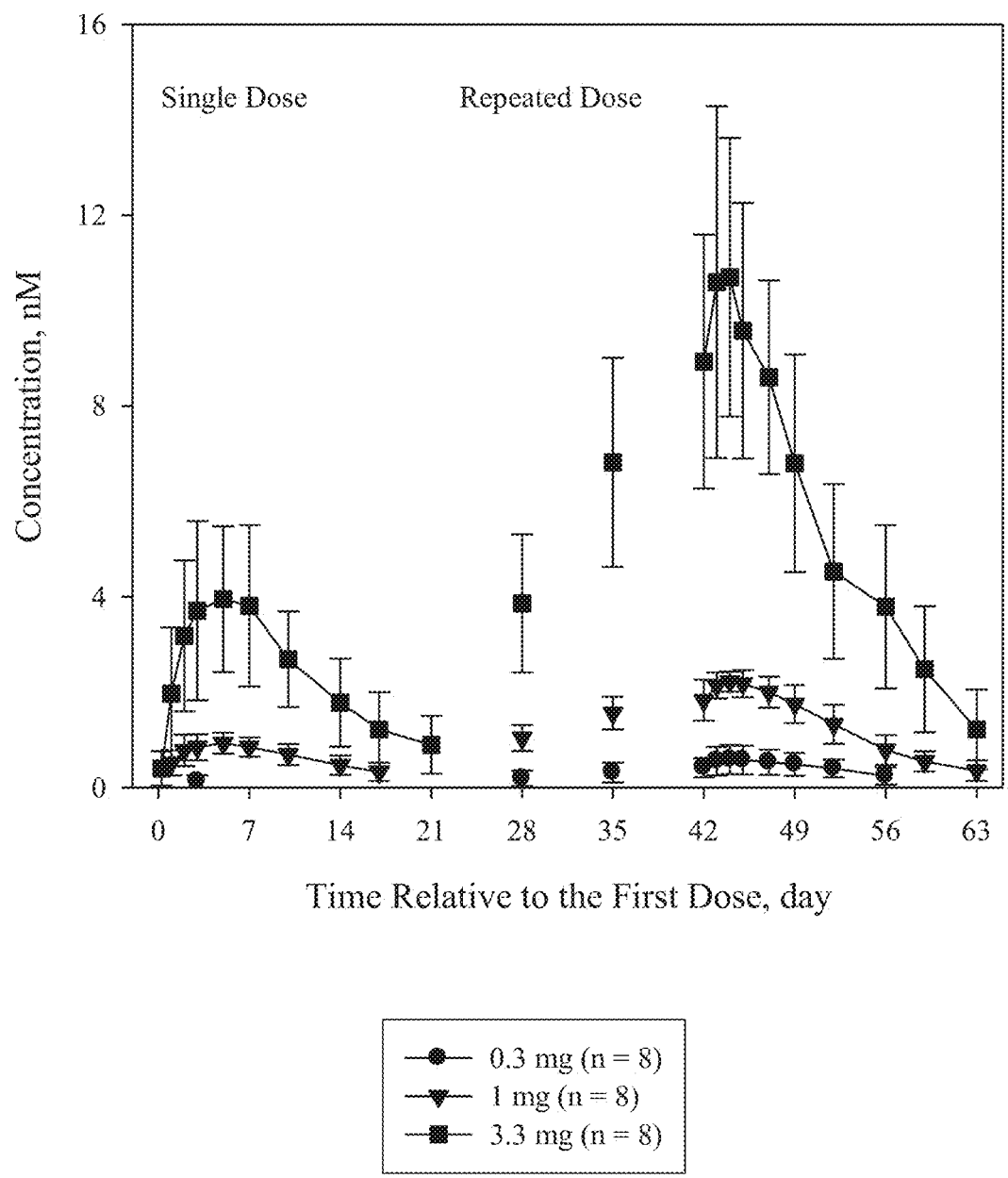
FIG. 12 shows mean plasma CBX129801 concentration time profiles in linear scale following subcutaneous administration of CBX129801 in a human escalating dose study.
Figure 13:
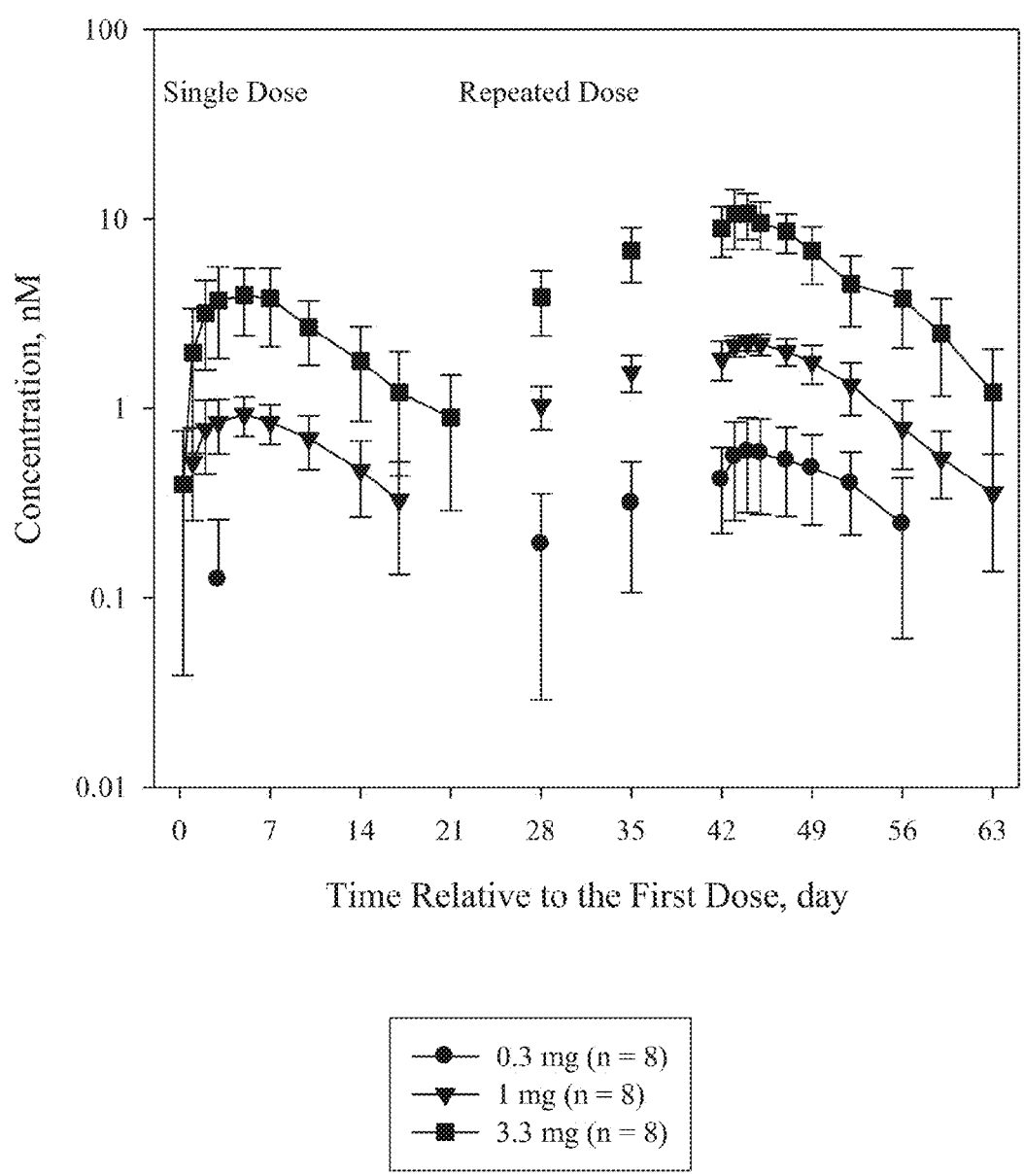
FIG. 13 shows mean plasma CBX129801 concentration time profiles in logarithmic scale following subcutaneous administration of CBX129801 in a human escalating dose study.

Median peak plasma CBX129801 concentrations ($C_{max}$) were observed 3 to 7 days following single and multiple dose administration over the dose range of 0.3 to 3.3 mg, suggesting that the dose amount and multiple doses do not change the duration of absorption from the subcutaneous injection into circulating plasma. FIG. 12 shows the mean plasma concentration time profiles in linear scale following subcutaneous administration of CBX129801 in an escalating dose study. FIG. 13 shows the mean plasma concentration time profiles in logarithmic scale following subcutaneous administration of CBX129801 in an escalating dose study.

Table E9 shows the non-compartmental pharmacokinetic parameters for CBX129801 following a single CBX129801 dose administered subcutaneously. Table E10 shows the non-compartmental pharmacokinetic parameters for CBX129801 following multiple CBX129801 doses administered subcutaneously. Table E12 shows predose plasma CBX129801 concentrations in an escalating subcutaneous dose study (Cohort D). Table E12 shows dose-proporsionality parameters for single and multiple dosing.

Figure 14:
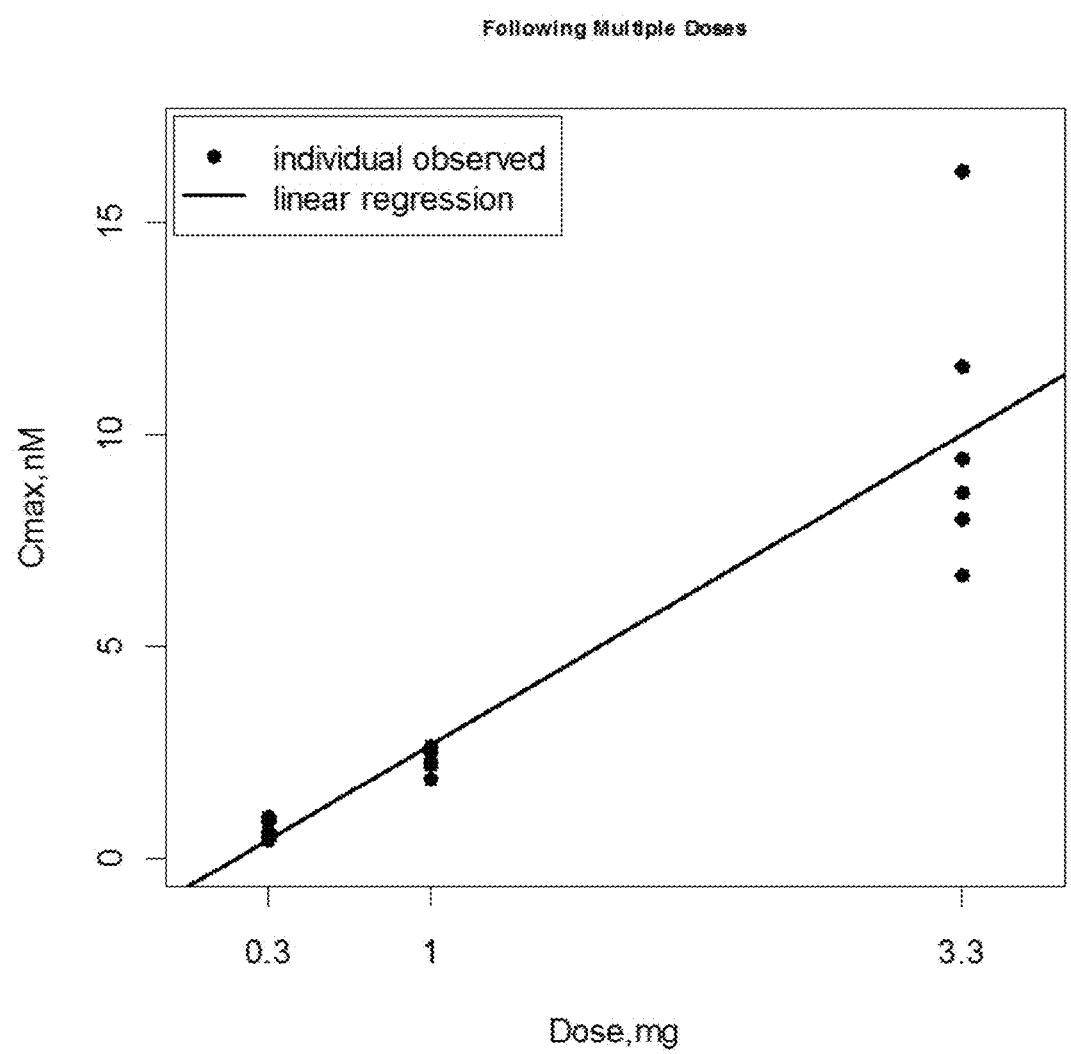
FIG. 14 shows plasma CBX129801 $C_{max}$ following subcutaneous administration of multiple CBX129801 doses.
Figure 15:
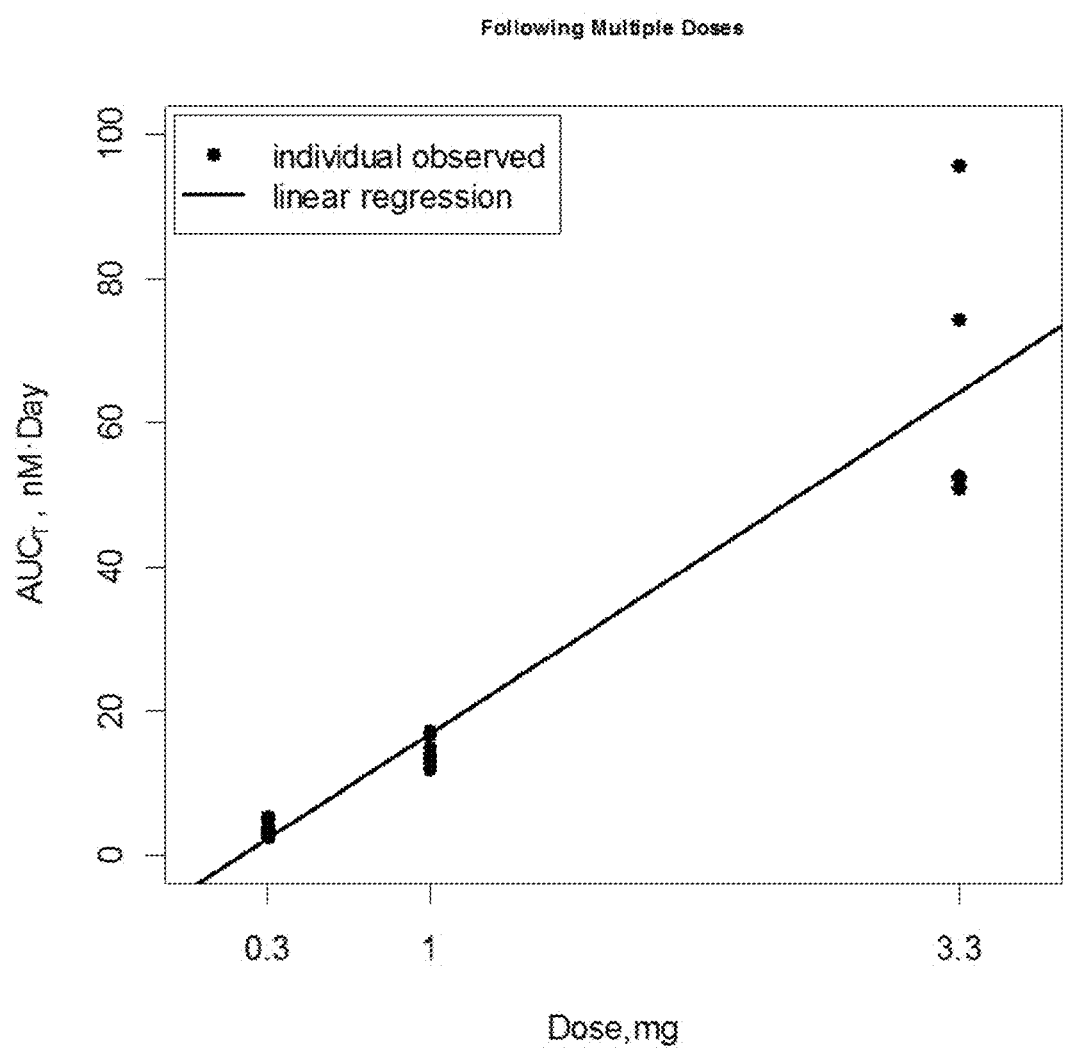
FIG. 15 shows individual plasma CBX129801 $AUC_T$ following subcutaneous administration of multiple CBX129801 doses.
Figure 16:
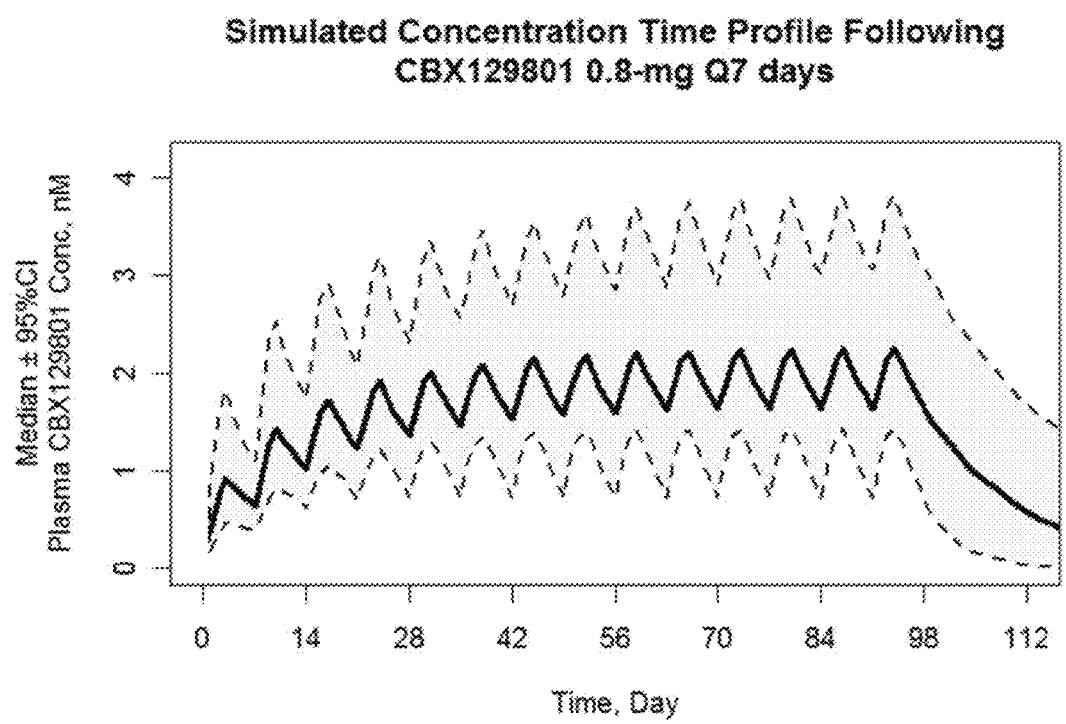
FIG. 16 shows a simulated time course of plasma CBX129801 concentrations following subcutaneous administration of 0.8 mg CBX129801 every 7 days.
Figure 17:
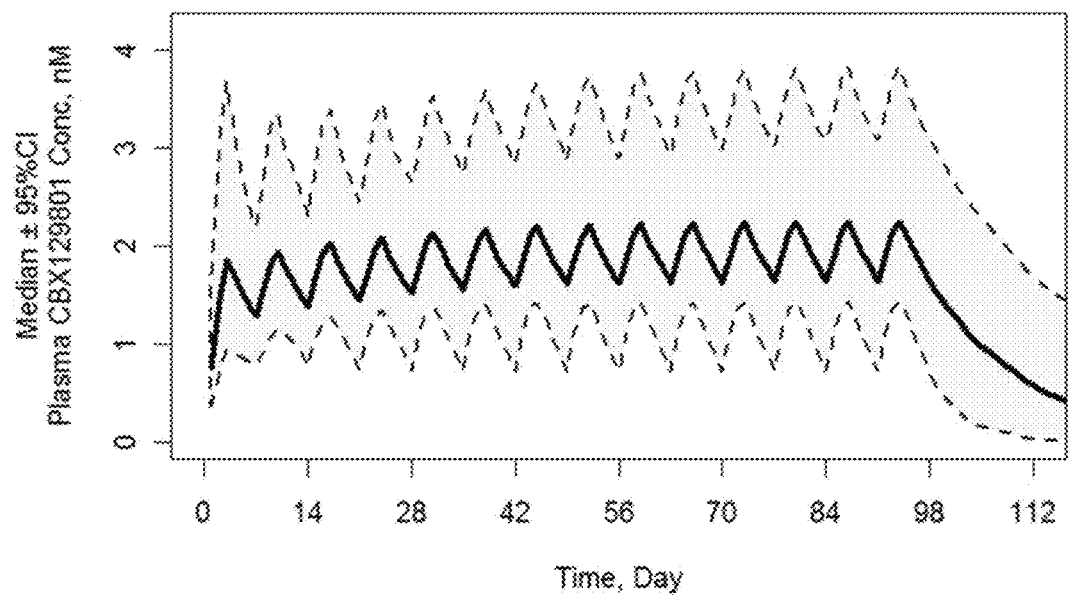
FIG. 17 shows a simulated time course of plasma CBX129801 concentrations following subcutaneous administration of a loading dose of 1.6 mg CBX129801 followed by a maintenance dose of 0.8 mg CBX129801 every 7 days.
Figure 18:
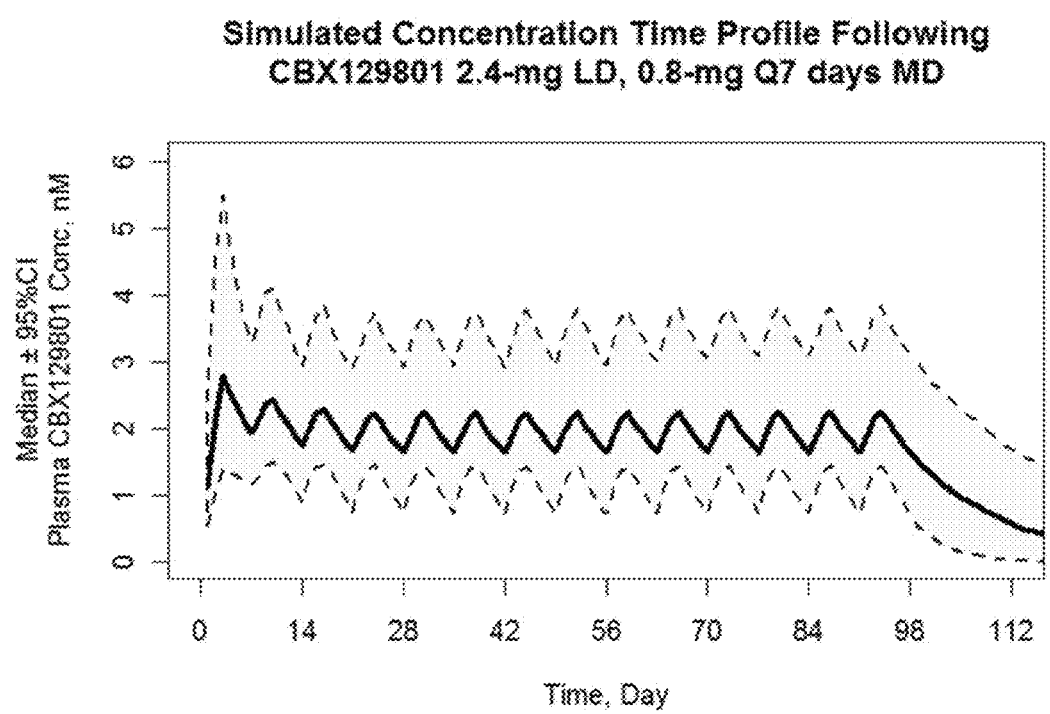
FIG. 18 shows a simulated time course of plasma CBX129801 concentrations following subcutaneous administration of a loading dose of 2.4 mg CBX129801 followed by a maintenance dose of 0.8 mg CBX129801 every 7 days.
Figure 19:
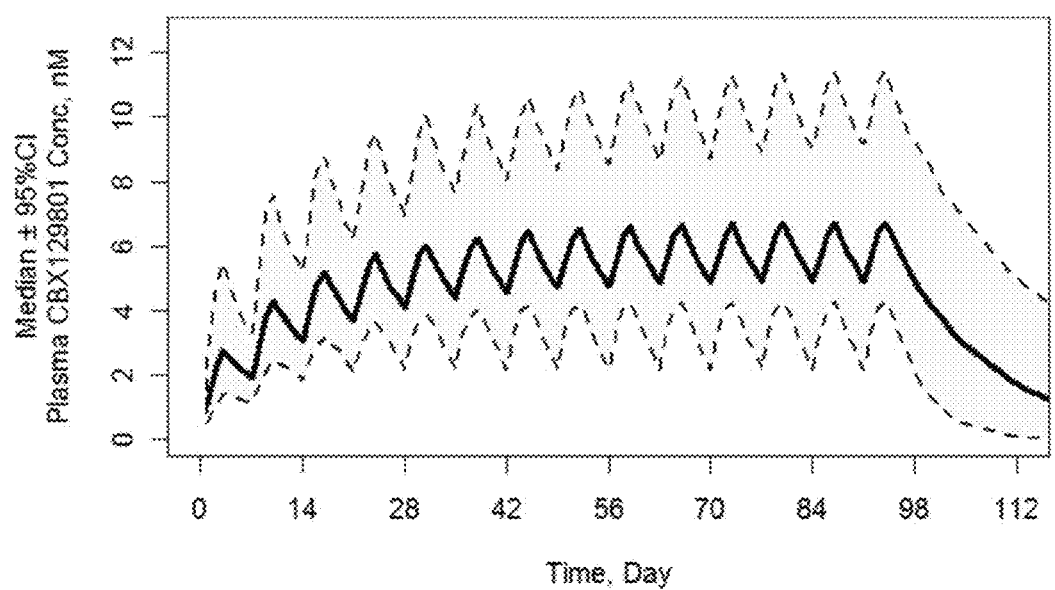
FIG. 19 shows a simulated time course of plasma CBX129801 concentrations following subcutaneous administration of 2.4 mg CBX129801 every 7 days.
Figure 20:
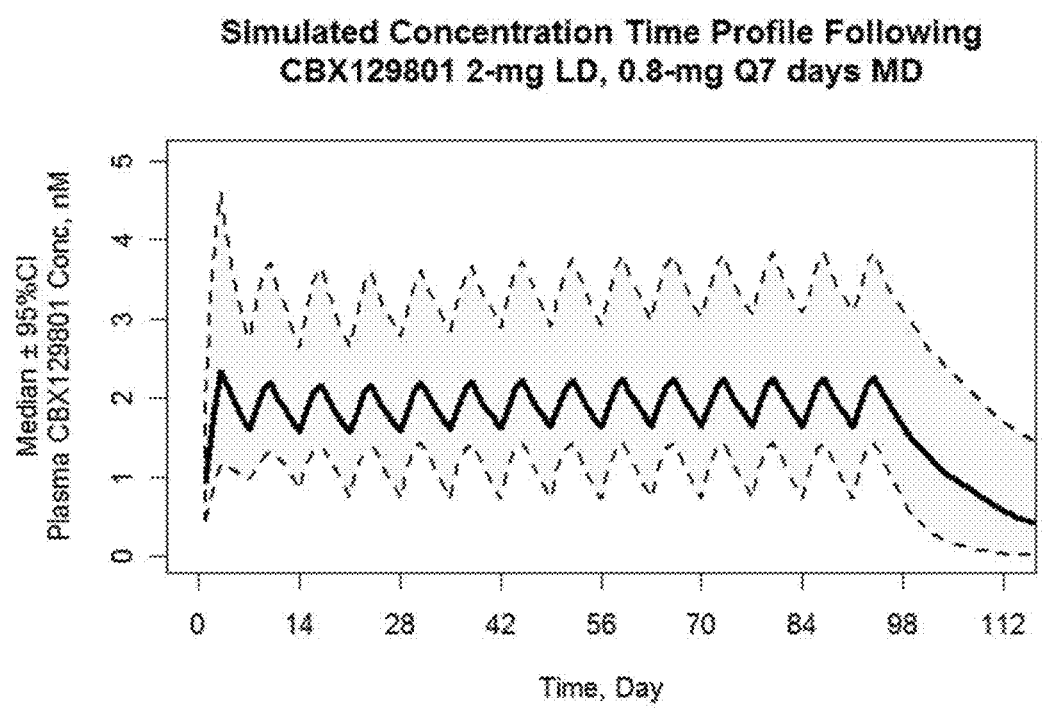
FIG. 20 shows a simulated time course of plasma CBX129801 concentrations following subcutaneous administration of a loading dose of 2.0 mg CBX129801 followed by a maintenance dose of 0.8 mg CBX129801 every 7 days.
Figure 21:
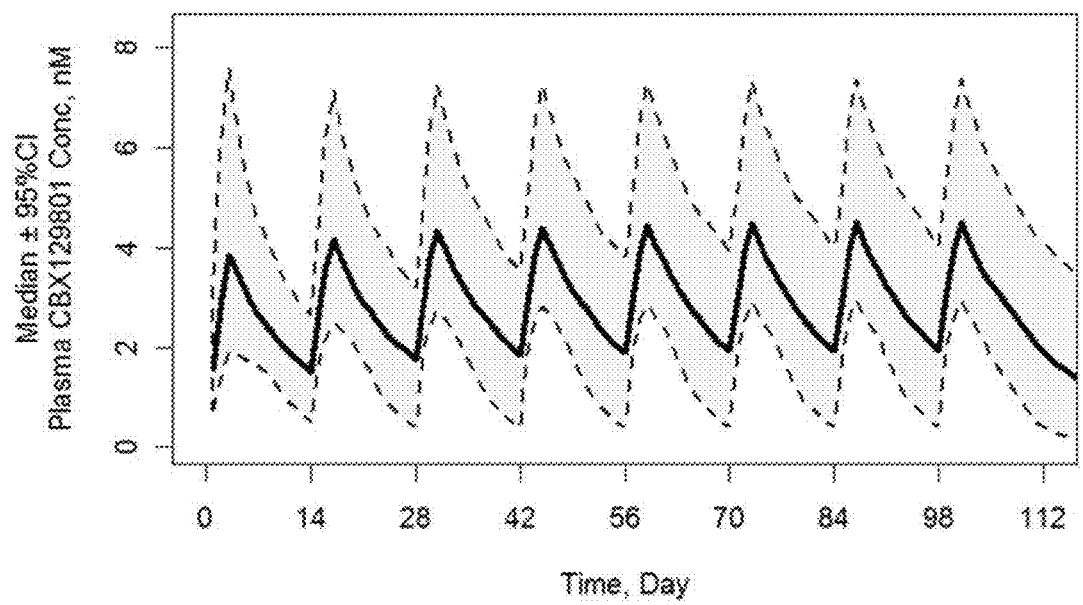
FIG. 21 shows a simulated time course of plasma CBX129801 concentrations following subcutaneous administration of a loading dose of 3.3 mg CBX129801 followed by a maintenance dose of 2.5 mg CBX129801 every 14 days.
Figure 22:
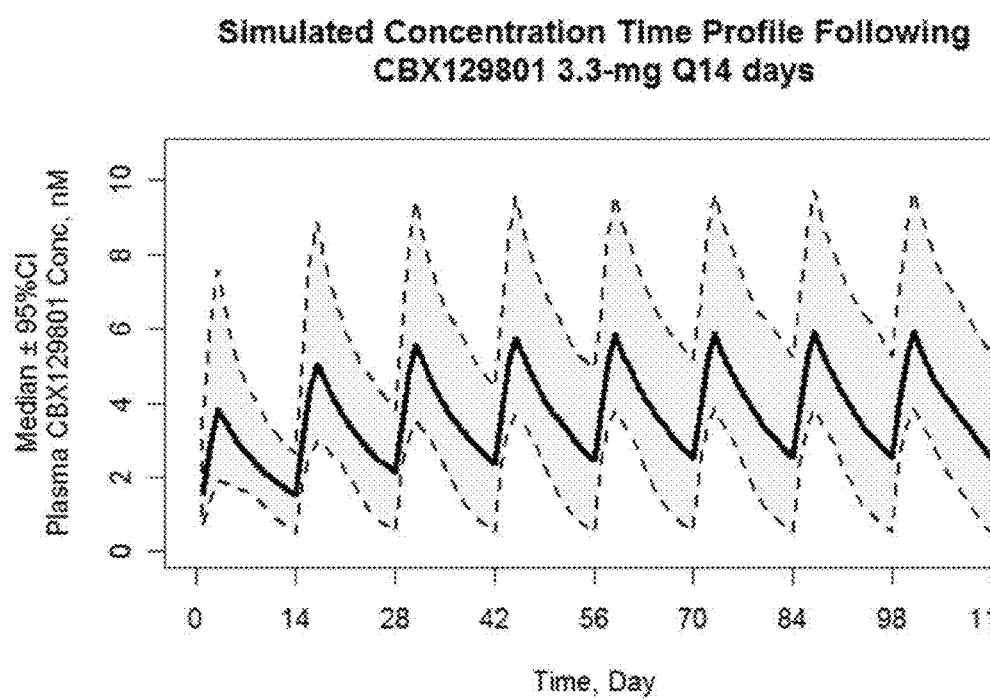
FIG. 22 shows a simulated time course of plasma CBX129801 concentrations following subcutaneous administration of 3.3 mg CBX129801 every 14 days.
Figure 23:
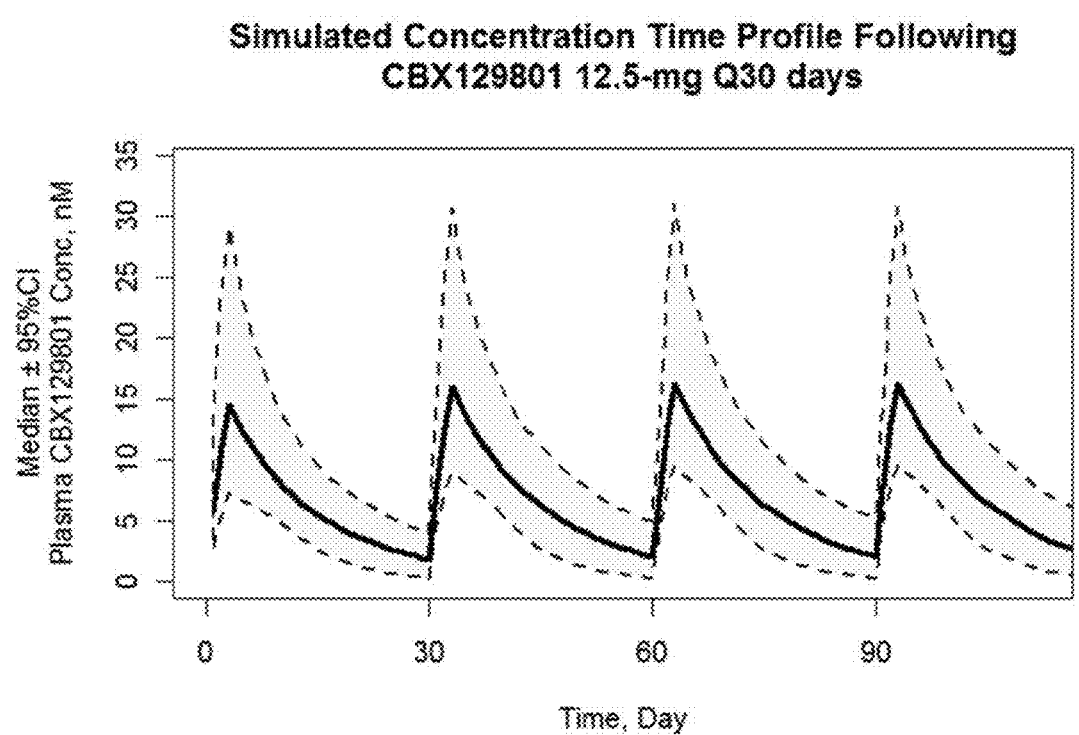
FIG. 23 shows a simulated time course of plasma CBX129801 concentrations following subcutaneous administration of 12.5 mg CBX129801 every 30 days.

The multiple dose $C_{max}$ and $AUC_T$ values increased in a dose-proportional manner over the dose range of 0.3 to 3.3 mg. $C_{max}$ and $AUC_T$ appear to increase linearly with dose (Table E12, FIG. 14 and FIG. 15) following multiple doses between 0.3 to 3.3 mg every 7 days.

The intersubject variability of $C_{max}$, $AUC_\infty$ and $AUC_\tau$ expressed as a percent coefficient of variation (% CV), was less than 46% following a single 1.0 or 3.3 mg dose and following multiple doses of 0.3, 1.0, and 3.3 mg. The % CV values following a single 0.3 mg dose was higher due to samples that were below the limit of quantitation for the assay.

The mean terminal plasma half-life of CBX129801 was approximately 6.37 and 6.92 days following a single dose and between 6.33 and 7.92 days following multiple dosing, suggesting that the half-life does not change following multiple dosing.

Compartment Pharmacokinetic Analysis

The one compartment model with zero order input described the observed data well as indicated by goodness of fit plots and visual predictive check. The parameter estimates (SE) for the pharmacokinetic parameters were CL/F of 0.0522(0.0032) L/hr, $V_c$/F of 17.1 (1.28) L, and D1 of 65.2 (3.63) h. Intersubject variability estimates for CL/F and $V_c$/F were 0.0733 (0.0313) and 0.149 (0.0375), respectively. The D1 value indicates that the input of drug from the site of injection to systemic circulation is 2.7 days. The mean calculated half-life from the compartmental analysis (9.46 days); this value is slightly greater than the non-compartmental analysis.

The time to reach steady-state is ~40 days; with a loading dose the time to reach steady-state could be shortened to approximately 3 days.

Projected Therapeutic Dose and Regimen

A pharmacokinetic equation with a zero-order input, first order elimination was used to describe the log of the observed plasma concentrations over time. The fitted pharmacokinetic parameters were used to simulate the time course of plasma concentration (FIGS. 16-23) and estimate exposure following various treatment regimens.

Example 4

Efficacy Studies of Subcutaneously Administered PEGylated C-Peptide in a Rat Type 1 Diabetic Peripheral Neuropathy Model The biological activity of CBX129801 and its relative potency to unmodified C-peptide were assessed in two studies using the streptozotocin (STZ)-induced diabetes rat model, which develops complications similar to those experienced by type 1 diabetes patients such as polyneuropathy and nephropathy. Specifically for diabetic peripheral neuropathy, the STZ rat model has been used to demonstrate that subcutaneous replacement of rat C-peptide to the C-peptide-deficient rats partially corrected nerve conduction velocity (NCV) deficits in motor and sensory nerves when administered for 2 weeks after 6 weeks of diabetes (Cotter M A et al.: Diabetes 52: 1812-1817, (2003)). A similar outcome was found for motor NCV when human C-peptide was administered subcutaneously for 5 weeks in a preventative strategy (Ido Y et al.: Science 277, 563-566, (1997)).

The objectives of these studies were to: 1) investigate the potential effects of CBX129801 in preventing or improving the NCV decline in diabetic rats, and 2) compare these effects to those produced by unmodified C-peptide at equivalent exposures.

STZ-Induced Diabetic Rats

Male Sprague Dawley rats (Harlan Laboratories, Inc.; Indianapolis, Ind.) weighing approximately 400 g had type 1 diabetes induced on Day 1 by intravenous administration of clinical-grade STZ (Zanosar®; 50 mg/kg in Study #1 and 33 mg/kg in Study #2). On Day 3 (Study #1) or Day 4 (Study #2), blood was collected and $K_3$EDTA plasma was analyzed for endogenous C-peptide levels and animals with C-peptide <0.4 nM were randomized on Day 7 (Study #1) or Day 9 (Study #2) taking into account body weight and blood glucose (criterion in the range 400-600 mg/dL). Randomization was done using Covance's BRAT system. In each study, five rats that did not receive STZ served as the controls.

Insulin (Lantus®, long-acting insulin glargine) was used in both studies and administered subcutaneously in the evening before the start of the 12-hour dark cycle in the animal room (time period when most food consumption takes place). In Study #1, rats were initiated on insulin after there were a number of animal deaths starting early in the study (3 days into the treatment period). All animals were receiving 3 U/day of insulin by the end of the study. In Study #2, in part to avoid the mortality observed in Study #1, animals were started on insulin when blood glucose reached 550 mg/dL. As animals started on insulin, for the most part, they were treated collectively meaning an increase in insulin that was done to keep blood/plasma glucose in check (e.g., <550 mg/dL) was applied to all animals. All animals were receiving 5 U/day of insulin by the end of the study. Additionally to limit dehydration when needed throughout the studies, warm sterile saline (volume determined by veterinarian) was administered to animals, and in particular in Study #2, to animals 24 hours prior to undergoing surgery for pump implantation.

Test Articles

All test articles were administered subcutaneously starting on Day 10 in the dorsal-scapular region of the rat. PEGylated human C-peptide (CBX129801; lot #1007-119 for Study #1; GMP batch (Example 1) for Study #2) and PEGylated rat II C-peptide were administered by injection (1 mL/kg) either once weekly (Study #1) or every 3 days (Study #2; CBX129801 only). Unmodified (non-PEGylated) human C-peptide and rat II C-peptide (Study #1 only) were administered via implanted osmotic pumps (Alzet®, model 2ML4; 2.5 L/h) that were replaced every 4 weeks. All test articles were prepared for use at the study site with sterile phosphate-buffered saline as the vehicle. Dose concentrations were corrected for purity based on the certificates of analysis.

In-Life Assessments

Clinical Observations: Animals were checked daily or more frequently as needed for general health status including signs of pain or distress. Body weights were taken pre-STZ treatment on Day 1, as part of the randomization process on Days 7/9, Day 11 (one day post first dose), and weekly thereafter. Food consumption was noted on the same schedule as body weights.

Blood Glucose: A drop of blood was collected via tail vein on Days 3/4, Days 7/9, Day 11, and weekly thereafter from animals fasted for a minimum of 3 hours. Blood glucose determinations were made using either a hand-held glucometer (Accu-chek® Aviva system, Roche) that had a maximum reading of 600 mg/dL or a clinical device (Hitachi 912 Clinical Chemistry Analyzer).

PEGylated C-peptide and Unmodified C-peptide Measurements: Blood (350 µL) was collected via tail vein from animals fasted for a minimum of 3 hours into $K_3$EDTA tubes and placed on ice prior to processing to plasma. Plasma samples were stored at −70° C. prior to shipment on dry ice to Micro-Constants, Inc. (San Diego, Calif.) for analysis. For all animals on Days 3/4 and Days 7/9, the levels of endogenous rat C-peptide were measured using a commercially available kit for rat C-peptide (Mercodia AB, Sweden; catalog no. 10-1172-01). During the treatment period, periodic blood samples were collected from the animals to determine pharmacokinetic profiles for the various treatment regimens with PEGylated and unmodified C-peptide. Methods were developed for four matrices in rat plasma depending on whether the source of C-peptide was rat or human, and if the peptide was PEGylated. The plasma levels of unmodified and PEGylated rat C-peptides were measured with the Mercodia kit noted above for rat C-peptide; unmodified and PEGylated human C-peptides were measured with the Mercodia kit for human C-peptide (catalog no. 10-1136-01). The kits were used according to the manufacturer's instructions for the unmodified C-peptides. For the PEGylated C-peptides, the kits were modified by using PEGylated C-peptides for the quality control and standard samples, thus generating a standard curve specific for analysis of samples containing the PEGylated material.

Nerve Conduction Velocity (NCV)

Electrophysiological endpoints, including NCV, were measured at baseline (Days 8-10 [before treatment on Day 10]), 4 weeks (Study #1 only), 8 weeks, and 12 weeks (Study #2 only) after initiation of treatment in the hindlimb (digital nerve, tibial nerve [Study #1 only]) and tail (caudal nerve). Animals were anesthetized with isoflurane and placed in a prone position during all recording sessions. Respiration and temperature were monitored during the electrophysiologic recording procedure. Personnel evaluating NCV were blinded to the treatment assignment of each rat assessed. In Study #2, all animals were implanted with pumps (if applicable to treatment assignment) during the same anesthesia session used to measure NCV. (In Study #1, pump implantation and NCV measurements were done on back-to-back days.)

Digital Nerve Action Potential: This measure was recorded with the active recording electrode positioned at the ankle, behind the lateral malleolus and the stimulating cathode at the base of the second digit of the hindpaw. Velocity was calculated by dividing the distance between the stimulating cathode and the active electrode by the absolute onset latency of the initial depolarizing current.

Caudal Nerve Action Potential: This measure was recorded with the active recording electrode positioned 10 mm below the hair line on the tail (determined visually) and the stimulating cathode 60-70 mm further distal. Velocity was calculated by dividing the distance between the stimulating cathode and the active electrode by the absolute onset latency of the initial depolarizing current.

Tibial Motor Conduction (Study #1 only): This measure was recorded with the active electrode positioned in the intrinsic muscles of the hindpaw and the stimulating cathode proximal to the ankle, behind the lateral malleolus.

Platinum needle electrodes (Grass-Telefactor, Co.), with impedances of approximately 50 kohms @ 1,000 Hz, were used as both active and reference leads for all peripheral nerve recordings. The placement of the active, reference and ground electrodes were tailored to each modality and positioned with respect to bony landmarks in each animal. Neuroelectric signals were impedance matched using unity gain preamplifiers, appropriately band-passed using multi-pole filters, and further differentially amplified using a gain factor of 0.5-50 K. The filter settings were adjusted for each modality. Common mode rejection levels and gain factors were adjusted to minimize 60-Hz interference and to optimize the signal-to-noise ratio for each recording series. The amplified signal was time-locked to the evoking stimulus, multiplexed into selected channels and digitized at a rate greater than 5 times the highest frequency sampled. The data were scanned for artifacts (using a predetermined rejection level; 80% of the digitized window) and digitally averaged for an epoch appropriate for the modality under study. The number of individual traces included in each average was adjusted for each measure to optimize the signal-to-noise ratio and facilitate the accurate assessment of both onset latency and peak amplitude measures.

All electrophysiologic data were scored following optimization of the signal. Onset latency was measured from the stimulus artifact to the initiation of the depolarization to the nearest 0.01 millisecond. Amplitude was measured from baseline to the peak of the depolarization to the nearest 0.01 V for sensory responses, and to the nearest 0.01 mV for motor responses. All measurements were conducted with an internal computer cursor that follows the digitized trace. All waveforms were stored digitally and available for further off-line analysis.

Statistical Analysis

Means, standard deviations (SD), and standard errors of the mean (SEM) were calculated using Excel software. A one-way ANOVA with Dunnett's post-hoc test (Prism 5 for Mac OS X, GraphPad Software, Inc., La Jolla, Calif.) was used to compare the results for absolute or percent change of NCV from baseline in the treatment groups as compared to the vehicle group, with significance at $p<0.05$.

Treatment Groups

Study #1: A total of 65 animals were used; 60 of which were diabetic as induced by STZ injection. The seven treatment groups, N per group, and dose amount, frequency, and volume of test article are shown in Table E13.

TABLE E13

Treatment groups in Study #1

| Group | N | Test Article | Dose (mg/kg) | Frequency | Dose Volume (mL/kg) |
|---|---|---|---|---|---|
| 1 | 5 | Vehicle | 0 | Weekly[a] | 1.0 |
| 2 | 10 | Vehicle | 0 | Weekly[a] | 1.0 |
| 3 | 10 | CBX129801 | 1.3 | Weekly[a] | 1.0 |
| 4 | 10 | CBX129801 | 4.0 | Weekly[a] | 1.0 |
| 5 | 10 | UM Human CP | 1.5 | Over 24 h | Pump (2.5 μL/h) |
| 6 | 10 | UM Rat CP | 0.3 | Over 24 h | Pump (2.5 μL/h) |
| 7 | 10 | PEG Rat CP | 0.3 | Weekly[a] | 1.0 |

[a]In the first week, two injections were given (Day 10 and Day 13).
UM = unmodified; CP = C-peptide; PEG = polyethylene glycol.

Study #2: A total of 110 animals were used; 105 of which were diabetic as induced by STZ injection. The eight treatment groups, N per group, and dose amount, frequency, and volume of test article are shown in Table E14.

TABLE E14

Treatment groups in Study #2

| Group | N | Test Article | Dose (mg/kg) | Frequency | Dose Volume (mL/kg) |
|---|---|---|---|---|---|
| 1 | 5 | None | NA | NA | NA |
| 2 | 15 | Vehicle | 0 | Q3D | 1.0 |
| 3 | 15 | CBX129801 | 0.04 | Q3D | 1.0 |
| 4 | 15 | CBX129801 | 0.2 | Q3D | 1.0 |
| 5 | 15 | CBX129801 | 0.6 | Q3D | 1.0 |
| 6 | 15 | UM Human CP | 0.15 | Over 24 h | Pump (2.5 μL/h) |
| 7 | 15 | UM Human CP | 0.75 | Over 24 h | Pump (2.5 μL/h) |
| 8 | 15 | UM Human CP | 2.5 | Over 24 h | Pump (2.5 μL/h) |

NA = not applicable; Q3D = every 3 days; UM = unmodified; CP = C-peptide.

Results—Study #1
Animal Survival and Clinical Observations

Of the 65 rats receiving STZ, 63 of them had endogenous (rat) C-peptide levels <0.4 nM at Day 3 (33 rats had levels <0.1 nM). The STZ-induced diabetic state was associated with hyperglycemia and loss of body weight with some mortality in all groups in the first few weeks (Table E15). STZ rats in the unmodified C-peptide groups were most affected, presumably due to exacerbated dehydration secondary to anesthesia for surgical pump implantation; no comparative analysis of NCV was done for these two groups (Groups 5 and 6) due to the few survivors. There were no remarkable differences in food consumption between the STZ rat groups; however, the amount of food consumed on average was 1.5-2 times that of the control group throughout the 8-week treatment period.

TABLE E15

Animals Surviving to End of Study and Clinical Observations

| Group | Number of Surviving Animals | Blood Glucose (mg/dL)[a] Day 7[b] | Blood Glucose (mg/dL)[a] Day 66[c] | Body Weights (g)[a] Day 7[b] | Body Weights (g)[a] Day 66 |
|---|---|---|---|---|---|
| 1 | 5[d] | 101 ± 5 | 112 ± 4 | 411 ± 2 | 449 ± 10 |
| 2 | 9 | 505 ± 10 | 736 ± 33 | 361 ± 4 | 335 ± 8 |
| 3 | 5 | 494 ± 9 | 683 ± 53 | 360 ± 3 | 345 ± 8 |
| 4 | 9 | 493 ± 11 | 714 ± 21 | 365 ± 3 | 340 ± 6 |
| 5 | 1 | 506 ± 13 | 644[e] | 361 ± 3 | 341[e] |
| 6 | 3 | 486 ± 14 | 638 ± 18 | 358 ± 3 | 361 ± 9 |
| 7 | 7 | 488 ± 8 | 714 ± 21 | 362 ± 3 | 336 ± 3 |

[a]Results are mean ± standard deviation (SD).
[b]Includes all animals originally in group.
[c]Measured in plasma.
[d]Controls (non-STZ) had no deaths.
[e]No SD determined (N = 1).

Insulin was administered to all animals at a dose of 1 U/day starting in the first week of test article treatment. This insulin dose was increased to 2 U/day after 2 weeks and to 3 U/day after 3 weeks. All surviving animals completed the 8-week treatment period receiving 3 U/day of insulin.

CBX129801 and C-Peptide Levels

The doses of CBX129801 (1.3 and 4.0 mg/kg/week) used in this study were higher than the dose for the PEGylated rat C-peptide (0.3 mg/kg/week) because of the differences in amino acid sequence between rat and human C-peptides (i.e., 9 substitutions in the 31 amino acids). The average maximum plasma concentration assessed 2 days after dosing in the third week in the low-dose CBX129801, high-dose CBX129801, and PEGylated rat C-peptide groups was approximately 129 nM, 431 nM, and 12 nM, respectively. The average minimum plasma concentration at the end of the study was approximately 22 nM, 94 nM, and 2 nM in the low-dose CBX129801, high-dose CBX129801, and PEGylated rat C-peptide groups, respectively. The loss of most of the animals in the STZ rat groups receiving unmodified C-peptides (Groups 5 and 6) precludes a comparison of the potency between PEGylated C-peptide and unmodified C-peptide.

Nerve Conduction Velocity

The STZ rats in the vehicle and PEGylated C-peptide groups (N=5-9/group) had NCV slowing in both nerves after 8-9 days of diabetes as compared to controls (i.e., established NCV impairment at baseline before treatment). The NCV deficit at baseline for these STZ rats relative to control rats was approximately 16% (29.0 m/s vs. 34.4 m/s) for the digital nerve and 19% (42.7 m/s vs. 53.0 m/s) for the caudal nerve. The tibial nerve did not show any evidence of changing with treatment and results are therefore not presented.

As shown in Table E16, vehicle-treated STZ rats had decreased digital NCV and slightly increased caudal NCV over the 8-week period. Treatment with both human and rat PEGylated C-peptides had a statistically significant effect on preventing the impairment in digital NCV consequent to disease progression. In particular for high-dose CBX129801 there was a partial reversal of the baseline NCV deficit (28.6 m/s at baseline and 30.1 m/s at 8 weeks, vs. 32.9 m/s for controls at 8 weeks). The changes relative to baseline in caudal NCV with PEGylated C-peptide treatment were not significant although there was a trend towards restoring the NCV deficit (e.g., 43.8 m/s at baseline and 46.1 m/s at 8 weeks for high-dose CBX129801, vs. 56.8 m/s for controls at 8 weeks).

TABLE E16

Percent Changes in Digital and Caudal Nerves Relative to Baseline

| Treatment Group | N | % Change in NCV at 8 Weeks from Baseline[a] | |
|---|---|---|---|
| | | Digital | Caudal |
| Vehicle | 9 | −13.4 ± 8.7 | 2.5 ± 10.1 |
| 1.3 mg/kg/wk CBX129801 | 5 | 0.5 ± 11.7* | 11.2 ± 12.5 |
| 4.0 mg/kg/wk CBX129801 | 9 | 5.4 ± 6.6* | 6.4 ± 11.0 |
| 0.3 mg/kg/wk PEG Rat C-peptide | 7 | −3.0 ± 6.0* | −0.8 ± 14.4 |

[a]Mean ± standard deviation, calculated as the mean of the % change of individual animals.
*p < 0.05, vs. vehicle group.

Figure 24:
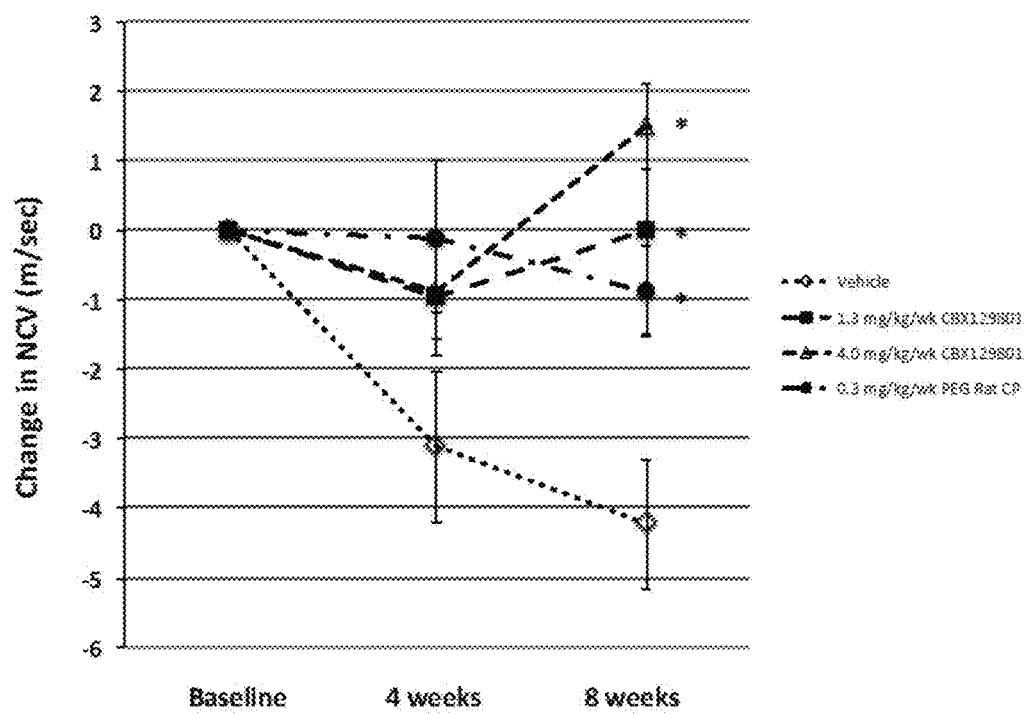
FIG. 24 shows the change in NCV at 4 and 8 weeks of treatment vs. baseline for groups of rats treated with CBX129801 and PEGylated rat C-peptide. * $p<0.05$, vs. vehicle (control) group.

The slowing of digital NCV observed in the vehicle-treated group was mitigated in the PEGylated C-peptide groups at 4 weeks (FIG. 24; mean±standard error of the mean; p<0.05), but differences were not statistically significant. Continued treatment from 4 to 8 weeks reversed any apparent short-term NCV deficits and there were overall unchanged or improved NCVs at 8 weeks as compared to baseline. A comparable treatment effect on NCV has been found in previous studies with unmodified C-peptide in the STZ rat model and also the BB/Wor rat model (spontaneous development of type 1 diabetes).

Conclusions

Subcutaneous administration of CBX129801 in a rat model of type 1 diabetes prevented slowing of sensory NCV consequent to disease progression. PEGylated rat C-peptide was also efficacious. These results demonstrate that the biological activity of the native C-peptide is retained when the peptide is PEGylated, which extends its circulating half-life and thereby lessens the frequency of replacement dosing.

Results—Study #2

Animal Survival and Clinical Observations

Of the 105 rats receiving STZ, the endogenous (rat) C-peptide levels were <0.4 nM at Day 4 in 41 animals (none had levels <0.1 nM). This number increased to 77 by Day 8 as the diabetic state developed further; those animals with endogenous C-peptide levels >0.5 nM were reassessed a week later and only two animals had elevated C-peptide levels (0.57 nM and 0.61 nM). The STZ-induced diabetic state was associated with hyperglycemia and loss of body weight (Table E17). There were 5 deaths (one each in Groups 4-6; two in Group 7). There were also two technical issues in Groups 6-8 in which animals received pumps; the first was a mix-up of test article dose (between five animals in each Group 6 and Group 8) and the second was a batch of nine defective pumps. Thus, the N for these groups is significantly less Groups 2-5.

TABLE E17

Animals at End of Study and Clinical Observations

| Group | Number of Final Animals | Blood Glucose (mg/dL)[a] | | Body Weights (g)[a] | |
|---|---|---|---|---|---|
| | | Day 8[b] | Day 92 | Day 8[b] | Day 92 |
| 1 | 5[c] | 101 ± 3 | 103 ± 4 | 418 ± 3 | 502 ± 9 |
| 2 | 15 | 452 ± 11 | 415 ± 29 | 374 ± 3 | 436 ± 6 |
| 3 | 15 | 445 ± 13 | 463 ± 29 | 380 ± 4 | 442 ± 8 |
| 4 | 14 | 460 ± 12 | 424 ± 49 | 378 ± 3 | 439 ± 7 |
| 5 | 14 | 466 ± 14 | 472 ± 32 | 375 ± 5 | 435 ± 8 |
| 6 | 5 | 457 ± 8 | 476 ± 25 | 371 ± 3 | 441 ± 5 |
| 7 | 12 | 463 ± 12 | 533 ± 24 | 374 ± 3 | 433 ± 8 |
| 8 | 6 | 467 ± 10 | 498 ± 19 | 379 ± 4 | 443 ± 8 |

[a]Results are mean ± standard error of the mean.
[b]Includes all animals originally in group.
[c]Controls (non-STZ) had no deaths.

Insulin was administered to animals at a starting dose of 1.5 U/day when their blood glucose reached 550 mg/dL. Once on insulin, an animal was treated along with the collective group receiving insulin; there were occasions when an animal's blood glucose would drop to <300 mg/dL and the veterinarian withheld a daily insulin dose. Based on blood or plasma glucose readings near 550 mg/dL for the collective group, the insulin dose was increased by 1-2 U/day over the first 7 weeks of the study reaching a maximum of 6 U daily. All surviving animals completed the 12-week treatment period receiving 5 U/day of insulin.

CBX129801 and C-Peptide Levels

Figure 25:
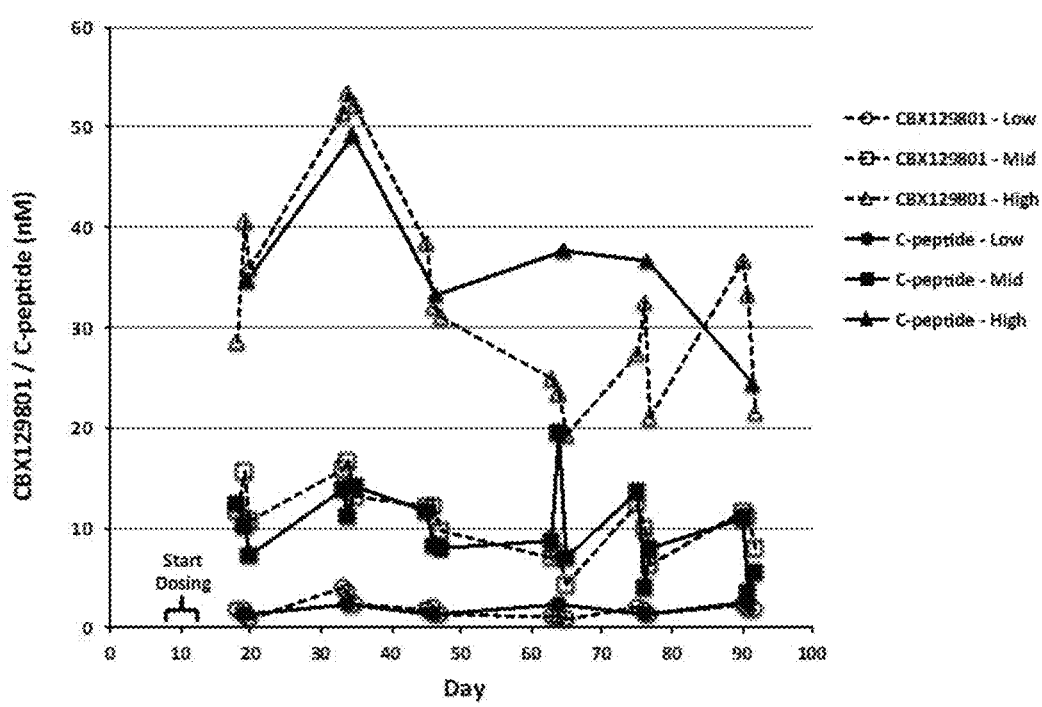
FIG. 25 shows drug levels in rats during 12 weeks of subcutaneous treatment with CBX129801 by injection (every 3 days) and C-peptide by implanted osmotic pumps. Blood samples were taken periodically during the treatment period and plasma obtained for determination by ELISA of CBX129801 (PEGylated C-peptide) or C-peptide. The three dose levels were distinct and there was similar exposure between PEGylated and unmodified C-peptide within each dose level group (low, mid, high).

The goal of the selected doses in the PEGylated C-peptide and unmodified C-peptide groups (Table E14) was to obtain a matching low, mid, and high dose level that would facilitate an investigation of NCV across a dose range and compare the potency of the two C-peptide forms. As shown in FIG. 25, there were three distinct ranges of exposure obtained with both injection of CBX129801 every 3 days and continuous delivery of unmodified C-peptide via implanted osmotic pump.

Nerve Conduction Velocity

The STZ rats in the vehicle, PEGylated C-peptide, and unmodified C-peptide groups (N=15/group) had NCV slowing in both nerves after 8-10 days of diabetes as compared to controls (i.e., established NCV impairment at baseline before treatment). The NCV deficit at baseline for these STZ rats relative to control rats was approximately 14% (27.4 m/s vs. 31.7 m/s) for the sensory digital nerve and 13% (44.9 m/s vs. 51.4 m/s) for the sensory/motor caudal nerve.

Figure 26:
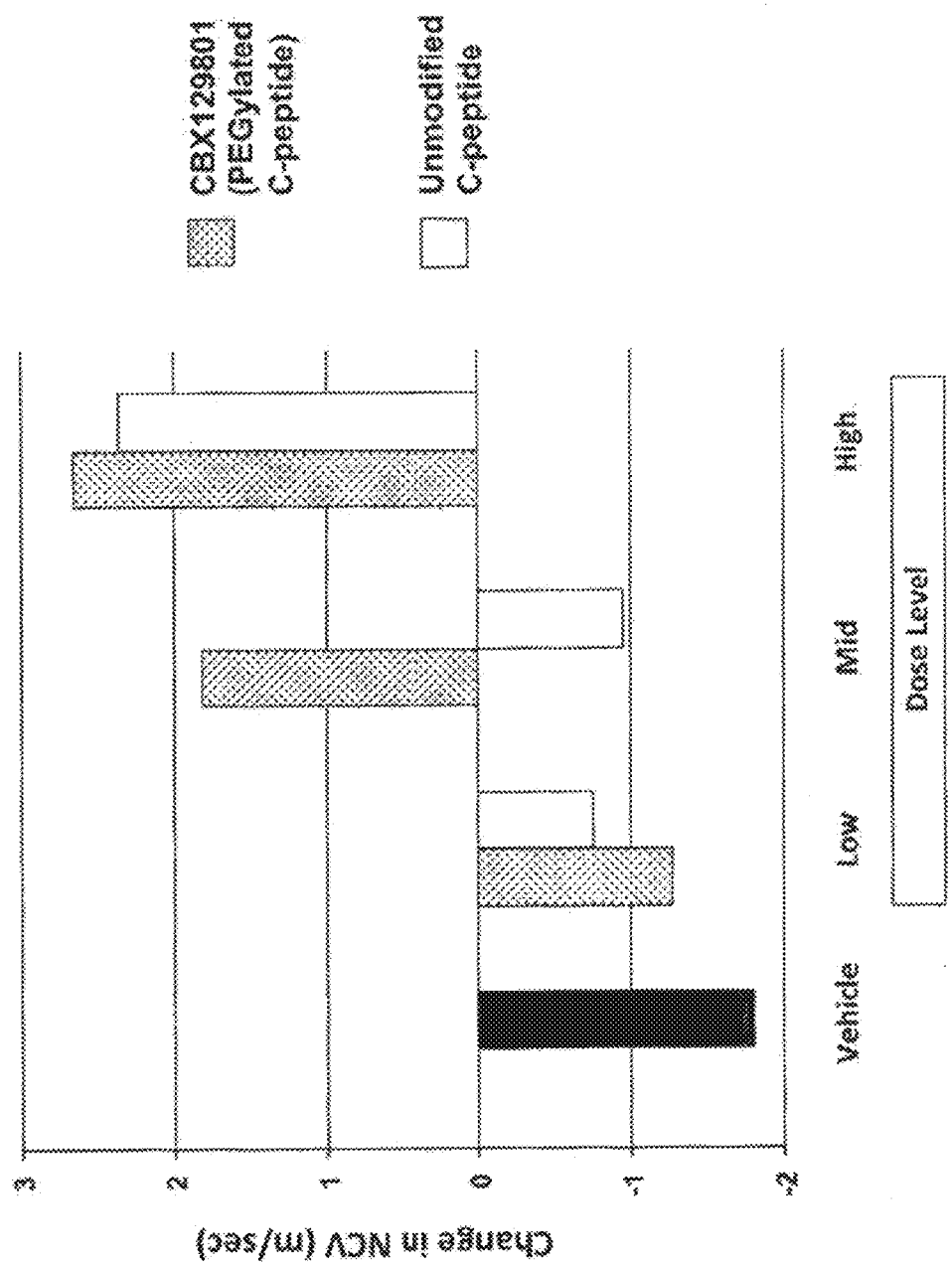
FIG. 26 shows the change in sensory/motor caudal nerve conduction after 12 weeks of treatment vs. baseline (8-10 days post STZ induction) in STZ-induced diabetic rats.
Figure 27:
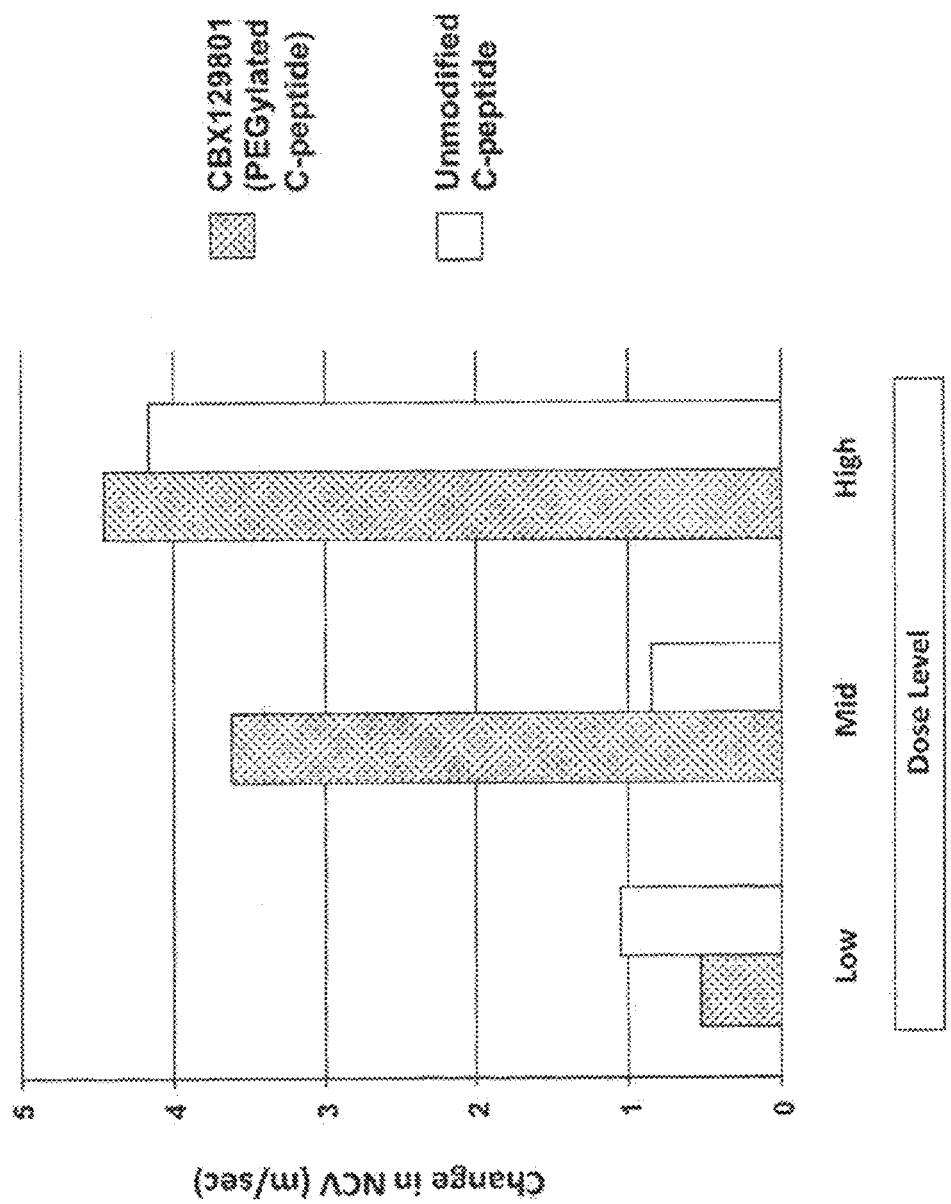
FIG. 27 shows the change in sensory/motor caudal nerve conduction, treated groups vs. vehicle after 12 weeks of treatment in STZ-induced diabetic rats.
Figure 28:
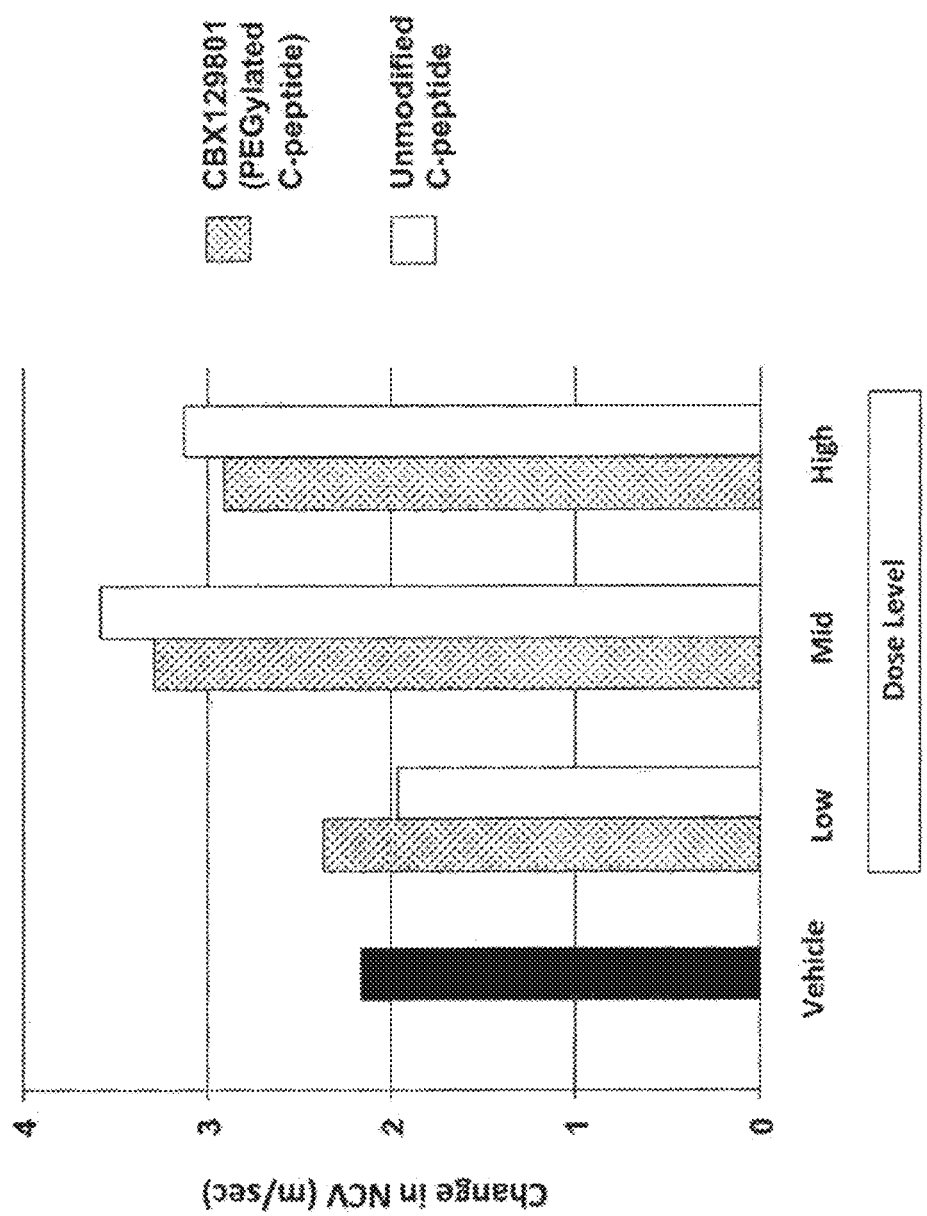
FIG. 28 shows the change in digital nerve conduction vs. baseline after 12 weeks of treatment in STZ-induced diabetic rats.

As shown in FIG. 26, the vehicle-treated animals had a decrease in caudal NCV of approximately 1.8 m/s from baseline over the 12 weeks of treatment. In the PEGylated and unmodified C-peptide groups, there was also a decrease in NCV for the low dose animals vs. baseline, albeit less than the controls. At the mid dose, CBX129801 had an increase in NCV over the 12 weeks whereas unmodified C-peptide had a decrease in NCV. The improvement in NCV in the high dose groups was similar between the PEGylated and unmodified C-peptides. The dose-dependent trend for improved NCV with comparable efficacy between the two forms of C-peptide at the higher dose is also demonstrated in FIG. 27. The magnitude of the NCV change was approximately 4 m/s, which was comparable to that in Study #1 for the digital nerve. A similar trend for improved NCV in the caudal nerve with increasing C-peptide dose was observed after 8 weeks of treatment, but not as pronounced. Additionally in the digital nerve, there was a small improvement in NCV over the 12 weeks of treatment without a strong association to dose (FIG. 28).

Conclusions

This study supports the result of Study #1 that CBX129801 (PEGylated C-peptide) has biological activity. Moreover, this study demonstrates that CBX129801 has comparable biological activity to the unmodified, native C-peptide.

Example 5

Efficacy Studies of Subcutaneously Administered C-Peptide in a Diabetes-Induced Nerve Dysfunction in BB/Wor Rats Different dose regimens for C-peptide (rat, unmodified) were evaluated in regard to restoration of nerve function and structure in the BB/Wor rat, which is a model of spontaneous type 1 diabetes associated with insulin deficiency and insulitis due to autoimmune destruction of the pancreatic beta cells. The animals become severely hyperglycemic, hypoinsulinemic, and ketotic. Thus, the model closely resembles the human situation including associated vascular, renal, retinal, and neuropathic degenerative complications.

The objectives of this studies were to investigate whether: 1) s.c. continuous administration of 75 nmol rat C-peptide/kg/24 hr has similar efficacy as an equivalent amount of C-peptide given divided into 3 s.c. injections per day, and 2) whether the same amount of C-peptide given as one daily injection has the similar efficacy.

BB/Wor Diabetic Rats

Fifty prediabetic male BB/Wor rats and ten age- and sex-matched non-diabetes prone BB/Wor rats were obtained from Biomedical Research Models (Worcester, Mass., USA). All animals were maintained in air-filtered metabolic cages with ad libitum access to rat chow (Wayne lab blox F.6, Wayne Food Division, Chicago, Ill., USA) and water. Body weight and urine glucose were monitored daily to ascerta in the onset of diabetes. After onset of diabetes, at 73±6 days of age, the diabetic animals were given protamin zinc insulin (Blue Ridge Pharmaceuticals, NC, USA) daily in titrated doses (0.5-3.5 IU) in order to maintain blood glucose levels between 20-25 mmol/L and to prevent ketoacidosis. Blood glucose was measured every two weeks and at the end of the study. Immediately after onset of diabetes, rats were randomly assigned to treatment groups (Table E18), ten animals per group. The diabetic rats received saline by pump (group B; untreated rats) or 75 nmol synthetic rat C-peptide per kg/day (>95% purity by RP-HPLC produced by Multiple Peptide Systems, San Diego, Calif.). The rat C-peptide was dissolved in phosphate-buffered saline and delivered either via subcutaneously implanted osmotic pumps (Alza Corporation, Palo Alto, Calif., USA) (group D) or via subcutaneous injections once per day (group C) or divided into 3 equal doses (group E). Non-diabetic control animals (n=10) did also receive saline by osmotic pumps (group A).

TABLE E18

Treatment Groups

| Group | |
|---|---|
| A | Non-diabetic rats |
| B | Diabetic rats; no treatment |
| C | Diabetic rats given 75 nmol rat C-peptide/kg s.c. once daily |
| D | Diabetic rats given 75 nmol rat C-peptide/kg/24 hr s.c. by osmopump |
| E | Diabetic rats given 75 nmol rat C-peptide/kg/24 hr s.c. divided into 3 equal doses |

Rat C-peptide plasma concentrations were determined by a commercially available RIA kit (Linco Research, St. Charles, Mo., USA). To minimize hypovolemic effects only two plasma samples were collected from each animal. For groups A, B, and D samples were collected in the morning, 15 min apart. For groups C and E sampling was distributed among the animals to cover a span of time points: from 0-24 h and 0-3 h following injection of C-peptide for groups C and E, respectively Does Selection In order to restore physiological plasma levels of C-peptide in type 1 diabetes patients a dose of 600 nmol/24 hr s.c. has been used in several clinical trials. This dose equals ~8 nmol/kg/24 hr in a normal weight patient. Since the overall metabolic rate is higher in rodents than humans, it was concluded that a higher dose would be required to obtain physiological plasma levels in rats. Thus, in previous studies on C-peptide's effect on nerve function the rats were given 75 nmol rat C-peptide/kg/24 hr s.c. continuously by osmotic pumps, which resulted in a 74% restoration of C-peptide concentrations Electrophysiological Studies Baseline nerve conduction velocity was measured within 24 hr of onset of diabetes and hence once weekly to 4 weeks and then at 6 and 8 weeks of diabetes. Measurements and tissue collection (see below) were performed in the morning, prior to the daily injection in group C, and between first and second injection in group E. Nerve conduct ion was measured in the left sciatic-tibial nerves under temperature controlled (35-37° C.) conditions. The left sciatic nerve was stimulated supramaximally (8V) with square wave pulses (20 Hz) at the sciatic notch and the tibial nerve at the ankle using an electromyography machine (5200 A, Cadwell Laboratory, Kennewick, Wash., USA). The compound evoked motor responses were obtained from the first interosseous space and were measured from stimulus artifact to onset of the M-wave deflection. Each NCV value represented the averaging of 8 or 16 recordings and was calculated by subtracting the distal from the proximal latency divided by the distance between the two stimulating electrodes, giving NCV in m/s.

Tissue Collection and Teased Fiber Examination

After 2 months of treatment the animals were sacrificed with a napentobarbital overdose (100 mg/kg body wt. i.p.) and both sciatic nerves were dissected, weighed and snap-frozen in liquid nitrogen and stored at −70° C. for measurement of Na+,K+-ATPase activity. The right sural nerve was fixed in situ with 2.5% glutaraldehyde in 0.1 M cacodylate buffer (pH 7.40), dissected and immersion fixed in the same fixative overnight at 4° C. and post-fixed in cacodylate buffered (0.1 M) 1% osmium tetroxide (pH 7.40) overnight at 4° C., The sural nerve was dehydrated and single myelinated fibers were teased in unpolymerized Epon as previously described. All tissue samples were coded in order to mask animal identity prior to biochemical and teased fiber analysis.

A mean of 257±2 myelinated fibers were teased from each sural nerve and scored for specific changes, providing a three dimensional assessment of myelinated fiber pathology. Representing the temporal sequence and increasing severity of myelinated fiber pathology, they were classified as follows: normality, paranodal swelling, paranodal demyelination, excessive myelin wrinkling, intercalated internodes, segmental demyelination, Wallerian degeneration, and regeneration. Each fiber was scored as to its most severe change and expressed as a percentage of total fibers. The teased fiber analyses is a more sensitive technique than assessments by light microscope that enables the detection of changes which are not yet translated into the more robust light microscopic changes.

Assessment of Nerve $Na^+$, $K^+$-ATPase Activity

For assessment of Nerve $Na^+$, $K^+$-ATPase activity, nerve samples were homogenized in 2 mL of 0.2 M sucrose and 0.02 M Tris-HCl at pH 7.5. Ten to 20 µL of the homogenate was assayed enzymatically for total ATPase activity in 1 mL of 100 mM NaCL 10 mM KCl, 2.5 mM $MgCl_2$, 1 mM ATP, 1 mM phosphoenolpyruvate, 30 mM imidazole HCl buffer (pH 7.3), 0.15 mM NADH, 50 µL lactate dehydrogenase and 30 µg pyruvate kinase. To measure ouabain-inhibitable ATPase activity, 20 µL of 25 mM ouabain was added. $Na^+$, $K^+$-ATPase activity was defined as the difference in activity before and after addition of ouabain and was expressed as µmol ADP formed per gram of wet weight per hour. Assays were performed in duplicates.

Nerve Conduction Velocities

During the C-peptide treatment there was no effect on blood glucose levels or daily insulin requirements observed. Diabetes caused a significant reduction in motor and sensory nerve conduction velocities (NCV) in the untreated rats, C-peptide significantly prevented the NCV slowing (p<0.001) and there were no significant differences between the effects of the different C-peptide regimens. The functional changes were accompanied by changes in nerve $Na^+$, $K^+$-ATPase activity and morphology. $Na^+$, $K^+$-ATPase activity was significantly improved by 2 months of C-peptide treatment (p<0.001) and the effect was similar for all dose regimens.

There was a 6-fold diabetes-induced increase in the number of abnormal nerve fibers (P<0.001) in the diabetic untreated rats, with findings of marked paranodal swelling and demyelination in the diabetic untreated nerve fibers. These structural changes were completely prevented by continuous administration of C-peptide, whereas C-peptide given once daily also ameliorated the degeneration but slightly less effectively. Axonal degeneration in the nerves from the untreated diabetic rats was also evident as an augmented excessive myelin wrinkling and increased Wallerian degeneration. C-peptide treatment, regardless of dose regimen, completely prevented these diabetes-induced changes.

Evaluation of the functional and morphological changes together in a composite score revealed that there was a significant beneficial effect of C-peptide on nerve dysfunction caused by diabetes. These effects were independent of mode of C-peptide administration. However, the efficacy for C-peptide given once daily was significantly lower than when C-peptide was given 3 times per day or as a continuous infusion (p<0.033).

We claim:

1. A method of treating a diabetic subject having a microvascular impairment disorder, comprising subcutaneously administering to the subject a therapeutically effective amount of PEGylated C-peptide, wherein the PEGylated C-peptide has the structure:

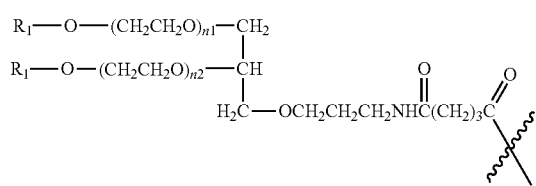

wherein each $R_1$ is alkyl;
n1 is 200 to 800;
n2 is 200 to 800; and
the polyethylene glycol (PEG) moiety

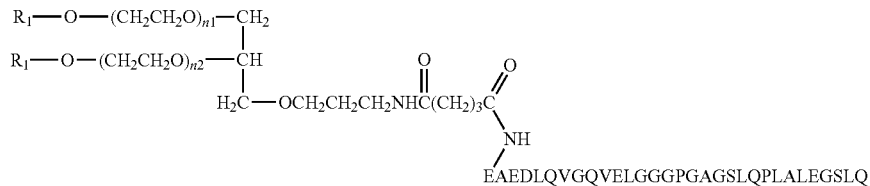

has a molecular weight of about 40 kDa to about 50 kDa.

2. The method of claim 1, wherein the $C_{ave}$ of PEGylated C-peptide is between about 0.44 nM and about 12.22 nM, or between about 2.0 nM and about 5.9 nM.

3. The method of claim 2, wherein the $C_{min}$ of PEGylated C-peptide is between about 1.7 nM and about 4.9 nM.

4. The method of claim 1, wherein the $C_{min}$ of PEGylated C-peptide is between about 0.34 nM and about 9.0 nM.

5. The method of claim 1, wherein the $C_{max}$ of PEGylated C-peptide is between about 0.5 nM and about 14.5 nM.

6. The method of claim 5, wherein the $C_{max}$ of PEGylated C-peptide is between about 2.3 nM and about 6.7 nM.

7. The method of claim 1, wherein the $T_{max}$ of PEGylated C-peptide is between about 1.8 to about 3.3 days.

8. The method of claim 1, wherein the half-life of PEGylated C-peptide is between about 5.0 days and about 11.2 days.

9. The method of claim 1, wherein the $AUC_\tau$ of PEGylated C-peptide is between about 3.1 nM·day and about 85 nM·day.

10. The method of claim 9, wherein the $AUC_\tau$ of PEGylated C-peptide is between about 13.8 nM·day and about 41.5 nM·day.

11. The method of claim 1, wherein the volume of distribution of PEGylated C-peptide is between about 5.8 L and about 22 L.

12. The method of claim 11, wherein the volume of distribution of PEGylated C-peptide is between about 10 L and about 15 L.

13. The method of claim 1, wherein the clearance of PEGylated C-peptide is between about 0.8 L/day and about 2.2 L/day.

14. The method of claim 13, wherein the clearance of PEGylated C-peptide is between about 1.1 L/day and about 1.6 L/day.

15. The method of claim 1, wherein the degree of fluctuation of PEGylated C-peptide is between about 36% and about 50%.

16. The method of claim 1, wherein the PEGylated C-peptide is administered every 7 days.

17. The method of claim 1, wherein the PEGylated C-peptide is CBX129801.

18. The method of claim 17, wherein the amount of CBX129801 administered is between about 0.3 mg and about 3.3 mg every 7 days.

19. The method of claim 18, wherein the amount of CBX129801 administered is about 0.3 mg, about 0.8 mg, about 1.0 mg, about 2.4 mg, or about 3.3 mg, every 7 days.

20. The method of claim 1, wherein the disorder is selected from the group consisting of peripheral neuropathy, autonomic neuropathy, nephropathy, erectile dysfunction, female sexual dysfunction, and retinopathy.

21. The method of claim 20, wherein the disorder is peripheral neuropathy.

22. The method of claim 20, wherein the disorder is nephropathy.

23. The method of claim 20, wherein the disorder is erectile dysfunction or female sexual function.

24. A method for treating nerve damage or improving or slowing decline of nerve conductance or velocity in a diabetic subject, comprising subcutaneously administering to the subject a therapeutically effective amount of PEGylated C-peptide, wherein the PEGylated C-peptide has the structure:

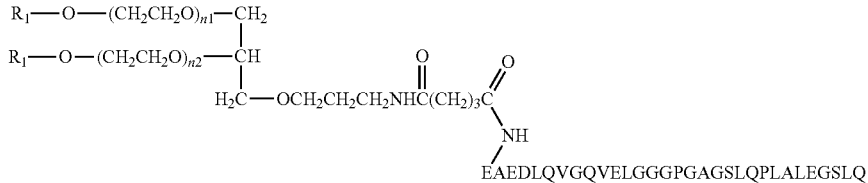

EAEDLQVGQVELGGGPGAGSLQPLALEGSLQ wherein each $R_1$ is alkyl;
$n_1$ is 200 to 800;
$n_2$ is 200 to 800; and
the polyethylene glycol (PEG) moiety

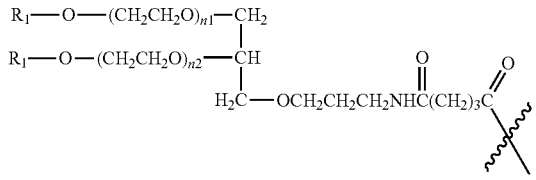

has a molecular weight of about 40 kDa to about 50 kDa.

25. The method of claim 24, wherein the $C_{ave}$ of PEGylated C-peptide is between about 0.44 nM and about 12.2 nM, or between about 2.0 nM and about 5.9 nM.

26. The method of claim 24, wherein the $C_{max}$ of PEGylated C-peptide is between about 0.34 nM and about 9.0 nM.

27. The method of claim 26, wherein the $C_{min}$ of PEGylated C-peptide is between about 1.7 nM and about 4.9 nM.

28. The method of claim 24, wherein the $C_{max}$ of PEGylated C-peptide is between about 0.5 nM and about 14.5 nM.

29. The method of claim 28, wherein the $C_{max}$ of PEGylated C-peptide is between about 2.3 nM and about 6.7 nM.

30. The method of claim 24, wherein the $T_{max}$ of PEGylated C-peptide is between about 1.8 to about 3.3 days.

31. The method of claim 24, wherein the half-life of PEGylated C-peptide is between about 5.0 days and about 11.2 days.

32. The method of claim 24, wherein the $AUC_\tau$ of PEGylated C-peptide is between about 3.1 nM·day and about 85 nM·day.

33. The method of claim 32, wherein the $AUC_\tau$ of PEGylated C-peptide is between about 13.8 nM·day and about 41.5 nM·day.

34. The method of claim 24, wherein the volume of distribution of PEGylated C-peptide is between about 5.8 and about 22 L.

35. The method of claim 34, wherein the volume of distribution of PEGylated C-peptide is between about 10 and about 15 L.

36. The method of claim 24, wherein the clearance of PEGylated C-peptide is between about 0.8 and about 2.2 L/day.

37. The method of claim 36, wherein the clearance of PEGylated C-peptide is between about 1.1 and about 1.6 L/day.

38. The method of claim 24, wherein the degree of fluctuation of PEGylated C-peptide is between about 36% and about 50%.

39. The method of claim 24, wherein the PEGylated C-peptide is administered every 7 days.

40. The method of claim 24, wherein the PEGylated C-peptide is CBX129801.

41. The method of claim 40, wherein the amount of CBX129801 administered is between about 0.3 mg and about 3.3 mg every 7 days.

42. The method of claim 41, wherein the amount of CBX129801 administered is about 0.3 mg, about 0.8 mg, about 1.0 mg, about 2.4 mg, or about 3.3 mg, every 7 days.

43. The method of claim 24, wherein said treating, slowing, or improving results in an improvement of at least 1 m/sec in nerve conduction velocity compared to nerve conduction velocity prior to starting PEGylated C-peptide administration.

44. The method of claim 43, wherein said treating, slowing, or improving results in an improvement of at least 2 m/sec in nerve conduction velocity compared to nerve conduction velocity prior to starting PEGylated C-peptide administration.

45. The method of claim 24, wherein said treating, slowing, or improving with PEGylated C-peptide prevents a decrease of at least 1 m/sec in nerve conduction velocity compared to untreated patients.

46. The method of claim 45, wherein said treating, slowing, or improving with PEGylated C-peptide prevents a decrease of at least 2 m/sec in nerve conduction velocity compared to untreated patients.

47. The method of claim 24, further comprising administering insulin.

48. The method of claim 47, further comprising the step of adjusting the dosage amount, type, or frequency of insulin administered based on monitoring the patient's altered insulin requirements after administration of the effective amount of PEGylated C-peptide, wherein the adjusted dose of insulin reduces the risk, incidence, or severity of hypoglycemia, wherein the adjusted dose of insulin is at least 10% less than the patient's insulin dose prior to starting PEGylated C-peptide treatment.

49. The method of claim 48, wherein the adjusted dose of insulin is about 10% less to about 35% less than the patient's insulin dose prior to starting PEGylated C-peptide treatment.

* * * * *

SEQUENCE LISTING

<160> NUMBER OF SEQ ID NOS: 2

<210> SEQ ID NO 1
<211> LENGTH: 31
<212> TYPE: PRT
<213> ORGANISM: Homo sapiens

<400> SEQUENCE: 1

```
Glu Ala Glu Asp Leu Gln Val Gly Gln Val Glu Leu Gly Gly Gly Pro
1               5                  10                  15
Gly Ala Gly Ser Leu Gln Pro Leu Ala Leu Glu Gly Ser Leu Gln
            20                  25                  30
```

<210> SEQ ID NO 2
<211> LENGTH: 5
<212> TYPE: PRT
<213> ORGANISM: Artificial Sequence
<220> FEATURE:
<223> OTHER INFORMATION: Synthesized

<400> SEQUENCE: 2

```
Glu Gly Ser Leu Gln
1               5
```